(12) United States Patent
Clarke et al.

(10) Patent No.: US 9,752,150 B2
(45) Date of Patent: Sep. 5, 2017

(54) TARGETING CHROMATIN MODIFIERS FOR THE TREATMENT OF MEDICAL CONDITIONS

(71) Applicant: The Board of Trustees of the Leland Stanford Junior University, Stanford, CA (US)

(72) Inventors: Michael F. Clarke, Menlo Park, CA (US); Maddalena Adorno, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/768,864

(22) PCT Filed: Mar. 14, 2014

(86) PCT No.: PCT/US2014/029291
§ 371 (c)(1),
(2) Date: Aug. 19, 2015

(87) PCT Pub. No.: WO2014/144752
PCT Pub. Date: Sep. 18, 2014

(65) Prior Publication Data
US 2016/0046946 A1 Feb. 18, 2016

Related U.S. Application Data

(60) Provisional application No. 61/788,795, filed on Mar. 15, 2013.

(51) Int. Cl.
*A01N 43/04* (2006.01)
*A61K 31/70* (2006.01)
*C12N 15/113* (2010.01)
*C12Q 1/68* (2006.01)
*A61K 31/7125* (2006.01)
*A61K 31/711* (2006.01)
*A61K 31/713* (2006.01)
*A61K 31/7088* (2006.01)
*A61K 31/712* (2006.01)
*A61K 31/7105* (2006.01)
*A61K 31/7115* (2006.01)

(52) U.S. Cl.
CPC ........ *C12N 15/1137* (2013.01); *C12Q 1/6883* (2013.01); *A61K 31/7088* (2013.01); *A61K 31/711* (2013.01); *A61K 31/712* (2013.01); *A61K 31/713* (2013.01); *A61K 31/7105* (2013.01); *A61K 31/7115* (2013.01); *A61K 31/7125* (2013.01); *C12N 2310/14* (2013.01); *C12N 2310/531* (2013.01); *C12N 2320/30* (2013.01); *C12N 2330/51* (2013.01); *C12Q 2600/136* (2013.01); *C12Q 2600/158* (2013.01); *C12Q 2600/178* (2013.01); *C12Y 301/02015* (2013.01)

(58) Field of Classification Search
None
See application file for complete search history.

(56) References Cited

U.S. PATENT DOCUMENTS

2012/0258975 A1  10/2012  Yuan et al.

FOREIGN PATENT DOCUMENTS

| WO | WO 2005/030939 A2 | 4/2005 |
| WO | WO 2005/108949 A2 | 11/2005 |
| WO | WO 2007/100576 A2 | 9/2007 |
| WO | WO 2012/056048 A1 | 5/2012 |

OTHER PUBLICATIONS

Kowalski et al. Neural Plasticity, vol. 2012, Article ID 892749, 13 pages.*
Joo et al. Nature (2007), vol. 449, pp. 1068-1072.*
Cao et al, "Role of Bmi-1 and Ring1A in H2A ubiquitylation and hox gene silencing", Molecular Cell, Cell Press, Cambridge, MA, US, vol. 20, No. 6, Dec. 22, 2005, pp. 845-854.
Nijnik et al. "The critical role of histone H2A-deubiquitinase Mysm1 in hematopoiesis and lymphocyte differentiation", Blood, vol. 119, No. 6, Dec. 19, 2011, pp. 1370-1379.
Sippl et al. "Ubiquitin-specific proteases as cancer drug targets", Future Oncology, Future Medicine Ltd., London, GB, vol. 7, No. 5, May 1, 2011, pp. 619-632.
Wei et al. "Role of Bmi1 in H2A ubiquitylation and Hox gene silencing", Journal of Biological Chemistry, American Society for Biochemistry and Molecular Biology, US, vol. 281, No. 32, Aug. 11, 2006, pp. 22537-22544.
Xu et al. "Knock-down of ubiquitin-specific protease 22 by microRNA interference inhibits colorectal cancer growth", International Journal of Colorectal Disease, vol. 27, No. 1, Jul. 20, 2011, pp. 21-38.
Adorno et al. "Usp16 contributes to somatic stem cell defects in Down syndrome", Nature 501(7467): 1-19 (Sep. 19, 2013).
Boada et al. "Antagonism of NMDA receptors as a potential treatment for Down syndrome: a pilot randomized controlled trial", Translational Psychiatry 2(e141): 1-11 (Jul. 17, 2012).
Molofsky et al. "Bmi-1 promotes neural stem cell self-renewal and neural development but not mouse growth and survival by repressing the p16Ink4a and p19Arf senescence pathways", Genes & Development 19(12): 1432-1437 (Jun. 15, 2005).

(Continued)

*Primary Examiner* — Patrick Lewis
(74) *Attorney, Agent, or Firm* — Bret E. Field; Bozicevic, Field & Francis LLP

(57) ABSTRACT

Methods and compositions are provided for the treatment of medical conditions associated with a reduced rate of stem cell self-renewal or that will be responsive to an increased rate of stem cell self-renewal. Aspects of the methods include inhibiting H2A deubiquitinating enzyme activity in cells, e.g. by administering an effective amount of an H2A deubiquitinating enzyme antagonist. Also provided are screens to identify therapeutics for the treatment of medical conditions associated with a reduced rate of stem cell self-renewal or that will be responsive to an increased rate of stem cell self-renewal.

14 Claims, 44 Drawing Sheets

(56) References Cited

OTHER PUBLICATIONS

Nemetz et al. "Traumatic Brain Injury and Time to Onset of Alzheimer's Disease: A Population-based Study", Am. J. Epidemiol. 149(1): 32-40 (Jan. 1, 1999).

Noguchi et al. "Constructing a Lentivirus Expressing USP16, a Possible Negative Player in Self-Renewal", Stanford University Stem Cell Biology and Regenerative Medicine Institute, Oct. 5, 2012, 1 page. (Retrieved from the internet on Jul. 9, 2014).

Rayess et al. "Cellular senescence and tumor suppressor gene p16", Int. J. Cancer. 130(8): 1715-1725 (Apr. 15, 2012).

\* cited by examiner

FIGURE 1
A
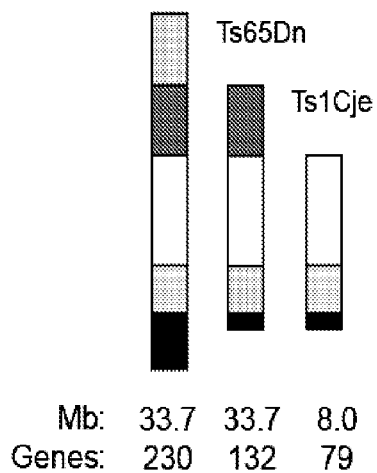
B
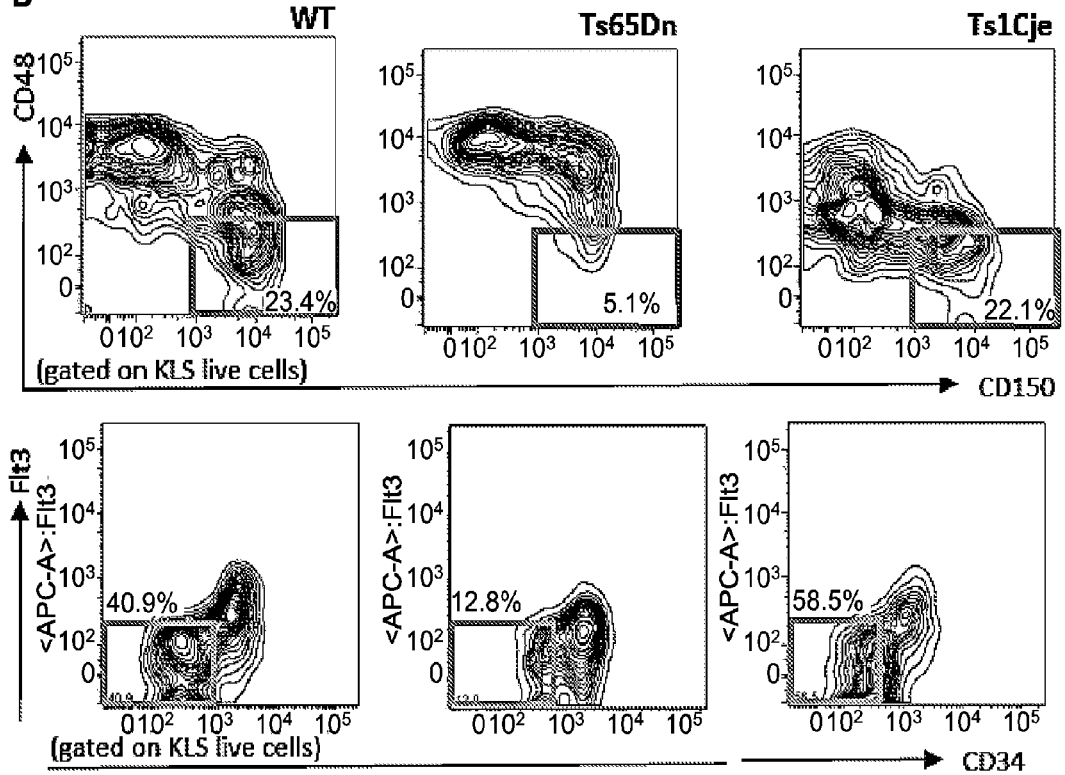

FIGURE 1
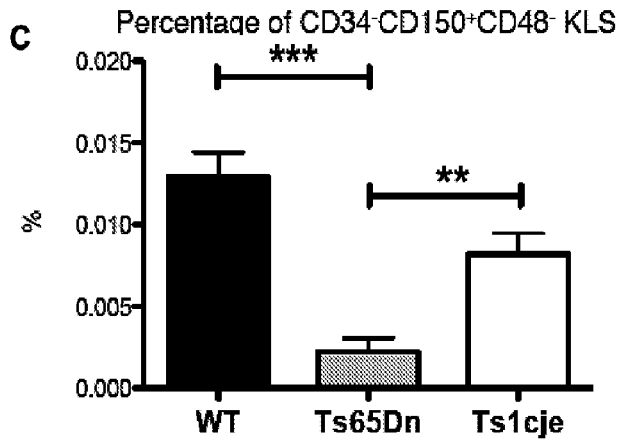
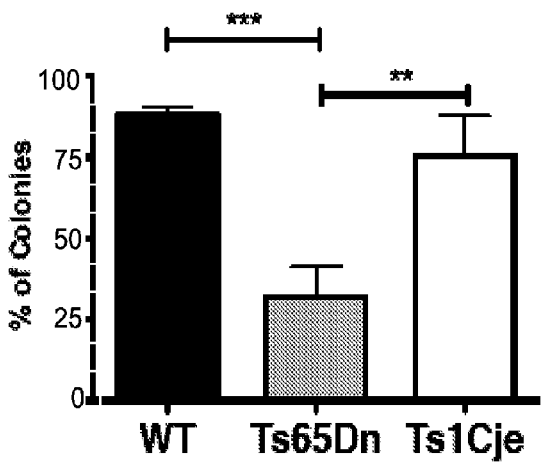
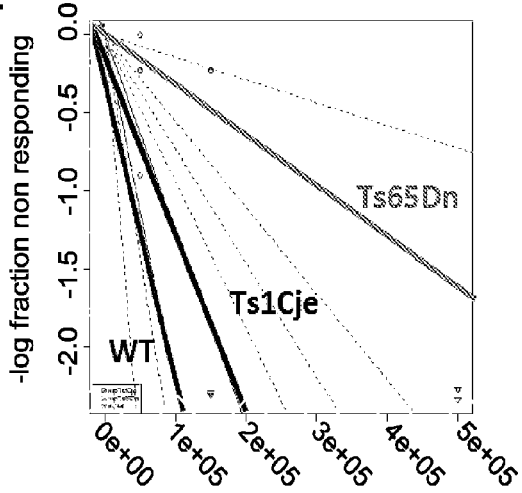

FIGURE 2
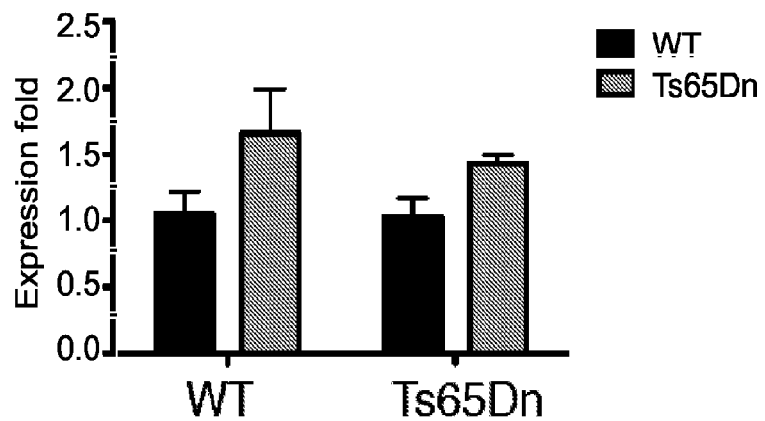
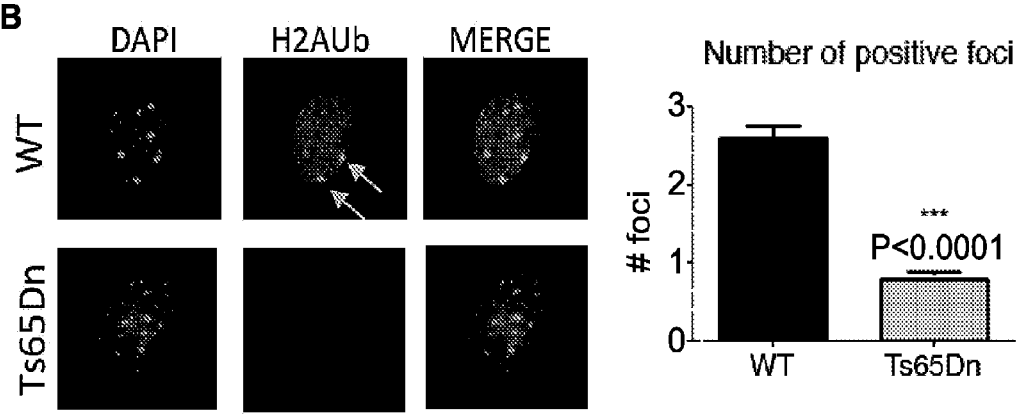
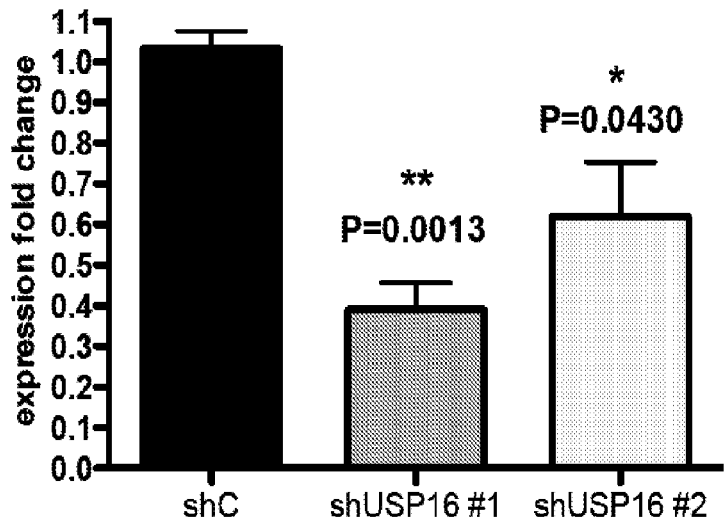

FIGURE 2
D Colonies from single HSCs
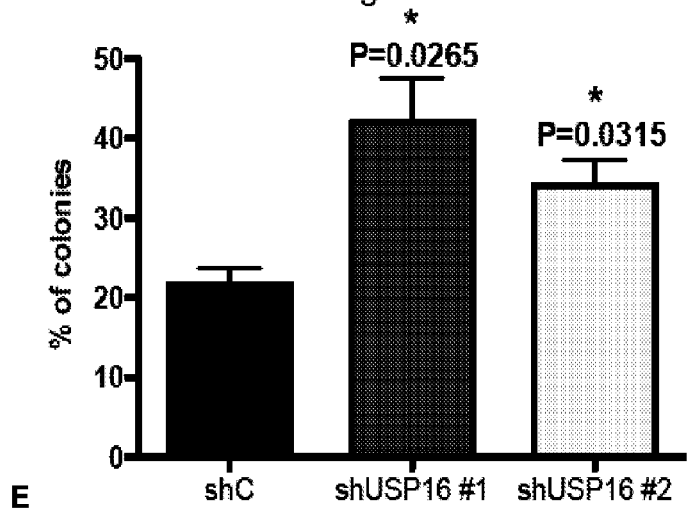
E
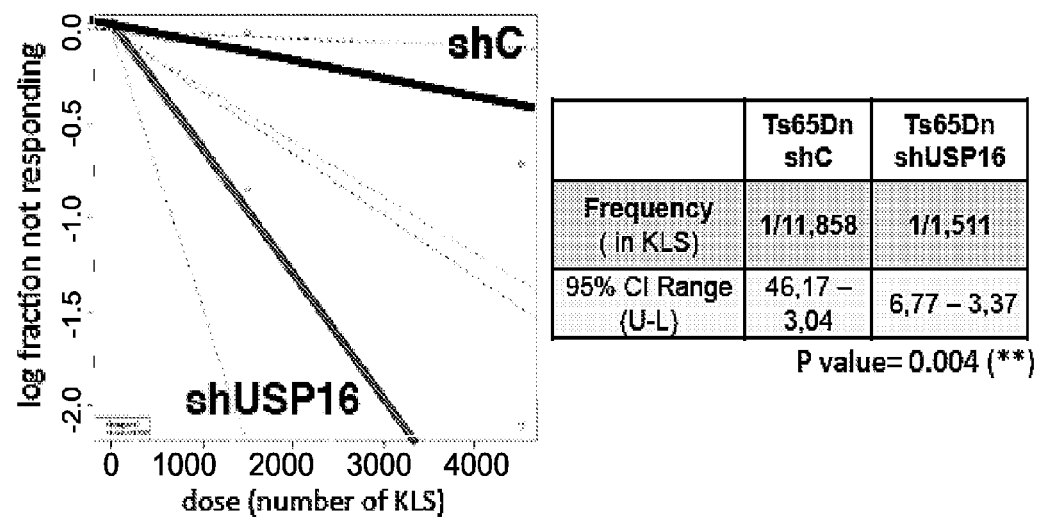
F
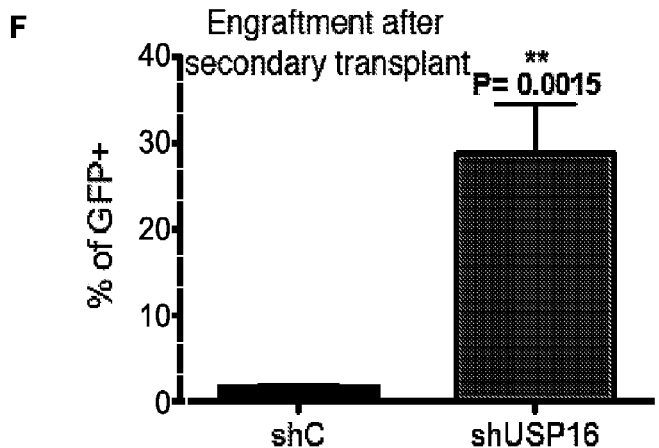

|  | WT | Ts65Dn | Ts65Dn/ Usp16het | Usp16het |
|---|---|---|---|---|
| Frequency at P1 | 1/71.63 | 1/176.50 | 1/80.97 | 1/83.07 |
| 95% CI Range (U-L) | 103.7 – 49.57 | 254.75 - 122.25 | 112.33 – 58.57 | 114.65 – 61.1 |
| Frequency at P4 | 1/20.8 | 1/957.9 | 1/21.8 | 1/18.6 |
| 95% CI Range (U-L) | 28.8 – 15.0 | 1,484.6 – 618 | 30.0 - 15.8 | 26.2 - 13.2 |

P<0.00001   P<0.00001

FIGURE 3
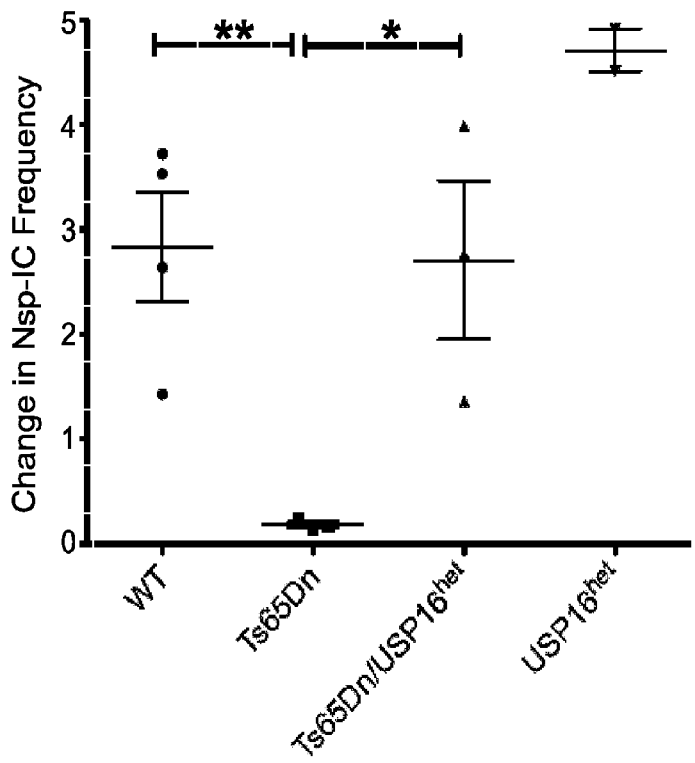
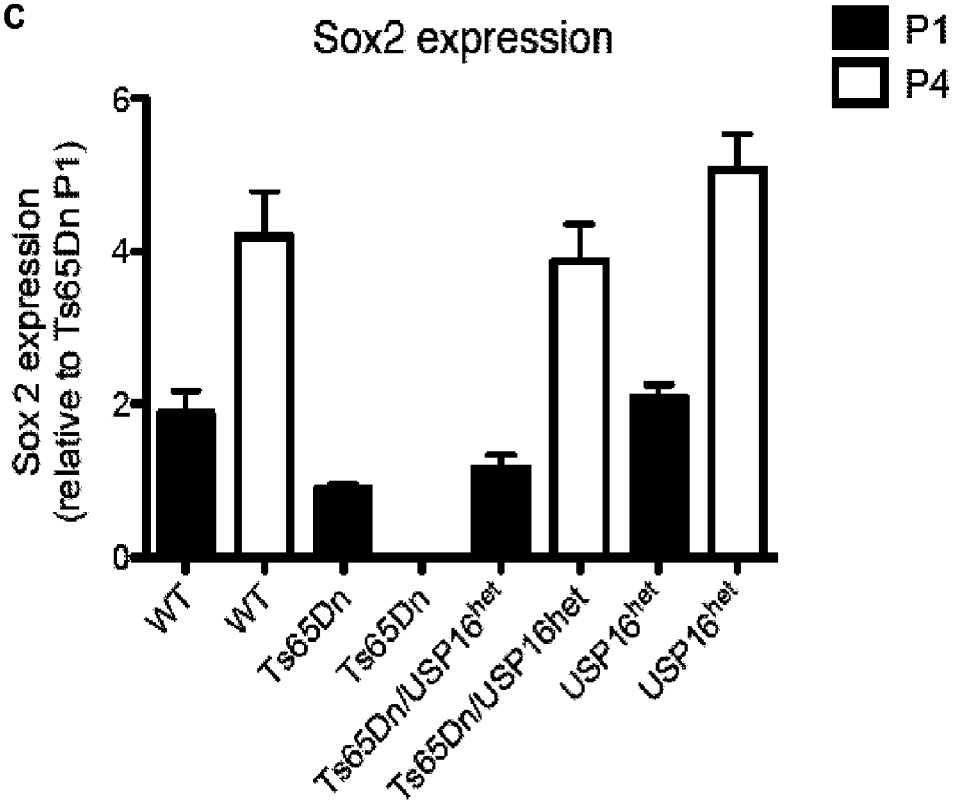

D

|  | WT | Ts65Dn | Ts65Dn/ Usp16het | Usp16het |
|---|---|---|---|---|
| Frequency in CD133+/Egfr+ | 1/17.6 | 1/97.3 | 1/17.6 | 1/20.2 |
| 95% CI Range | 25.8 – 12.0 | 142.7 – 66.3 | 25.8 – 12.0 | 29.2 – 13.9 |
| Frequency in CD15+/Egfr+ | 1/7.9 | 1/103.6 | 1/11.3 | 1/17.21 |
| 95% CI Range | 12.2 – 5.1 | 153 – 70.1 | 17.3 – 7.4 | 25.3 – 11.7 |

P<0.00001    P<0.00001

FIGURE 5
A
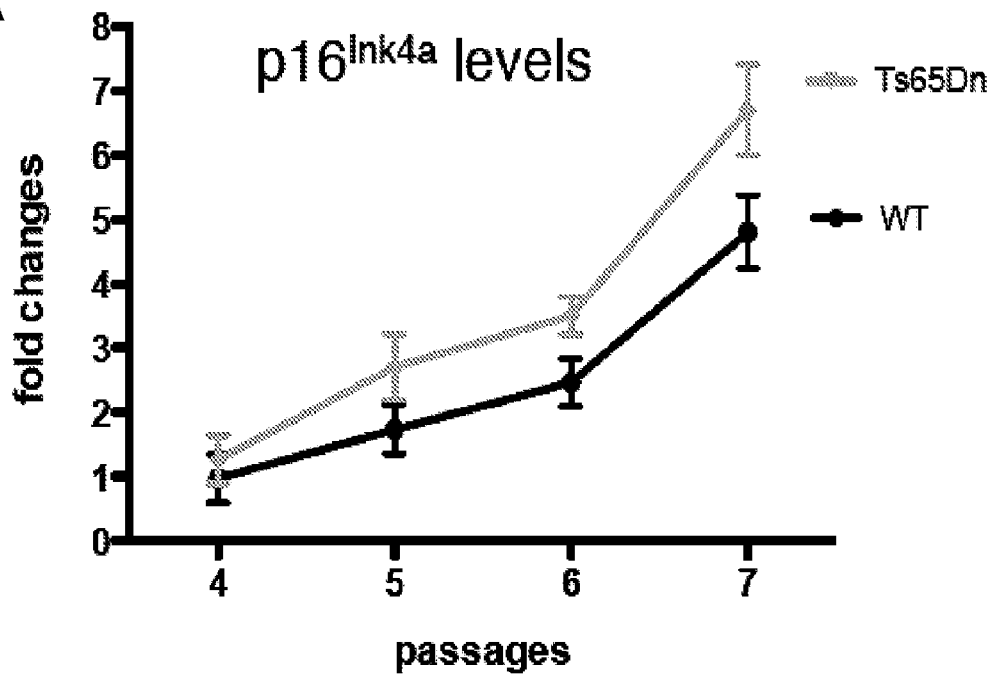
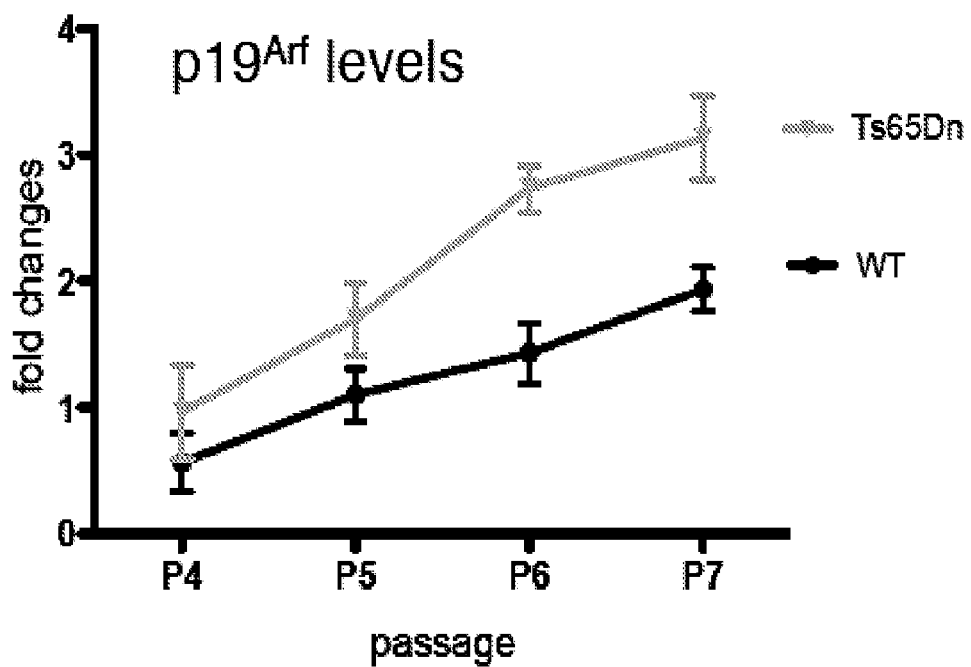

FIGURE 5
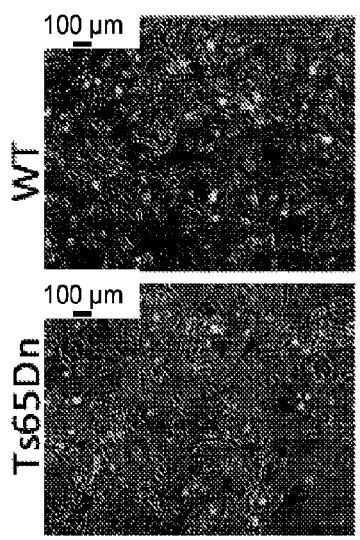
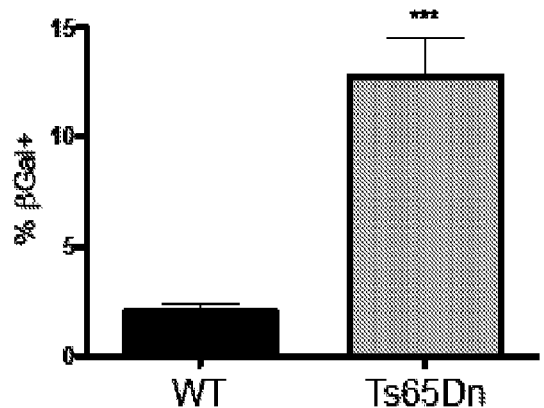
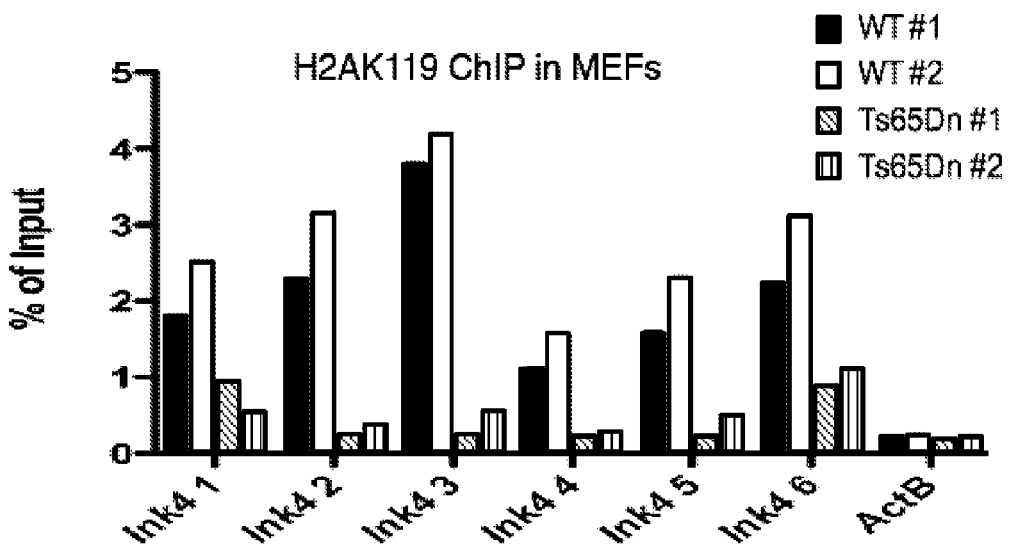

FIGURE 5
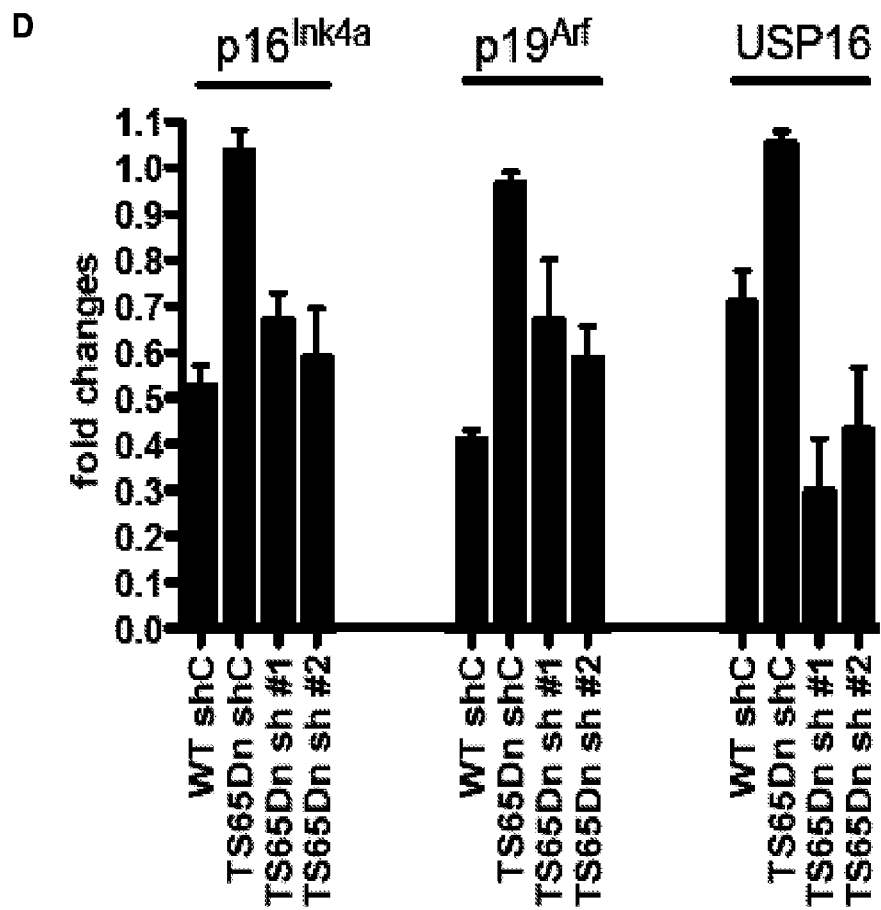
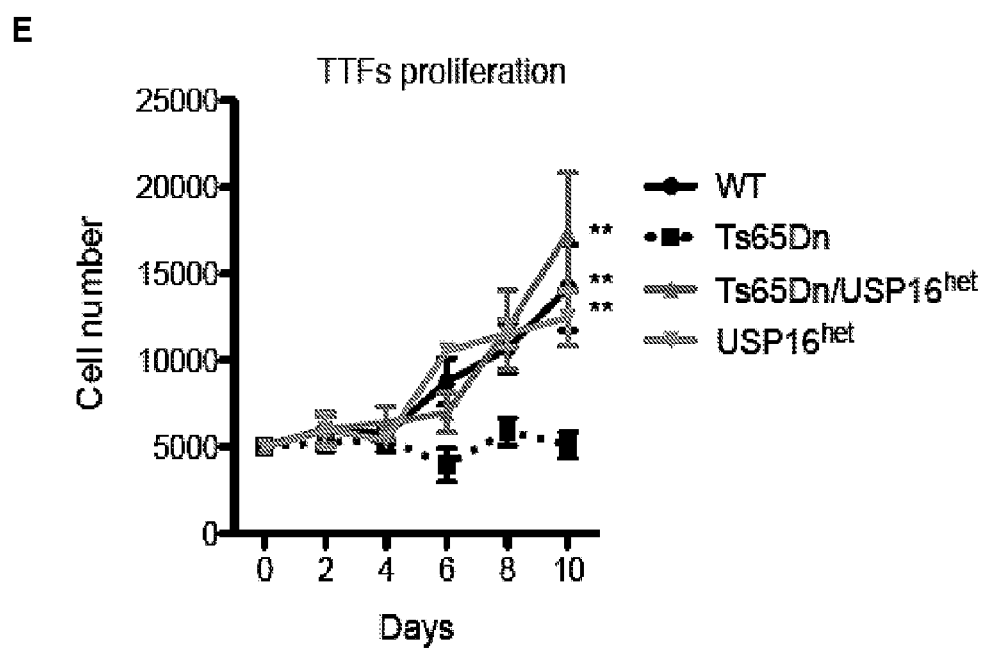

FIGURE 5
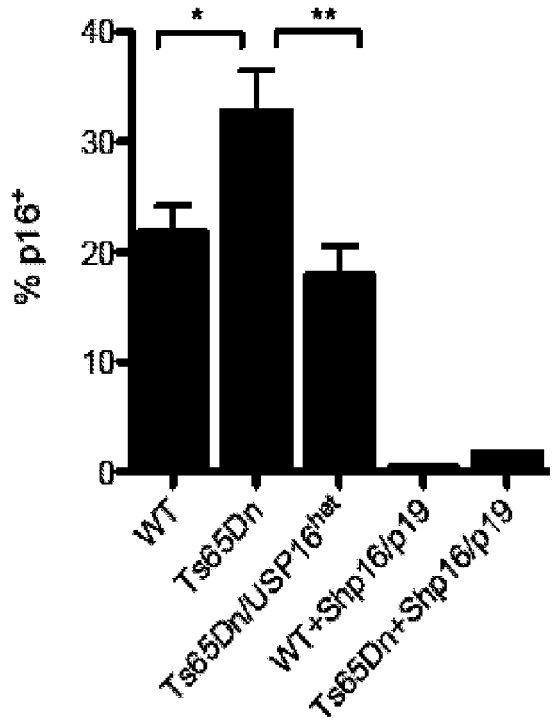
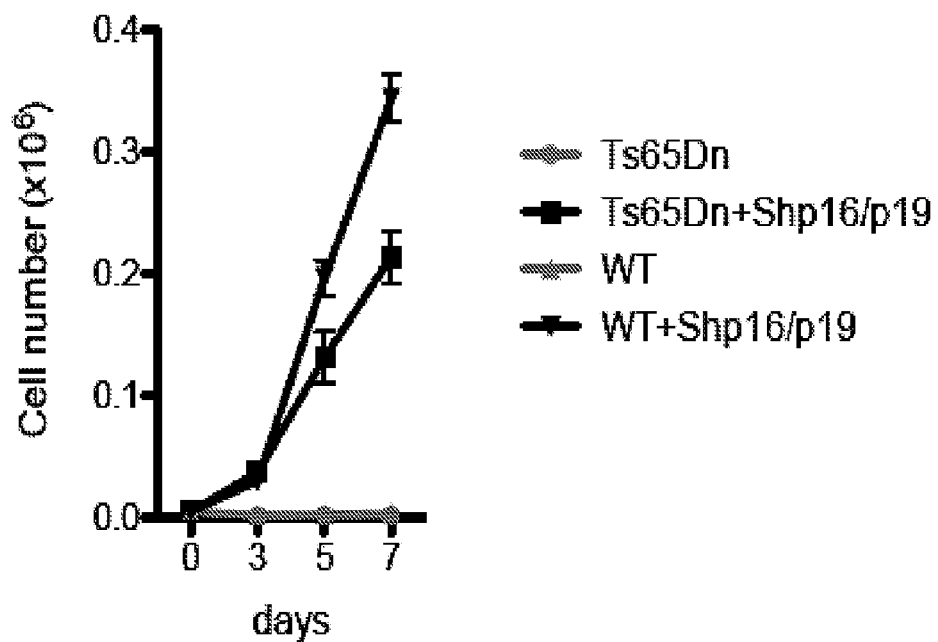

FIGURE 7 B (Cont. 2)    150.000 cells
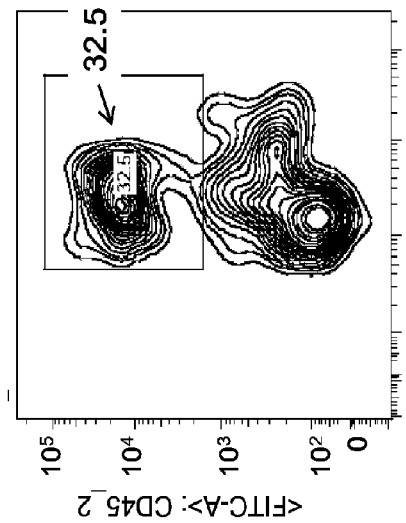 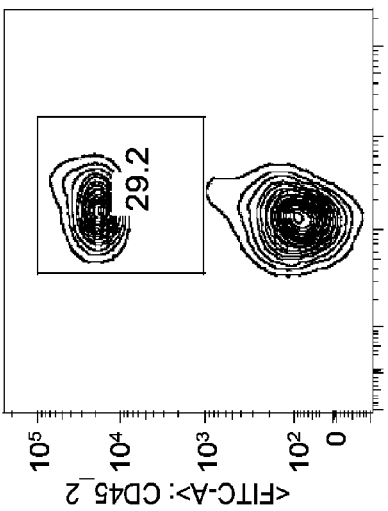 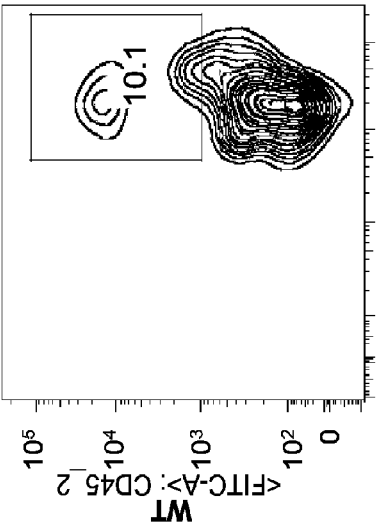
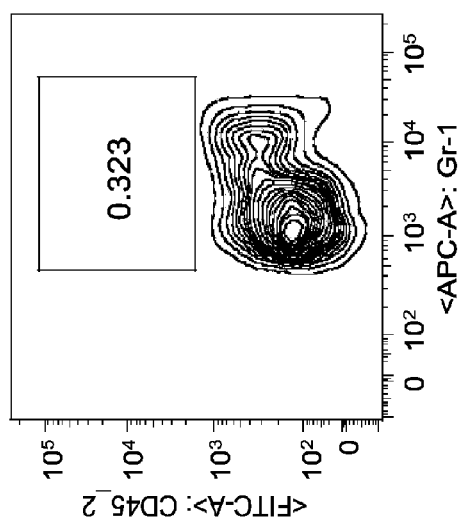 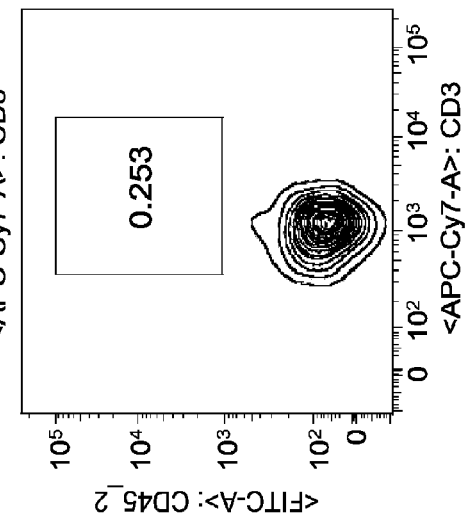 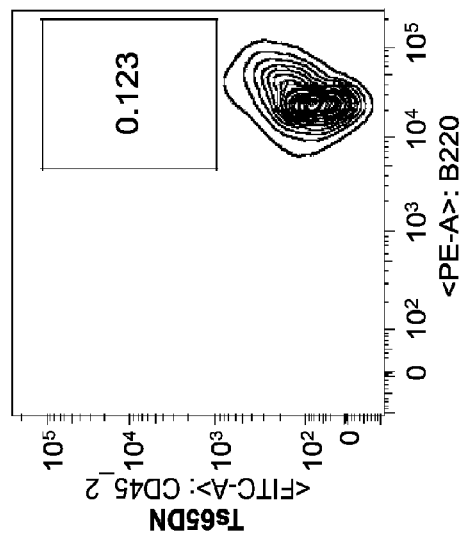

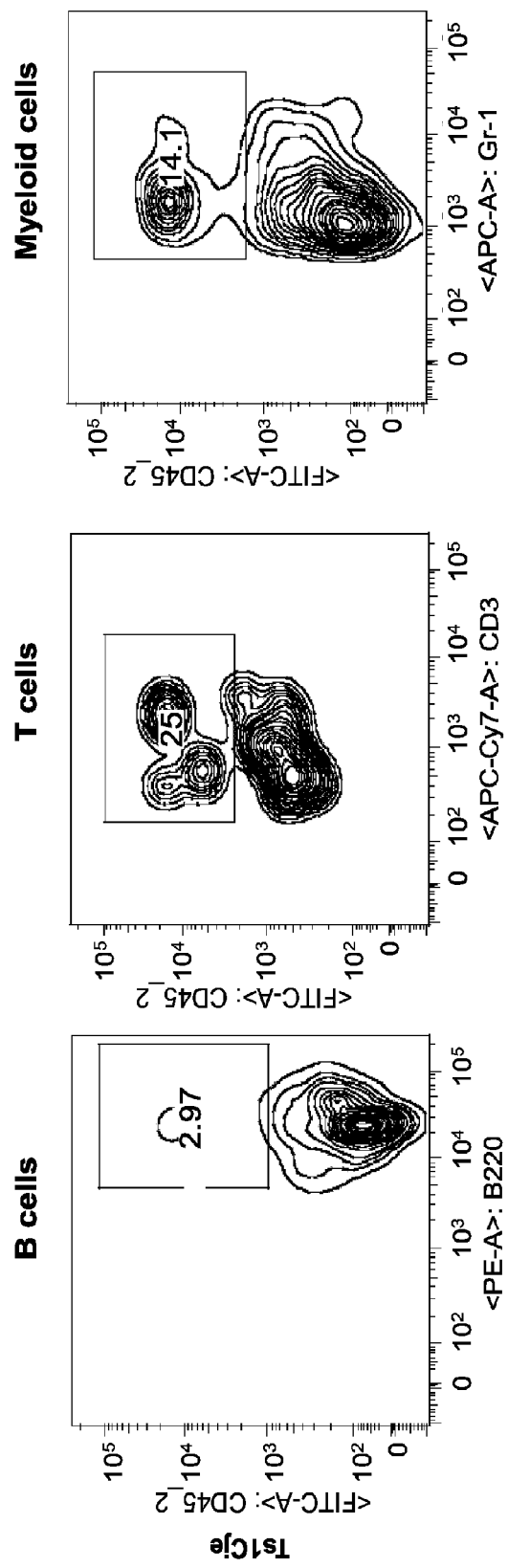
FIGURE 7 B (Cont. 3)    150.000 cells

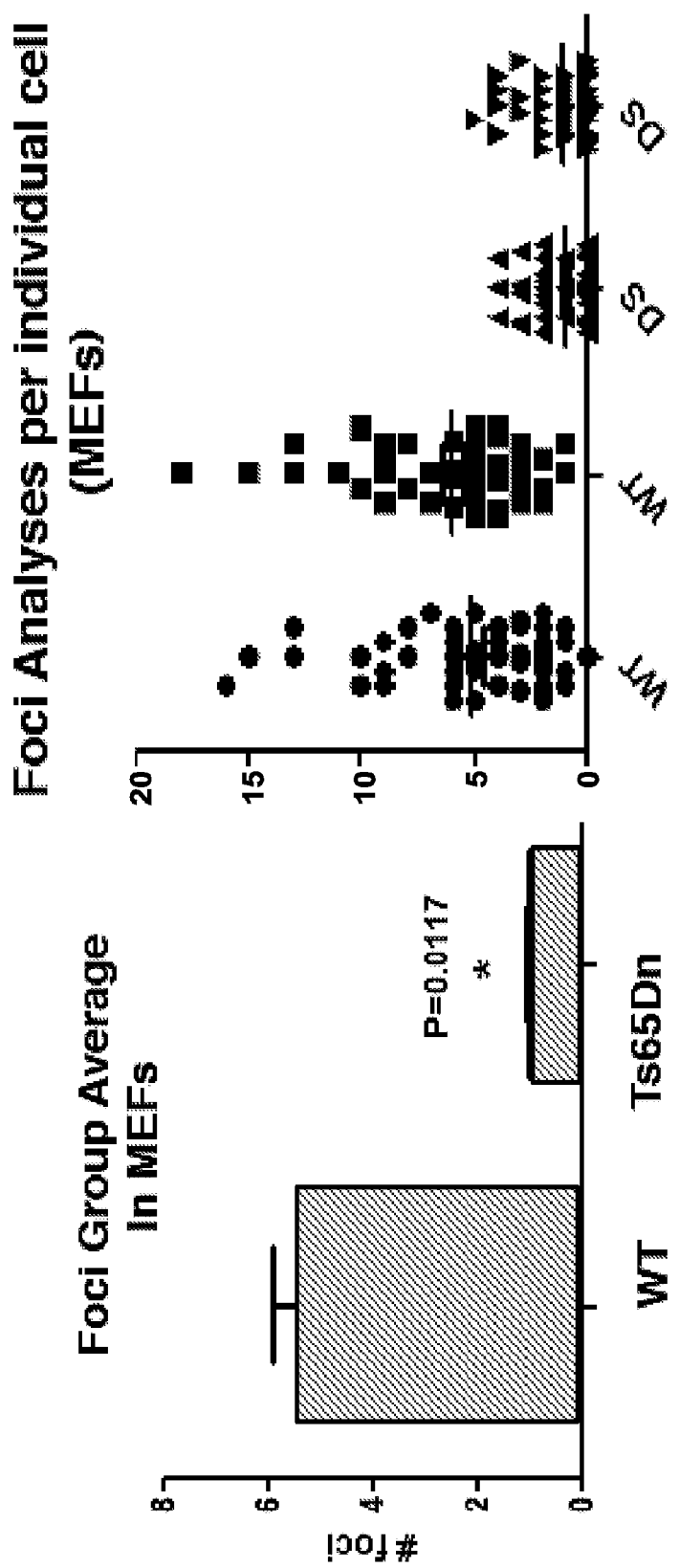
FIGURE 9  A

FIGURE 9    B    Semiquantification H2AUb intensity(MEFs)
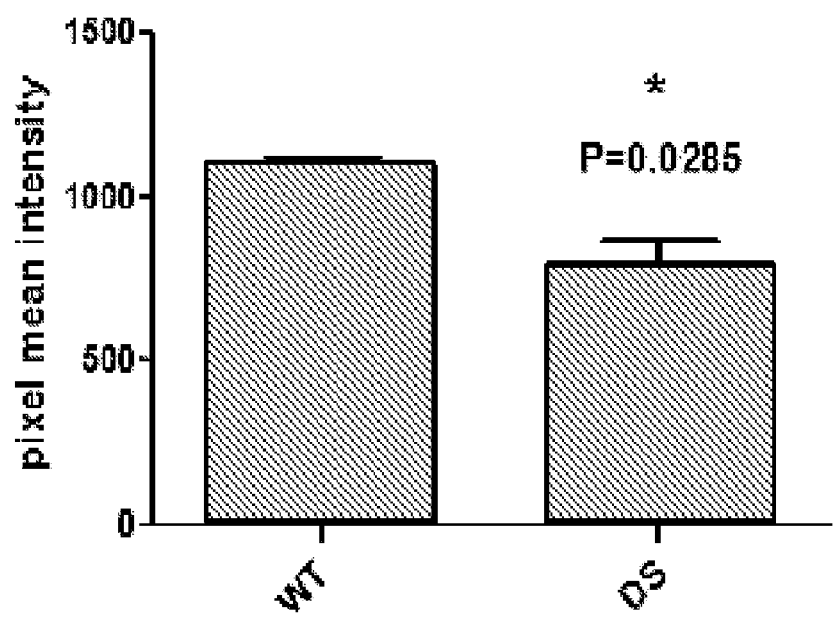
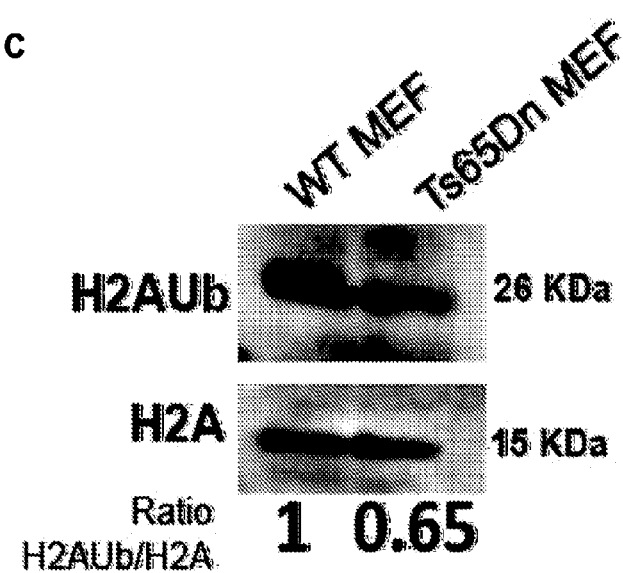

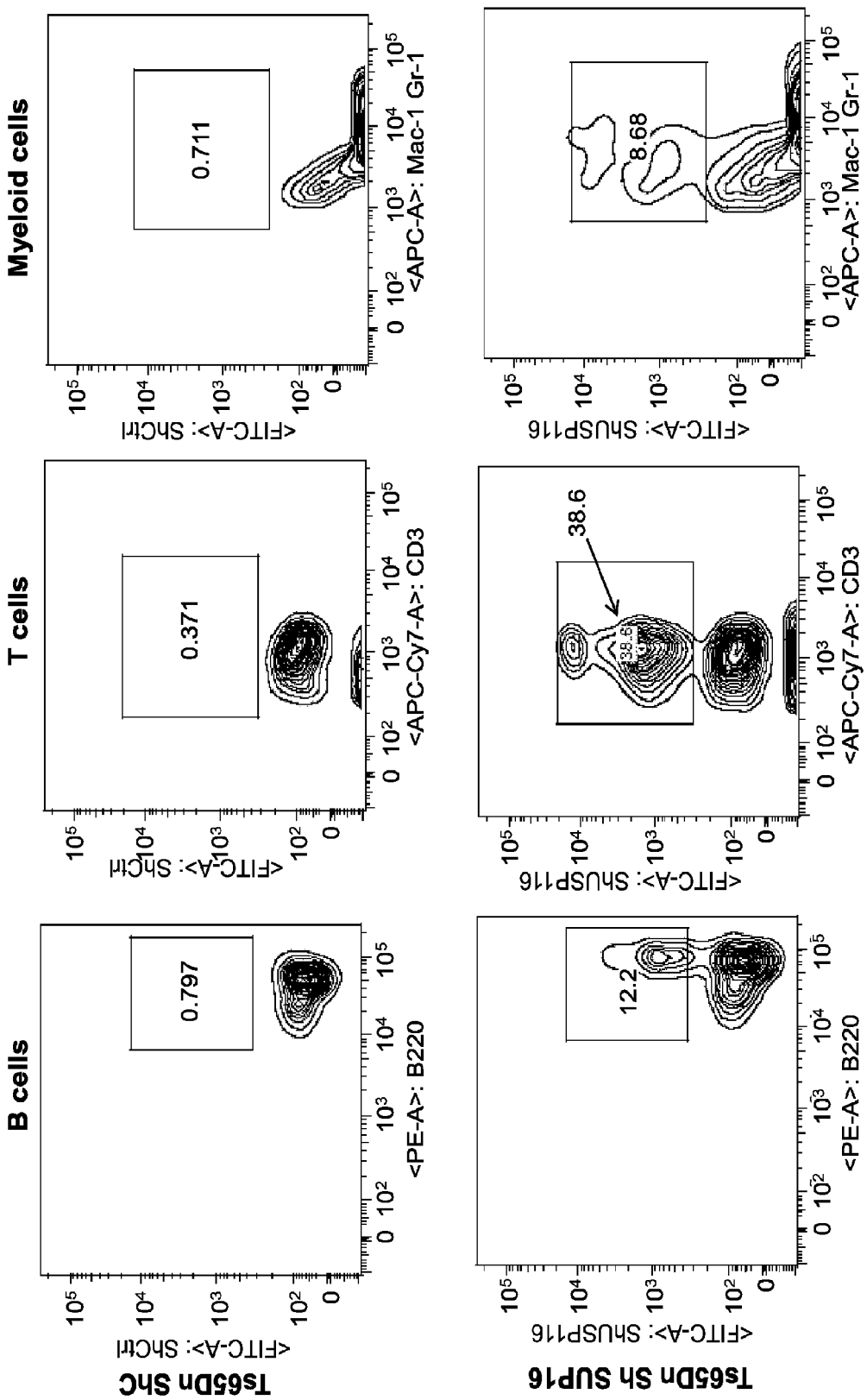

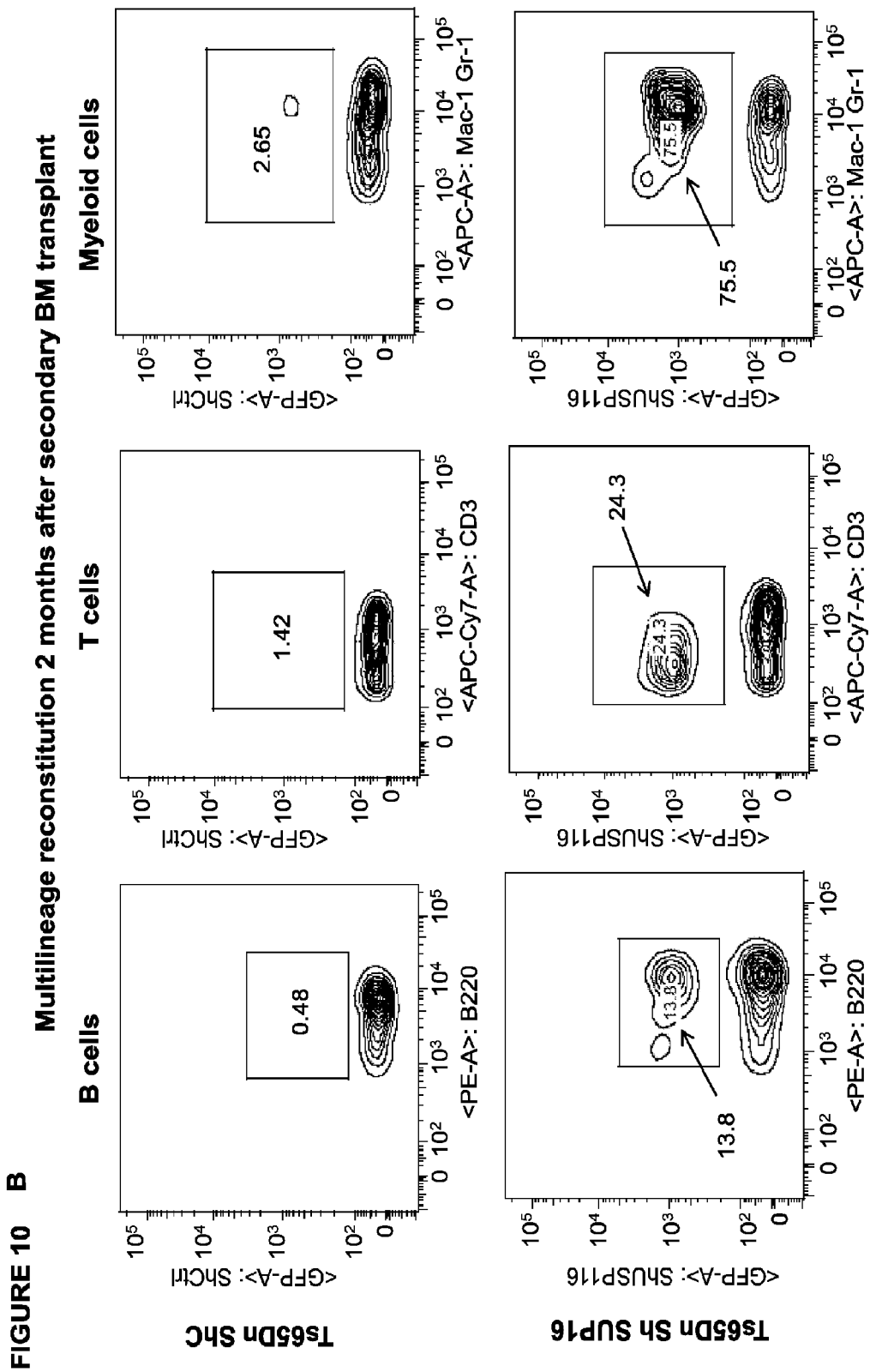

FIGURE 12  B (Cont. 1)
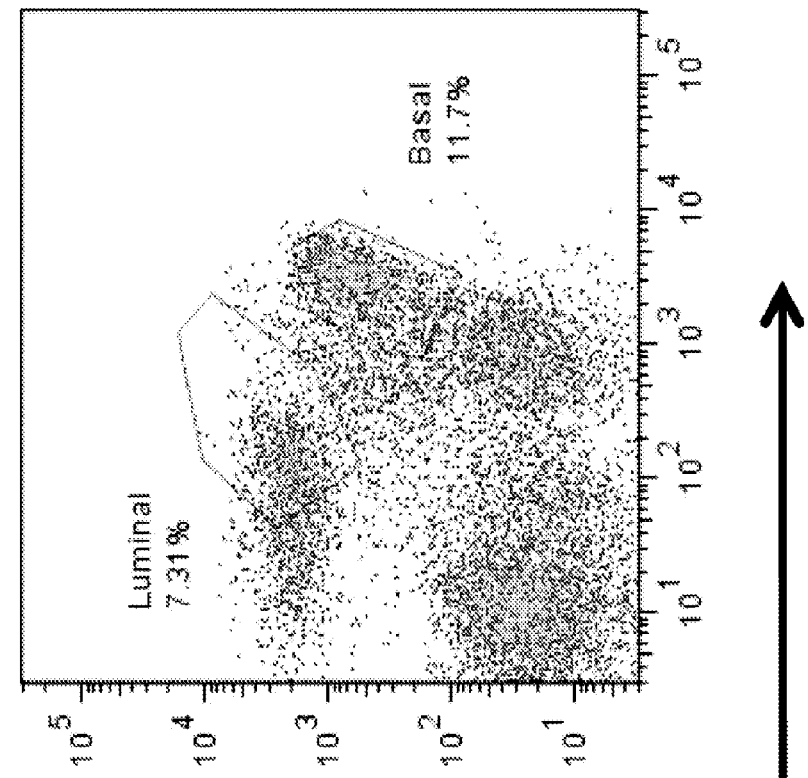
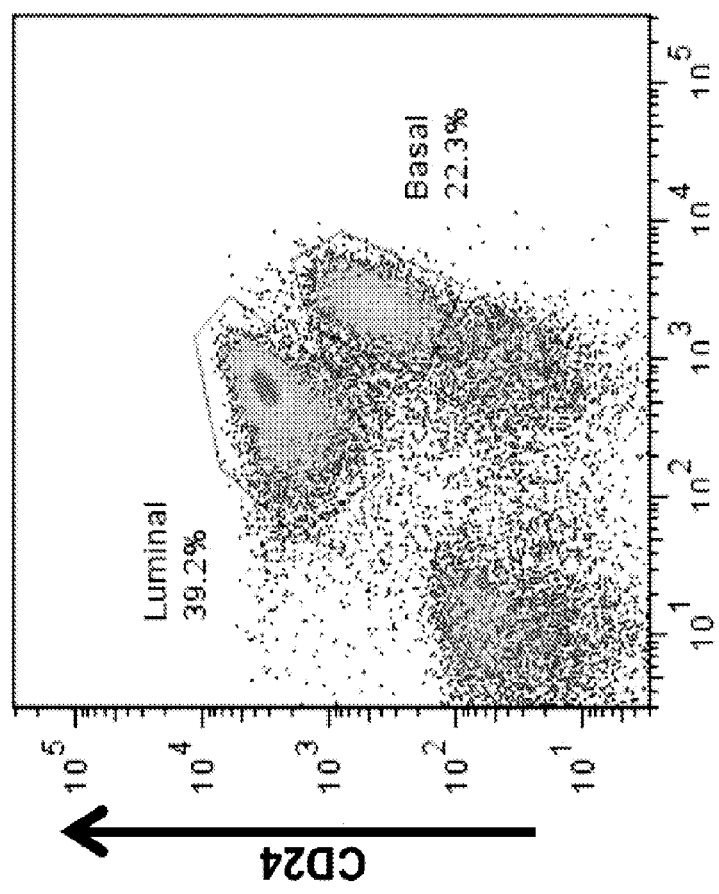

FIGURE 12 B (Cont. 2)
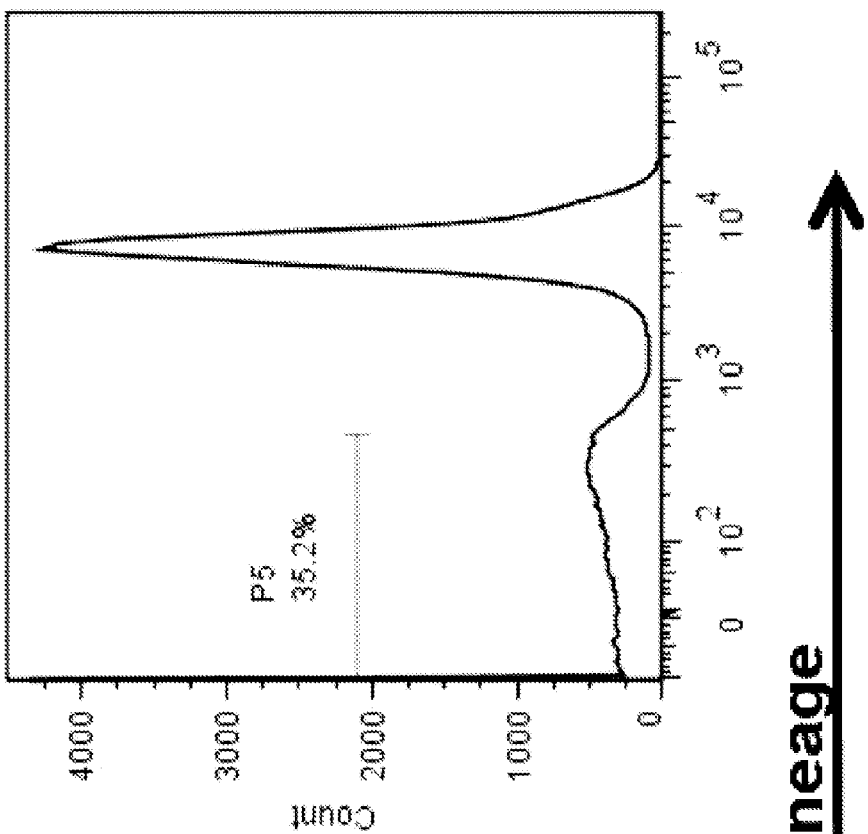
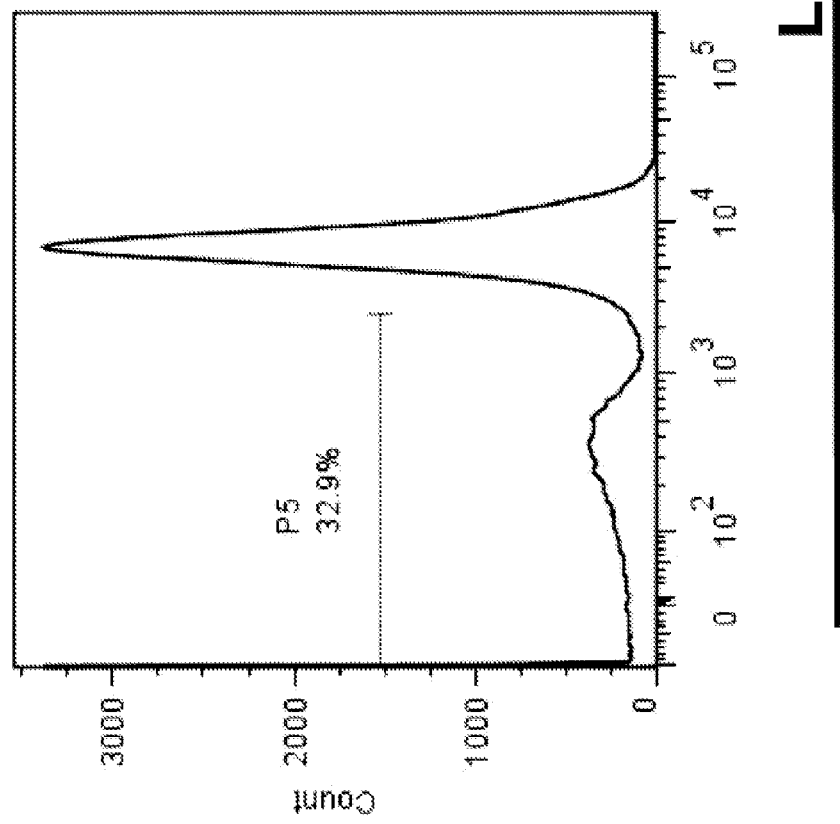

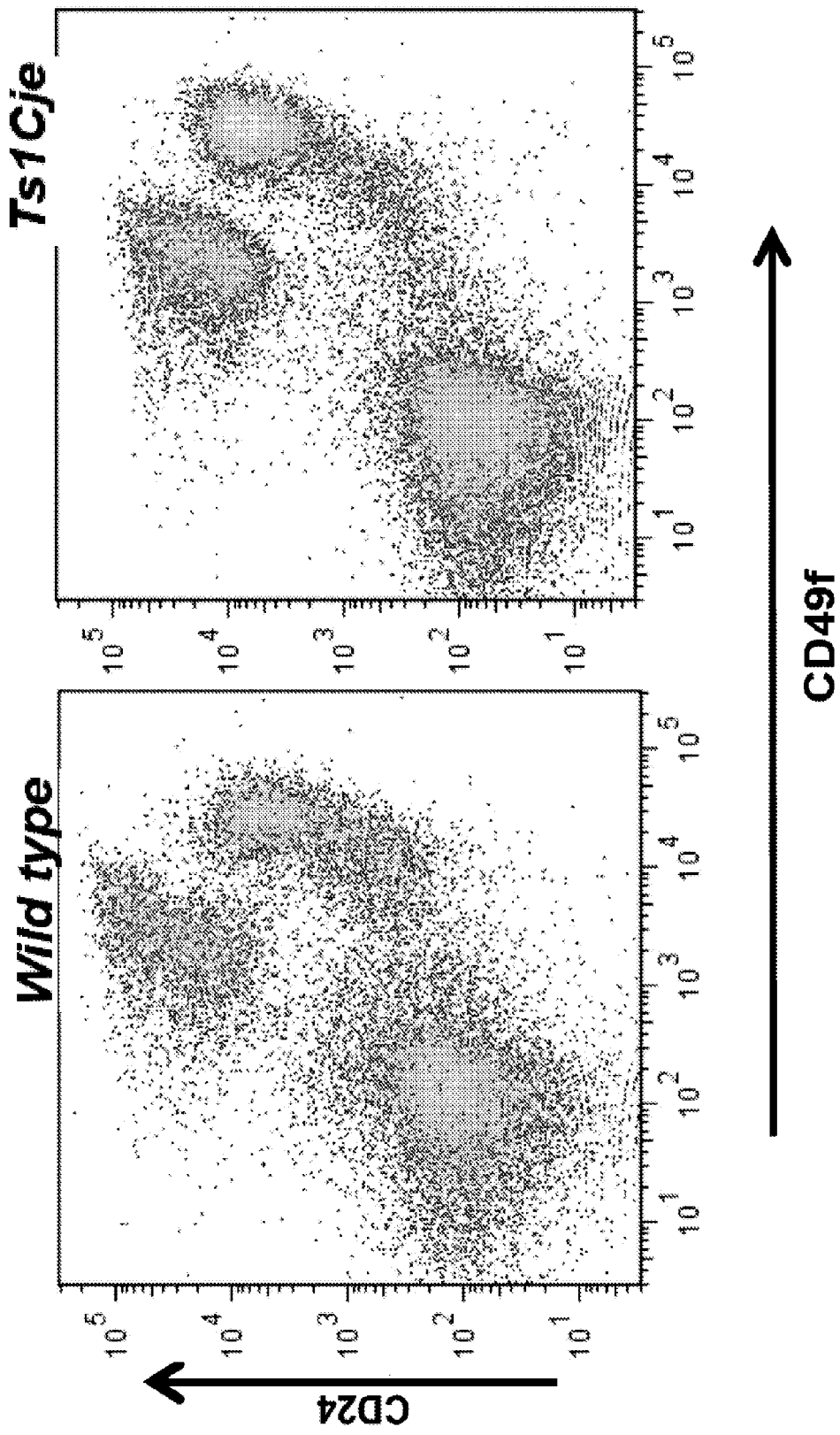
FIGURE 12  B (Cont. 3)

FIGURE 13
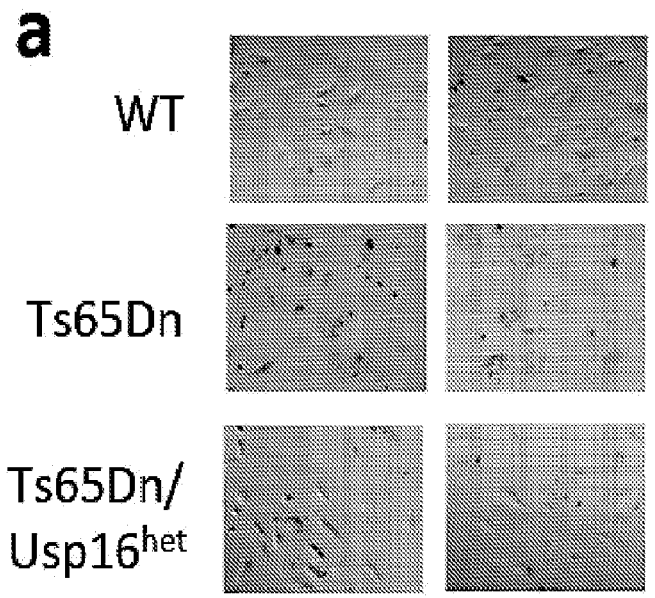
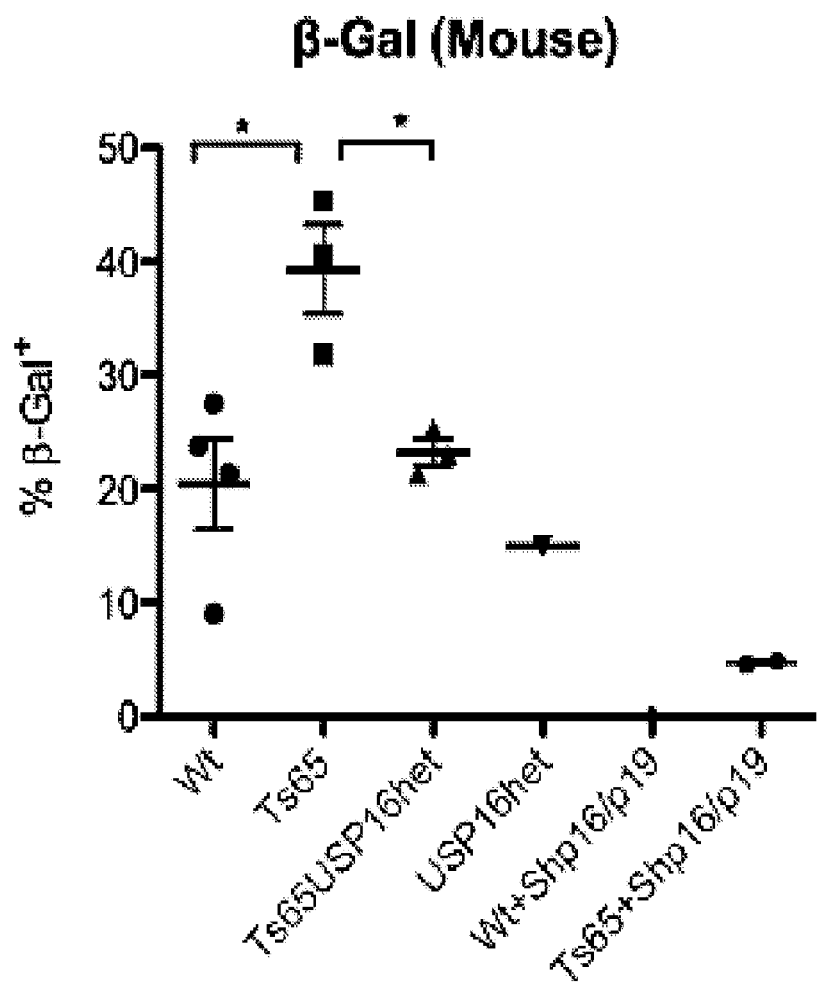

FIGURE 13
C
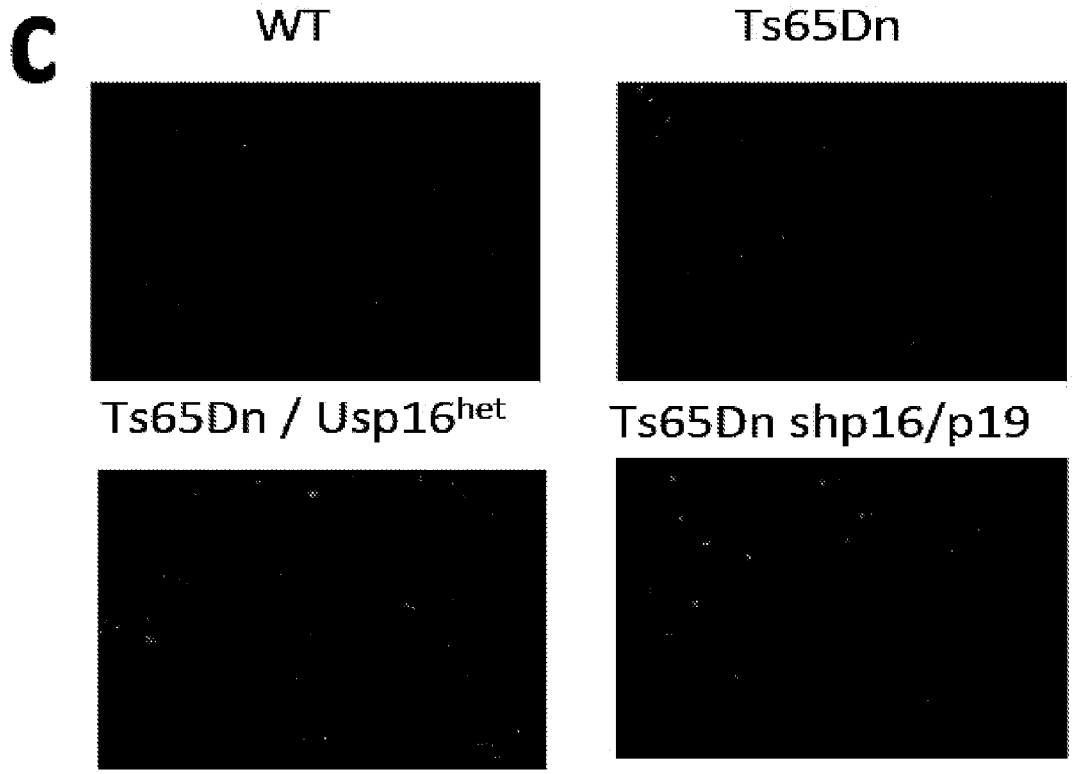
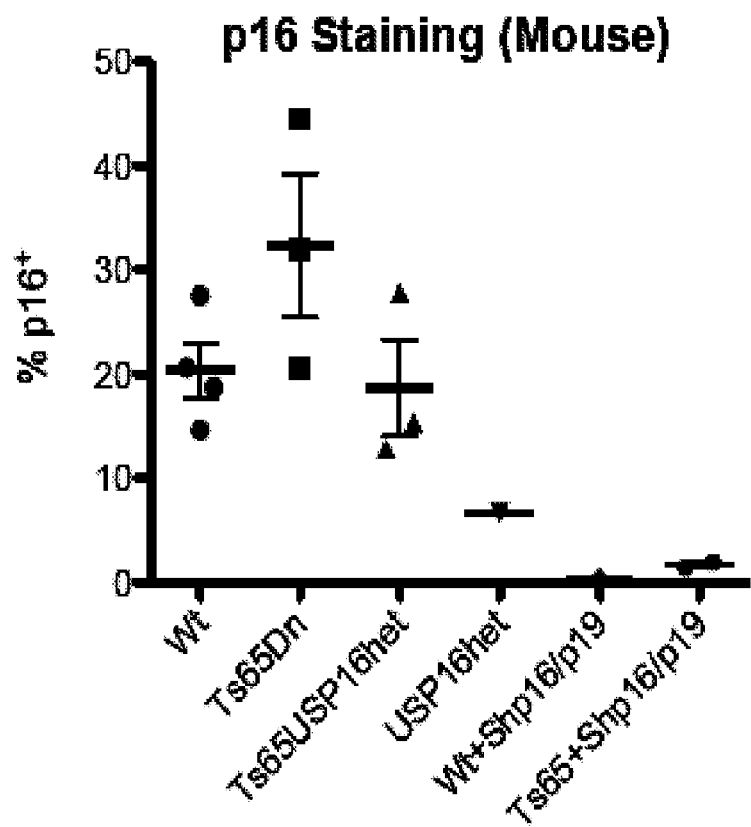

A

FIGURE 14
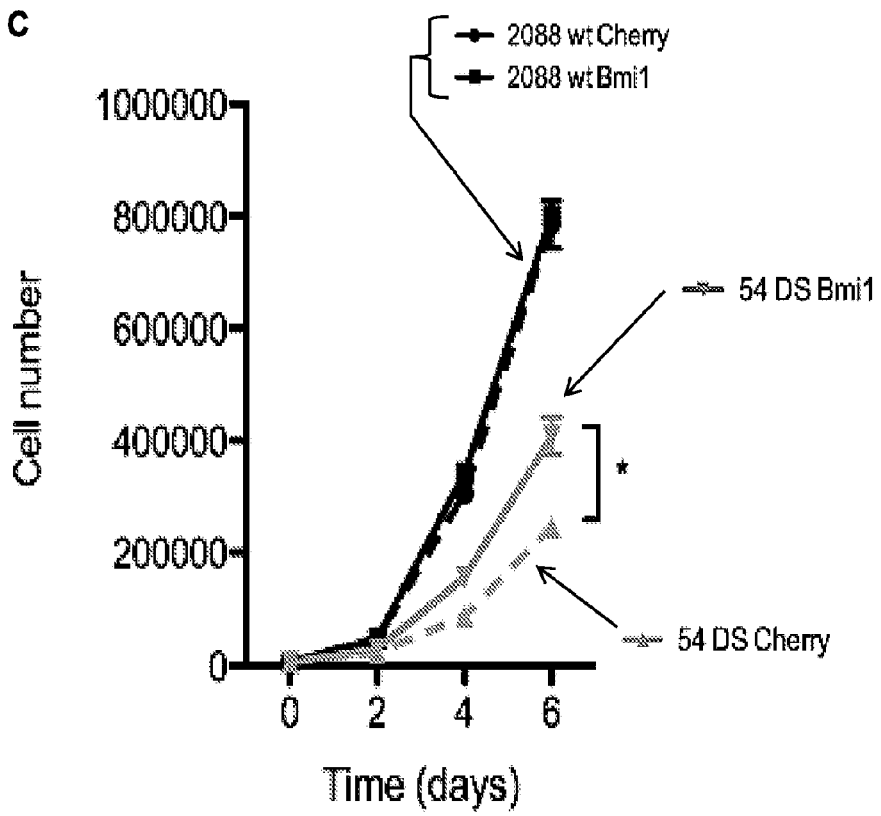
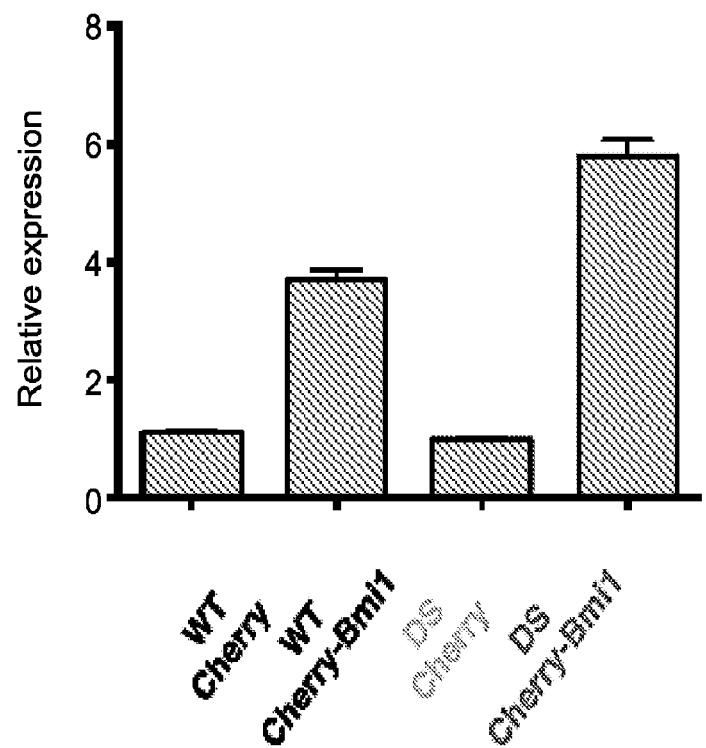

FIGURE 15
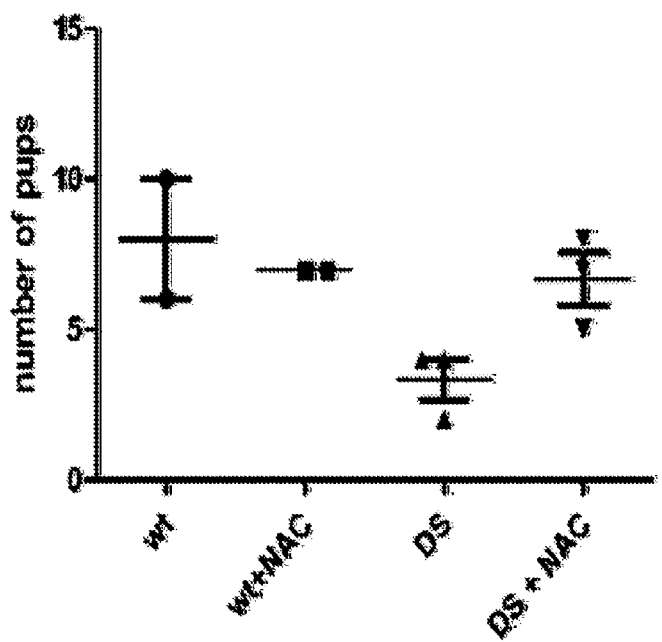
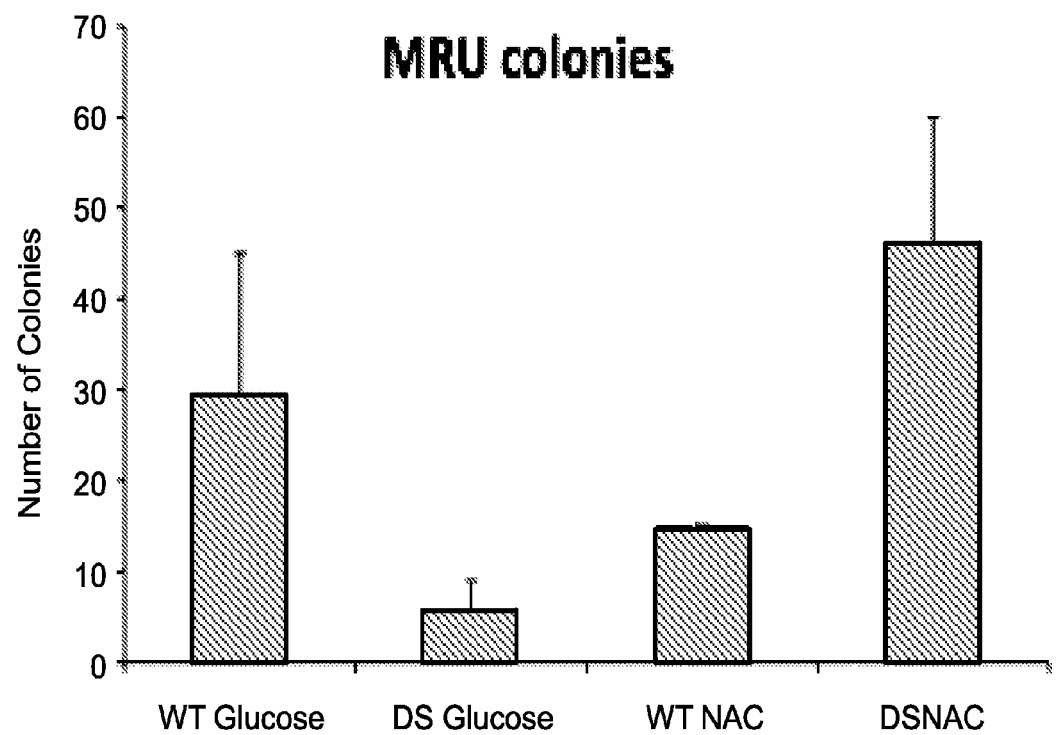

TARGETING CHROMATIN MODIFIERS FOR THE TREATMENT OF MEDICAL CONDITIONS

CROSS REFERENCE TO RELATED APPLICATIONS

Pursuant to 35 U.S.C. §119 (e), this application claims priority to the filing date of the U.S. Provisional Patent Application Ser. No. 61/788,795 filed Mar. 15, 2013; the disclosure of which are herein incorporated by reference.

GOVERNMENT RIGHTS

This invention was made with Government support under contract no. CA100225 awarded by the National Institutes of Health, and contract no. W81XWH-13-1-0281 awarded by the Department of Defense. The Government has certain rights in the invention.

FIELD OF THE INVENTION

This invention pertains to the use of chromatin modifiers in the treatment of medical conditions associated with a reduced rate of stem cell self-renewal or that will be responsive to an increased rate of stem cell self-renewal.

BACKGROUND OF THE INVENTION

Down's syndrome (DS) is one of the most common genetic abnormalities in humans and most often results from full or partial trisomy of chromosome 21. It is a complex clinical syndrome associated with higher risk of multiple pathological conditions, including heart problems, motor skills and cognitive deficits, a reduced incidence of solid tumors, and both early onset and higher incidence of aging-related phenomena such as Alzheimer's disease (Antonarakis, S. E., et al. Chromosome 21 and Down's syndrome: from genomics to pathophysiology. Nat. Rev. Genet. 5, 725-738 (2004); Yang, Q., et al. Mortality associated with Down's syndrome in the USA from 1983 to 1997: a population-based study. Lancet 359, 1019-1025 (2002); Satgé, D. et al. A tumor profile in Down's syndrome. Am. J. Med. Genet. 78, 207-216 (1998); Roth, G. et al. Premature aging in persons with Down's syndrome: MR findings. AJNR Am J Neuroradiol 17, 1283-1289 (1996); Carmeliet, G., et al. Cellular ageing of Alzheimer's disease and Down's syndrome cells in culture. Mutat. Res. 256, 221-231 (1991); Zigman, W. B. et al. Alzheimer's disease in Down's syndrome: neurobiology and risk. Ment Retard Dev Disabil Res Rev 13, 237-246 (2007)).

Down's syndrome is but one of many medical conditions that are associated with a reduction in the rate of tissue-specific stem cell self-renewal, and/or that will be treated by increasing the rate of tissue-specific stem cell self-renewal. What is need are better methods and therapeutics for alleviating the symptoms of these conditions. The present disclosure addresses these issues.

SUMMARY OF THE INVENTION

Methods and compositions are provided for the treatment of medical conditions associated with a reduced rate of stem cell self-renewal or that will be responsive to an increased rate of stem cell self-renewal. Aspects of the methods include inhibiting H2A deubiquitinating enzyme activity in cells, e.g. by administering an effective amount of an H2A deubiquitinating enzyme antagonist. Also provided are screens to identify therapeutics for the treatment of medical conditions associated with a reduced rate of stem cell self-renewal or that will be responsive to an increased rate of stem cell self-renewal.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 2. Effects of shRNAs targeting USP16 on Ts65Dn hematopoietic cells. A). Quantitative real-time PCR was used to measure expression of Usp16 mRNA levels in wildtype (black) and Ts65Dn (grey) $CD34^-CD150^+CD48^-$ KLS cells. Two independent probes show similar results. B) Immunofluorescence using a monoclonal antibody against the ubiquitinated form of H2A on Lys119 shows a decrease in the number of positive foci in Ts65Dn cells (bottom row) compared to wild type (upper row) $CD34^-CD150^+CD48^-$ KLS cells. The arrows indicate the foci in one representative picture. On the right, the number of observed ubiquitin H2A foci per cell (100 cells analyzed in two separated experiments). C) Quantitative real time PCR was used to verify the level of knockDown's achieved by means of lentiviral infection with two independent hairpins. USP16 expression is reduced to achieve level in Ts65Dn cells similar to that of wild type cells. D) KnockDown's of Usp16 by 2 independent shRNAs partially rescues the in vitro colony formation defects of Ts65Dn HSCs. The colony formation potential of single CD34⁻CD150⁺CD48⁻ KLS Ts65Dn cells transduced with control or two independent shRNAs targeting USP16 was evaluated one week after plating in Methocult. Note that both USP16 shRNAs, but not the control shRNA, enhance the ability of the Ts65Dn cells to form colonies. Experiments were repeated three times with similar results. E) Knock-Down's of USP16 by shRNA partially restores the engraftment potential of stem and progenitor cells. Two different doses of donor KLS cells were used in bone marrow transplantation experiments. The left panel shows the engraftment of Ts65Dn KLS transduced with shC (black line,) or shUSP16 hairpins (grey line). The right panel shows the calculated stem cell frequency of each transduced population (p=0.004, calculated using ELDA software, Walter-Eliza Hall bioinformatics). These experiments were performed twice with similar results, with a total of 14 mice per group. F) Secondary transplants of bone marrow cells. Five millions bone marrow cells derived from engrafted animals were transplanted in secondary recipients. Engraftment was evaluated every month. The graph shows the percentage of CD45.2⁺ donor cells two months after transplantation (p=0.0015). Experiment was repeated twice with several donor mice.

FIG. 9. HSCs in Ts65Dn mice have lower levels of H2A ubiquitination. A) Immunofluorescence studies using a monoclonal antibody against the ubiquitinated form of H2A on Lys119 show a decrease in the number of positive foci in MEF derived from Ts65Dn cells compared to wild type. On the left, the collective results for genotype. On the right, each dot represents a different cell and each column a different mouse. Hundred cells per group were analyzed and the experiment was repeated twice. B) Semiquatification of the overall H2AUb+ staining is decreased in Ts65Dn compared to wildtype MEFs. C) Western blot analyses of chromatin extracts from MEFs. H2AUb levels are decreased in Ts65Dn (quantification performed using ImageJ software). H2A Western blot was used to verify equal loading of extracts.

FIG. 10. Downregulation of USP16 improves engraftment of Ts65Dn KLS in primary and secondary transplants. A) Peripheral blood analyses, four months after bone marrow transplant, revealed multineage engraftment from Ts65 KLS infected with a shUSP16 hairpin. Representative FACS plots are shown. B) Two months after transplantation in secondary recipient, shC Ts65Dn bone marrow cells fail to engraft, while shUSP16 Ts65Dn cells show multilineage reconstitution. Representative FACS plots are shown.

FIG. 15. The effects of treatment with the free radical scavenger N-acetyl cysteine (Nac). A) N-acetyl cysteine (Nac) improves embryonic survival of Down's Syndrome fetuses after oral treatment of the mother with 10 ug/ml of N-acetyl cysteine administered in the drinking water. B) The treatment continued for 2 months after birth and showed a significant effect in the proliferation ability of breast epithelial cells.

DETAILED DESCRIPTION OF THE INVENTION

Figure 1:
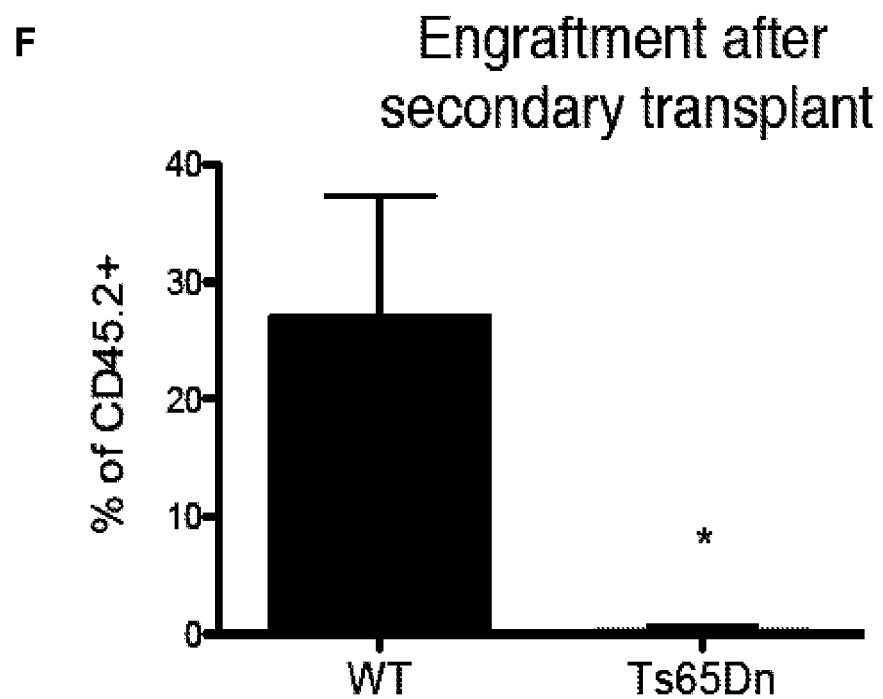
FIG. 1. Ts65Dn mice have defective hematopoietic stem cells (HSCs). A) A schematic diagram of mouse DS models is shown. Ts65Dn and Ts1 Cje both contain in trisomy a region of mouse Chromosome 16 homologous to human chromosome 21. Ts65Dn mice have 132 genes in trisomy, while Ts1 Cje mice have only a subset of those. B) Flow cytometry analysis of bone marrow from DS mouse models. Cells are gated on live KLS cells. The blue boxes show the frequency of KLS $CD150^+CD48^-$ cells (top row) or KLS $CD34^-Flt3^-$ cells (bottom row), which are highly enriched for HSCs. A representative analysis from each genotype is shown. These results were replicated at least four times with similar results. C) The percentage of $CD34^-CD150^+CD48^-$ KLS cells, highly enriched for quiescent stem cells, is shown in this graph. Results are the average of at least four mice analyzed by FACS per group. Ts65Dn mice present a significant decrease in the number of these cells ($p<0.005$). D) Colony formation assay from single $CD34^-CD150^+CD48^-$ KLS cells grown in Methocult. The number of colonies was scored after one week. Numbers are shown as the percentage of positive colonies on the number of plated cells. Experiment was repeated at least three times ($p<0.005$). E) Limiting dilution analysis of bone marrow from DS mouse models. The graph visually shows the estimated stem cell frequencies in different mice (data generated with ELDA software, Walter-Eliza Hall bioinformatics). Note that Ts65Dn mice, but not Ts1 Cje, have decreased frequency of HSCs. On the right, the upper panel shows the estimated frequency of HSCs, while the lower panel shows the calculated P-value for the pairwise test of differences (**$p<0.01$) Two independent experiments were performed, with a total of 15 mice per genotype. F) Secondary transplants of bone marrow cells. Five millions bone marrow cells derived from primary engrafted animals were transplanted in secondary recipients. Engraftment was evaluated by peripheral blood analyses every month. The graph shows the percentage of $CD45.2^+$ donor cells three months after transplantation ($p=0.0447$). Experiment was repeated twice with different donor mice.

Methods and compositions are provided for the treatment of medical conditions associated with a reduced rate of stem cell self-renewal or that will be responsive to an increased rate of stem cell self-renewal. Aspects of the methods include inhibiting H2A deubiquitinating enzyme activity in cells, e.g. by administering an effective amount of an H2A deubiquitinating enzyme antagonist. Also provided are screens to identify therapeutics for the treatment of medical conditions associated with a reduced rate of stem cell self-renewal or that will be responsive to an increased rate of stem cell self-renewal. These and other objects, advantages, and features of the invention will become apparent to those persons skilled in the art upon reading the details of the compositions and methods as more fully described below.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods and compositions are provided for the treatment of a medical condition that is associated with a reduced rate of stem cell self-renewal or that will be responsive to, i.e. be treated by, an increased rate of stem cell self-renewal. By a medical condition that is associated with a reduced rate of stem cell self-renewal or that will be responsive to an increased rate of stem cell self-renewal (i.e. the "subject medical condition"), it is meant a disease, disorder, or other medical condition in which the tissue manifesting the disease, disorder or other condition is deficient in somatic cells (e.g. the tissue-specific stem cells that gave rise to the tissue had a defect in proliferation or differentiation), or for which additional somatic cells may treat the condition (e.g. in a tissue that has suffered damage, e.g. in tissues having tissue-specific stem cells have become quiescent, e.g. in adult tissue). Examples of conditions that are associated with a reduced rate of stem cell self-renewal or that will be responsive to an increased rate of stem cell self-renewal include neurodevelopmental disorders, e.g. Down's Syndrome, fragile-X syndrome, autism; brain injury, e.g. chemotherapy or radiation-induced brain injury, traumatic brain injury; neurodegenerative diseases, e.g. Alzheimer's Disease, Parkinson's disease, ALS; aging-associated disorders, e.g. rheumatoid arthritis; muscle atrophy, e.g. muscle atrophy associated with diseases or disorders such as cancer, AIDS, congestive heart failure, COPD (chronic obstructive pulmonary disease), and renal failure; bone marrow deficiency; diseases requiring the regeneration of pancreatic cells, e.g. β islet cells, e.g. diabetes; diseases requiring liver regeneration, e.g. cirrhosis; conditions requiring skin regeneration, e.g. severe burns; and the like.

By "treatment", "treating" and the like it is generally meant obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. The terms "individual," "subject," "host," and "patient," are used interchangeably herein and refer to any mammalian subject for whom diagnosis, treatment, or therapy is desired, particularly humans.

In describing aspects of the invention, the subject compositions will be described first, followed by methods for their use.

Compositions

In some aspects of the invention, compositions are provided that comprise an antagonist of a histone deubiquitinating enzyme. By a deubiquitinating enzyme or "deubiquitinase" it is meant an enzyme that removes a covalently attached ubuiquitin from a protein. By a histone deubiquitinating enzyme, it is meant an enzyme that removes a covalently attached ubiquitin from histones, e.g. the H2A histone, the H2B histone. By an "H2A deubiquitinating enzyme" or "H2A deubiquitinase", it is meant an enzyme that removes a covalently attached ubiquitin from the histone H2A. Nonlimiting examples of H2A deubiquitinating enzymes include 2A-DUB/MYSM1, USP3, USP7, Ubp-M/

USP16, USP21, USP22, BAP1, and BRCC36 (BRCA-1 containing complex). By a "H2A deubiquitinating enzyme antagonist", it is meant any agent that reduces, suppresses, inhibits, antagonizes, etc. the activity of one or more H2A deubiquitinating enzymes in the cell.

In some embodiments, the subject composition comprises an antagonist of an H2A deubiquitinating enzyme. In certain embodiments, the H2A deubiquitinating enzyme is selected from the group consisting of 2A-DUB/MYSM1, USP3, USP7, Ubp-M/USP16, USP21, USP22, BAP1, and BRCA-1 containing complex (BRCC36). In certain embodiments, the H2A deubiquitinating enzyme is 2A-DUB/MYSM1. By "2A-DUB/MYSM1", it is meant the enzyme MYSM1 Myb-like, SWIRM and MPN domains 1, the sequence for which may be found at GenBank Accession No. NM_001085487.2. In certain embodiments, the H2A deubiquitinating enzyme is USP3. By "USP3" it is meant Ubiquitin Specific Peptidase 3, the sequence for which may be found at GenBank Accession Nos. NM_006537.3 and NM_001256702.1. In certain embodiments, the H2A deubiquitinating enzyme is USP7. By "USP7" it is meant Ubiquitin Specific Peptidase 7, the sequence for which may be found at GenBank Accession Nos. NM_003470.2, NM_001286457.1, and NM_001286458.1. In certain embodiments, the H2A deubiquitinating enzyme is Ubp-M/USP16. By "USP16" it is meant Ubiquitin Specific Peptidase 16, the sequence for which may be found at GenBank Accession Nos. NM_006447.2 (variant 1), NM_001001992.1 (variant 2), and NM_001032410.1 (variant 3). In certain embodiments, the H2A deubiquitinating enzyme is USP21. By "USP21" it is meant Ubiquitin Specific Peptidase 21, the sequence for which may be found at GenBank Accession Nos. NM_012475.4 and NM_001014443.2. In certain embodiments, the H2A deubiquitinating enzyme is USP22. By "USP22" it is meant Ubiquitin Specific Peptidase 22, the sequence for which may be found at GenBank Accession No. NM_015276.1. In certain embodiments, the H2A deubiquitinating antagonist inhibits BAP1. By BAP1 it is meant BRCA1 associated protein-1, the sequence for which may be found at GenBank Accession No. NM_004656.3.

As demonstrated in the working examples herein, H2A deubiquitinating enzyme s, e.g. the H2A deubiquitinating enzyme USP16, regulate stem cell proliferation and function in a number of tissues, including the hematopoietic stem cell compartment, the neural stem cell compartment, and the mammary gland. As such, inhibiting H2A deubiquitinating activity in stem and progenitor cells by providing an antagonist of, for example, USP16, will promote the proliferation of neural stem and progenitor cells, which will increase the production of new neurons and improve nervous system function in individuals with neurodevelopmental disorders and neurodegenerative disease; will promote the proliferation of hematopoietic stem and progenitor cells, which will increase the production of hematopoietic cells and improve immune system function, and will promote the proliferation of mammary epithelial cells; and will promote the growth of the mammary epithelium.

Any agent that antagonizes an H2A deubiquitinating enzyme, e.g. USP16, in stem and progenitor cells, e.g. as known in the art, as described herein, or as identified using the screening methods described herein, may be employed in the subject compositions. The subject agent may act by, for example, reduce the relative amount of the deubiquitinating enzyme in the cell, block the active site of deubiquitination on the histone, promote the localization of the deubiquitinating enzyme to the cell cytoplasm, promote the ubiquitination of the H2A histone, etc. For example, the subject agent may reduce the activity of USP16 by, for example, reducing the relative amount of USP16 protein in the cell, e.g. the subject agent may be a nucleic acid inhibitor that is specific for USP16, i.e., it is a USP16-specific nucleic acid inhibitor, for example, an antisense RNA, antagomir RNA, shRNA, siRNA, CRISPRi, etc. By "specific", "specific binding," "specifically bind," and the like, it is meant the ability of a binding agent, e.g. nucleic acid, polypeptide, antibody, etc., to preferentially bind directly to a target molecule relative to other molecules or moieties in the cell. In certain embodiments, the affinity between the binding agent and the target to which it specifically binds when they are specifically bound to each other in a binding complex is characterized by a KD (dissociation constant) of less than $10^{-6}$ M, less than 10-7 M, less than 10-8 M, less than $10^{-9}$ M, less than $10^{-19}$ M, less than $10^{-11}$ M, less than $10^{-12}$ M, less than $10^{-13}$ M, less than $10^{-14}$ M, or less than $10^{-15}$ M.

Agents suitable for use as antagonists of an H2A deubiquitinating enzyme in the subject compositions include small molecule compounds, e.g. a naturally occurring or synthetic small molecule compound. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992). Small molecule compounds can be provided directly to the medium in which the cells are being cultured, for example as a solution in DMSO or other solvent.

Agents suitable for use as antagonists of an H2A deubiquitinating enzyme in the subject compositions also include nucleic acids, for example, nucleic acids that encode siRNA, shRNA or antisense molecules, or nucleic acids that encode polypeptides. Many vectors useful for transferring nucleic acids into target cells are available. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc.

Vectors may be provided directly to the subject cells. In other words, the cells are contacted with vectors comprising the nucleic acid of interest such that the vectors are taken up by the cells. Methods for contacting cells with nucleic acid vectors, such as electroporation, calcium chloride transfection, and lipofection, are well known in the art.

Alternatively, the nucleic acid of interest may be provided to the subject cells via a virus. In other words, the cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) *Mol. Cell. Biol.* 5:431-437); PA317 (Miller et al. (1986) *Mol. Cell. Biol.* 6:2895-2902); GRIP (Danos et al. (1988) *PNAS* 85:6460-6464). Retroviruses packaged with xenotropic envelope protein, e.g. AKR env, are capable of infecting most mammalian cell types, except murine cells. The appropriate packaging cell line may be used to ensure that the subject CD33+ differentiated somatic cells are targeted by the packaged viral particles. Methods of introducing the retroviral vectors comprising the subject nucleic acid into packaging cell lines and of collecting the viral particles that are generated by the packaging lines are well known in the art.

Vectors used for providing nucleic acid of interest to the subject cells will typically comprise suitable promoters for driving the expression, that is, transcriptional activation, of the nucleic acid of interest. In other words, the nucleic acid of interest will be operably linked to a promoter. This may include ubiquitously acting promoters, for example, the CMV-b-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing the subject nucleic acids to the cells may include genes that must later be removed, e.g. using a recombinase system such as Cre/Lox, or the cells that express them destroyed, e.g. by including genes that allow selective toxicity such as herpesvirus TK, bcl-xs, etc Agents suitable for use as antagonists of an H2A deubiquitinating enzyme in the subject compositions also include polypeptides. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like.

If the polypeptide agent is to inhibit deubiquitinatase activity intracellularly, the polypeptide may comprise the polypeptide sequences of interest fused to a polypeptide permeant domain. A number of permeant domains are known in the art and may be used in the non-integrating polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

If the polypeptide agent is to inhibit deubiquitinatase activity extracellularly, the polypeptide may be formulated for improved stability. For example, the peptides may be PEGylated, where the polyethyleneoxy group provides for enhanced lifetime in the blood stream. The polypeptide may be fused to another polypeptide to provide for added functionality, e.g. to increase the in vivo stability. Generally such fusion partners are a stable plasma protein, which may, for example, extend the in vivo plasma half-life of the polypeptide when present as a fusion, in particular wherein such a stable plasma protein is an immunoglobulin constant domain. In most cases where the stable plasma protein is normally found in a multimeric form, e.g., immunoglobulins or lipoproteins, in which the same or different polypeptide chains are normally disulfide and/or noncovalently bound to form an assembled multichain polypeptide, the fusions herein containing the polypeptide also will be produced and employed as a multimer having substantially the same structure as the stable plasma protein precursor. These multimers will be homogeneous with respect to the polypeptide agent they comprise, or they may contain more than one polypeptide agent.

Stable plasma proteins are proteins which typically exhibit in their native environment an extended half-life in the circulation, i.e. greater than about 20 hours. Examples of suitable stable plasma proteins are immunoglobulins, albumin, lipoproteins, apolipoproteins and transferrin. The polypeptide agent typically is fused to the plasma protein, e.g. IgG at the N-terminus of the plasma protein or fragment thereof which is capable of conferring an extended half-life upon the polypeptide. Increases of greater than about 100% on the plasma half-life of the polypeptide are satisfactory. Ordinarily, the polypeptide is fused C-terminally to the N-terminus of the constant region of immunoglobulins in place of the variable region(s) thereof, however N-terminal fusions may also find use. Typically, such fusions retain at least functionally active hinge, CH2 and CH3 domains of the constant region of an immunoglobulin heavy chain, which heavy chains may include IgG1, IgG2a, IgG2b, IgG3, IgG4, IgA, IgM, IgE, and IgD, usually one or a combination of proteins in the IgG class. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, the polypeptides may be synthesized according to known methods.

The site at which the fusion is made may be selected in order to optimize the biological activity, secretion or binding characteristics of the polypeptide. The optimal site will be determined by routine experimentation.

In some embodiments the hybrid immunoglobulins are assembled as monomers, or hetero- or homo-multimers, and particularly as dimers or tetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of basic four-chain units held together by disulfide bonds. IgA immunoglobulin, and occasionally IgG immunoglobulin, may also exist in a multimeric form in serum. In the case of multimers, each four chain unit may be the same or different.

The polypeptide agent for use in the subject methods may be produced from eukaryotic produced by prokaryotic cells, it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The subject polypeptides may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Another example of polypeptide agents suitable for use as antagonists of an H2A deubiquitinating enzyme in the subject compositions are antibodies. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." The term "antibody" herein is used in the broadest sense and specifically covers intact antibodies, monoclonal antibodies, polyclonal antibodies, multispecific antibodies (e.g. bispecific antibodies) formed from at least two intact antibodies, and antibody fragments, so long as they exhibit the desired biological activity. Antibodies are typically provided in the media in which the cells are cultured.

Agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents that are H2A deubiquitinating enzyme antagonists may be readily validated as such by any of a number of convenient methods in the art. For example, the amount of H2AK119 ubiquitin mark at the Ink4a/Arf locus in cells can be measured, wherein an increase in ubiquitin mark following treatment with agent indicates that the agent is a USP16 antagonist. As another example, the amount of Ink4a RNA or protein in cells can be assessed, where a decrease in the amount of Ink4a RNA/protein following treatment with agent indicates that the agent is a USP16 antagonist. As a third example, the proliferation rate of cells, e.g. Down's syndrome fibroblasts, e.g. fibroblasts from the Ts65Dn mouse, may be determined, where an increase in proliferation following treatment with the agent indicates that the agent is a H2A deubiquitinating enzyme antagonist.

For inclusion in a medicament, the subject agent may be obtained from a suitable commercial source. As a general proposition, the total pharmaceutically effective amount of the subject agent administered parenterally per dose will be in a range that can be measured by a dose response curve.

Preparations of subject agent to be used for therapeutic administration must be sterile. Sterility is readily accomplished by filtration through sterile filtration membranes (e.g., 0.2 μm membranes). Therapeutic compositions generally are placed into a container having a sterile access port, for example, an intravenous solution bag or vial having a stopper pierceable by a hypodermic injection needle. The subject agent-based therapies may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

The subject agent can be incorporated into a variety of formulations. More particularly, the subject agent of the present invention can be formulated into pharmaceutical compositions by combination with appropriate pharmaceutically acceptable carriers or diluents.

Pharmaceutical preparations are compositions that include one or more targeted subject agents present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the subject agent can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic compositions of the invention when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of therapeutics agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversably affixed (see e.g. US Application Nos. 20080081064 and 20090196903, incorporated herein by reference).

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required.

Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

The calculation of the effective amount or effective dose of agent to be administered is within the skill of one of ordinary skill in the art, and will be routine to those persons skilled in the art. Needless to say, the final amount to be administered will be dependent upon the route of administration and upon the nature of the disorder or condition that is to be treated.

Methods

In practicing the subject methods, the subject antagonist of an H2A deubiquitinating enzyme is contacted with a stem or progenitor cell. The term "stem cell" is used herein to refer to a mammalian cell that has the ability both to self renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further Down's the developmental pathway than the cell it is being compared with. Thus, pluripotent stem cells (described below) can differentiate into further restricted stem cells (e.g., Epiblast stem cells (described below), mesodermal stem cells, mesenchymal stem cells, and the like), which in turn can differentiate into cells that are further restricted (e.g., cardiomyocyte progenitors, neural progenitors, and the like), which can differentiate into end-stage cells (i.e., terminally differentiated cells, e.g., neurons, skeletal muscle cells, cardiomyocytes, adipocytes, osteoblasts, and the like), which play a characteristic role in a certain tissue type, and may or may not retain the capacity to proliferate further. Different types of stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to particular types of differentiated progeny.

When a stem cell divides symmetrically, both resulting daughter cells are equivalent. For example, a stem cell may undergo a self-renewing symmetric division in which both resulting daughter cells are stem cells with an equal amount of differentiation potential as the mother cell. However, a symmetric division is not necessarily a self-renewing division because both resulting daughter cells may instead be differentiated relative to the mother cell. When a stem cell divides asymmetrically, the resulting daughter cells are different than one another. For example, if a stem cell undergoes a self-renewing asymmetric division, then one of the resulting daughter cells is a stem cell with the same amount of differentiation potential as the mother cell while the other daughter cell is differentiated relative to the mother cell (e.g., a more lineage restricted progenitor cell, a terminally differentiated cell, etc.). A stem cell may directly differentiate (i.e., without dividing), or may instead produce a differentiated cell type through an asymmetric or symmetric cell division.

Stem cells (i.e., cell populations) of interest in the present disclosure include pluripotent stem cells (PSCs, i.e., a PSC population). The term "pluripotent stem cell" or "PSC" is used herein to mean a stem cell capable of self-renewal and of producing all cell types of the organism (i.e., it is pluripotent). Therefore, a PSC can give rise to cells of all germ layers of the organism (e.g., the endoderm, mesoderm, and ectoderm). Pluripotent stem cells exist in two states: (i) a "naïve" state, which is epitomized by mouse embryonic stem cells (ESCs, described in more detail below) and (ii) a "primed" state, which is epitomized by the developmentally more advanced mouse epiblast stem cells (EpiSCs, described in more detail below). In the naive state, the PSC genome has an unusual open conformation and possesses a minimum of repressive epigenetic marks. In contrast, cells in the primed state have activated the epigenetic machinery that supports differentiation towards the cell types of the embryo. The transition from naive to primed pluripotency therefore represents a pivotal event in cellular differentiation. For more details regarding the naïve and primed states, see, for example, Nichols and Smith, Cell Stem Cell. 2009 Jun. 5; 4(6):487-92: Naive and primed pluripotent states.

Stem cells of interest in the present disclosure also include tissue-specific stem cells, e.g. Epiblast stem cells, mesodermal stem cells, mesenchymal stem cells, neural stem cells. The term "tissue-specific stem cell" is used herein to mean a cell capable of self-renewal but having a restricted potential, i.e. it cannot give rise to all cell types in the body without some manipulation by the hand of man. Tissue specific stem cells can give rise to the cells of the tissue from which they are derived. For example, neural stem cells can give rise to neurons, oligodendrocytes, and astrocytes. Tissue specific stem cells can in turn can differentiate into proliferating cells that are further restricted (e.g., cardiomyocyte progenitors, neural progenitors, and the like), which can differentiate into end-stage cells (i.e., terminally differentiated cells, e.g., neurons, skeletal muscle cells, cardiomyocytes, adipocytes, osteoblasts, and the like), Cells of interest in the present disclosure also include progenitor cells. The term "progenitor cell" is used herein to refer to a type of stem cell that typically does not have extensive self-renewal capacity (i.e., the number of self-renewing divisions is limited), and often can only generate a limited number of differentiated cell types (e.g., a specific subset of cells found in the tissue from which they derive). Thus, a progenitor cell is differentiated relative to the tissue-specific stem cell that gave rise to it, but can also give rise to cells that are further differentiated (e.g., terminally differentiated cells). For the purposes of the present invention, progenitor cells are those cells that are committed to a lineage of interest (e.g., a cardiomyocyte progenitor, a neural progenitor, etc.), but have not yet differentiated into a mature cell (e.g., a cardiomyocyte, a neuron, etc.).

The stem or progenitor cells contacted in the subject methods may be from any mammalian species, e.g. murine, rodent, canine, feline, equine, bovine, ovine, primate, human, etc. For in vitro studies, cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvest from an individual by any convenient method. For example, cells, e.g. blood cells, e.g. hematopoietic stem cells or hematopoietic progenitor cells, may be harvested by apheresis, leukocytapheresis, density gradient separation, bone marrow biopsy, fetal liver biopsy, cord blood, etc. As another example, cells from solid tissues, e.g. neuronal stem cell or progenitor cells, may be harvested by biopsy, e.g. from the stem cell niche, e.g. the subventricular zone. An appropriate solution may be used for dispersion or suspension of the harvested cells. Such solution will generally be a balanced salt solution, e.g. normal saline, PBS, Hank's balanced salt solution, Iscoves, etc., conveniently supplemented with fetal calf serum and/or other factors, e.g. B27, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

Contacting the cells with the subject compositions in vitro may occur in any culture media and under any culture conditions that promote the survival of the cells. For example, cells may be suspended in any appropriate nutrient medium that is convenient, such as Iscove's modified DMEM or RPMI 1640, supplemented with serum, e.g. fetal calf serum, heat inactivated goat serum (about 5-10%) etc., or synthetic reagents that support growth, e.g. B27, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Examples of mediums and reagents that find particular use in the culturing of neurons may be found in the Example section below.

In practicing the subject methods, the subject composition may be provided to the cells one or more times, e.g. one time, twice, three times, or more than three times, and the cells allowed to incubate with the subject agent for some amount of time following each contacting event e.g. 16-24 hours, after which time the media is replaced with fresh media and the cells are cultured further.

As discussed above, the subject methods and compositions find use in treating medical conditions that are associated with a reduced rate of stem cell self-renewal or that will be responsive to an increased rate of stem cell self-renewal. In these in vivo embodiments, the subject agent is administered directly to the individual. Any mammal may be administered with the subject agent to treat the subject medical condition, e.g. murine, rodent, canine, feline, equine, bovine, ovine, primate, human, etc. The subject agent may be administered by any of a number of well-known methods for the administration of polypeptides, peptides, small molecules or nucleic acids to a subject, e.g. as described herein or known in the art.

Contacting the cells with the subject compositions in vivo may be achieved by administration of the subject composition to the individual via any convenient route. For example, the subject composition may be administered orally, buccally, rectally, parenterally, intraperitoneally, intradermally, transdermally, intracheally, etc. The subject composition may be administered locally or systemically, e.g. intraventricularly, into the bone marrow, etc. The active agent may be systemic after administration or may be localized, e.g. by the use of regional administration, intramural administration, or use of an implant that acts to retain the active dose at the site of implantation.

In practicing the subject methods, an effective amount of the H2A deubiquitinating enzyme antagonist is typically provided. Biochemically speaking, an "effective amount" or "effective dose" of the subject agent is an amount of agent that will inhibit, antagonize, decrease, reduce, or suppress the deubiquitinating activity of the H2A deubiquitinating enzyme by about 20% or more, e.g. by 30% or more, by 40% or more, or by 50% or more, in some instances by 60% or more, by 70% or more, by 80% or more, or by 90% or more, in some cases by about 100%, i.e. to negligible amounts. Any convenient method for measuring the extent of histone ubiquitination, e.g. as known in the art or as described herein, may be used to determine an effective amount.

In a clinical sense, an effective amount, or dose, of the H2A deubiquitinating enzyme antagonist is an amount of agent that, when administered for a suitable period of time, usually at least about one week, and maybe about two weeks, or more, up to a period of about 4 weeks, 8 weeks, or longer will evidence an alteration in the symptoms associated with the medical condition, e.g. the cognitive impairment in an individual having a neurodevelopmental disorder, neurodegenerative disease, or brain injury; cognitive impairment and autoimmunity associated with cellular senescence in an aging individual; muscle atrophy associated with, e.g. cancer, AIDS, congestive heart failure, COPD (chronic obstructive pulmonary disease), or renal failure; immunodeficiency associated with a bone marrow deficiency; insulin deficiency associated with pancreatic diseases that require pancreatic cell regeneration, e.g., diabetes; jaundice, fatigue, weakness associated with liver failure; wound healing following a severe burn, etc. Methods for measuring improved tissue development and/or function in, for example, the CNS, the hematopoietic compartment, the pancreas, the liver, the lung, etc. are well known in the art, any of which may be used to determine an effective dose and to determine that an individual is treated for the medical condition by the administration of the subject composition.

It will be understood by those of skill in the art that an initial dose may be administered for such periods of time, followed by maintenance doses, which, in some cases, will be at a reduced dosage.

For example, an effective dose is the dose that when administered for a suitable period of time, usually at least about one week, and maybe about two weeks, or more, up to a period of about 4 weeks, 8 weeks, or longer will slow e.g. by about 20% or more, e.g. by 30% or more, by 40% or more, or by 50% or more, in some instances by 60% or more, by 70% or more, by 80% or more, or by 90% or more, or halt cognitive decline, i.e. stabilize the cognitive abilities, in a patient suffering from a neurodevelopmental disease such as Down's Syndrome, a neurodegenerative disease such as Alzheimer's Disease, or a cognitive impairment associated with a brain injury. In some embodiments, an effective amount or dose may not only slow or halt the progression of the disease condition but may also induce the reversal of the condition. For example, an effective dose is the dose that when administered for a suitable period of time, usually at least about one week, and maybe about two weeks, or more, up to a period of about 4 weeks, 8 weeks, or longer will improve the cognition in an individual with, for example, a neurodevelopmental disease such as Down's Syndrome, a neurodegenerative disease such as Alzheimer's Disease, or a cognitive impairment associated with a brain injury by, for example 1.5-fold, 2-fold, 3-fold, 4-fold, 5-fold, in some instances 6-fold, 7-fold, 8-fold, 9-fold, or 10-fold or more. An improvement in cognition may be observed as, for example, an improvement in memory. Improvements in memory may be readily assessed using any convenient method known in the art, e.g., by assaying retrieval-related brain activity (Buchmann A, et al. (2008) Prion protein M129V polymorphism affects retrieval-related brain activity. Neuropsychologia. 46(9):2389-402) or, e.g., by imaging brain tissue by functional magnetic resonance imaging (fMRI) following repetition priming with familiar and unfamiliar objects (Soldan A, et al. (2008) Global familiarity of visual stimuli affects repetition-related neural plasticity but not repetition priming. Neuroimage. 39(1):515-26; Soldan A, et al. (2008) Aging does not affect brain patterns of repetition effects associated with perceptual priming of novel objects. J Cogn Neurosci. 20(10):1762-76). Other examples include tests such as cognition tests and IQ test for measuring cognitive ability, e.g. attention and concentration, the ability to learn complex tasks and concepts, memory, information processing, visuospatial function, the ability to produce and understanding language, the ability to solve problems and make decisions, and the ability to perform executive functions; for example, the General Practitioner Assessment of Cognition (GPCOG) test, the Memory Impairment Screen, the Mini Mental State Examination (MMSE), the California Verbal Learning Test, Second Edition, Short Form, for memory, the Delis-Kaplan Executive Functioning System test, and the like.

In some instances, the cells may be contacted with more than one agent. For example, the subject composition may be provided to cells in vitro in conjunction with a second agent, or the subject composition may be provided to cells in vivo in conjunction with a second agent. In cases in which two or more different subject agents are provided to the cell, i.e. a cocktail of agents, the agents may be provided simultaneously, e.g. as two polypeptides delivered simultaneously, as two nucleic acid vectors delivered simultaneously, as a single nucleic acid vector comprising the coding sequences for two polypeptides, as two small molecules provided simultaneously, etc. Alternatively, they may be provided consecutively, e.g. the first subject agent being provided first, followed by the second subject agent, etc. or vice versa.

In some embodiments, the subject composition may be provided in conjunction with a second agent. For example, In some embodiments, the subject composition may be provided in conjunction with an agent that promotes stem cell self-renewal in a cell. In some embodiments, the subject composition may be provided in conjunction with an agent that promotes histone ubiquitination in a cell, for example, for example, an agonist of a histone ubiquitinating enzyme. In some embodiments, the subject composition may be provided in conjunction with an agent that has been demonstrated in the art to treat the subject medical condition. For example, a number of agents have been shown to have some efficacy in treating the cognitive symptoms of Alzheimer's disease (e.g., memory loss, confusion, and problems with thinking and reasoning), e.g. cholinesterase inhibitors (e.g. Donepezil, Rivastigmine, Galantamine, Tacrine), Memantine, and Vitamin E. As another example, a number of agents have been shown to have some efficacy in treating behavioral or psychiatric symptoms of Alzheimer's Disease, e.g. citalopram (Celexa), fluoxetine (Prozac), paroxeine (Paxil), sertraline (Zoloft), trazodone (Desyrel), lorazepam (Ativan), oxazepam (Serax), aripiprazole (Abilify), clozapine (Clozaril), haloperidol (Haldol), olanzapine (Zyprexa), quetiapine (Seroquel), risperidone (Risperdal), and ziprasidone (Geodon).

In some embodiments, the subject composition may be provided in conjunction with an antioxidant. By an "antioxidant" it is meant a molecule that inhibits the oxidation of molecules by free radicals. By oxidation it is meant a chemical reaction that transfers electrons or hydrogen from a substance to an oxidizing agent. Oxidation reactions can produce free radical intermediates, which in turn transfer electrons or hydrogen to cellular molecules, e.g. DNA, proteins, lipids, etc., causing cell damage or cell death. Antioxidants prevent the start of these chain reactions and terminate these chain reactions by removing free radicals and free radical intermediates, thereby becoming oxidized themselves. In other words, antioxidants are free radical scavengers. As such, antioxidants are often reducing agents such as thiols, ascorbic acid, or polyphenols. Examples of antioxidants include beta-carotene, lutein, lycopene, bilirubin, selenium, zinc, vitamin A, vitamin C (ascorbic acid), vitamin E ($\alpha$-tocopherol), uric acid, nitric oxide, nitroxide, pyruvate, catalase, superoxide dismutase, glutathione peroxidases, N-acetyl cysteine, ubiquinol (coenzyme Q), naringenin. tirilazad mesylate, ebselen, edaravone, NXY-059

In some embodiments, the subject composition is provided before the second agent. In some embodiments, the subject composition is provided after the second agent. In some embodiments, the subject composition is provided concurrently with the second agent. In certain such embodiments, the subject composition comprises one or more of these additional agents.

In some aspects of the subject methods, the method further comprises the step of identify an individual in need of treatment by the subject methods, e.g diagnosing an individual as having a medical condition associated with a reduced rate of stem cell self-renewal or that will be responsive to an increased rate of stem cell self-renewal, e.g. a neurodevelopmental disorder, e.g. Down's Syndrome, fragile-X syndrome, autism; a brain injury, e.g. chemotherapy or radiation-induced brain injury, traumatic brain injury; a neurodegenerative disease, e.g. Alzheimer's Disease, Parkinson's disease, ALS; aging-associated disorders, e.g. rheumatoid arthritis; muscle atrophy, e.g. muscle atrophy associated with a disease or disorder such as cancer, AIDS, congestive heart failure, COPD (chronic obstructive pulmonary disease), or renal failure; bone marrow deficiency; diseases requiring the regeneration of pancreatic cells, e.g. β islet cells, e.g. diabetes; diseases requiring liver regeneration, e.g. cirrhosis; conditions requiring skin regeneration, e.g. severe burns; and the like.

Methods for measuring symptoms associated with such medical conditions are well known in the art, any of which may be used to identify the individual for treatment by the subject methods. For example, measuring a cognitive impairment may include administering a standardized learning task or IQ test, and comparing the results of the task/test with a reference, e.g. the results of the test at an earlier time in the individual's life, or the results of the test from a healthy, i.e. non-affected, individual. Cognition tests and IQ test for measuring cognitive ability and cognitive impairment, e.g. attention and concentration, the ability to learn complex tasks and concepts, memory, information processing, visuospatial function, the ability to produce and understanding language, the ability to solve problems and make decisions, and the ability to perform executive functions, are well known in the art.

In some aspects of the subject methods, the method further comprises the step of measuring the symptoms associated with the medical condition after treatment, e.g. using the methods described herein or known in the art; and detecting a decrease in the symptoms after treatment as compared to before the subject composition was administered. In some instances, the determination is made by comparing the results of the assessment to the results of the assessment performed on the same individual at an earlier time, e.g. 1 week earlier, 2 weeks earlier, 1 month earlier, 2 months earlier, 3 months earlier, 6 months earlier, 9 months earlier, 1 year earlier, 2 years earlier, 5 years earlier, or 10 years earlier, or more. In other instances, the determination is made by comparing the results of the assessment to the results of the assessment performed on a reference individual, e.g. an unaffected individual.

Utility

The subject methods and compositions find a number of uses in medical treatment and in research. For example, the subject methods and compositions may be used in vivo in the treatment of an individual having a medical condition that is associated with a reduced rate of stem cell self-renewal or that will be responsive to an increased rate of stem cell self-renewal. As a second example, the subject methods and compositions may be used in in vitro screens to identify new therapies for medical conditions that are associated with a reduced rate of stem cell self-renewal or that will be responsive to an increased rate of stem cell self-renewal.

By "treatment", "treating" and the like it is generally meant obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. The terms "individual," "subject," "host," and "patient," are used interchangeably herein and refer to any mammalian subject for whom diagnosis, treatment, or therapy is desired, particularly humans.

As used herein, a medical condition associated with a reduced rate of stem cell self-renewal or that will be responsive to an increased rate of stem cell self-renewal (i.e., the "subject condition") generally includes a disease, disorder, or other medical condition in which the tissue manifesting the disease, disorder or other condition is deficient in somatic cells (e.g. the tissue-specific stem cells that gave rise to the tissue had a defect in proliferation or differentiation), or for which additional somatic cells may treat the condition (e.g. in a tissue that has suffered damage, e.g. in tissues having tissue-specific stem cells have become quiescent, e.g. in adult tissue). These include, for example, neurodevelopmental disorders, e.g. Down's Syndrome, fragile-X syndrome, autism; brain injury, e.g. chemotherapy or radiation-induced brain injury, traumatic brain injury; neurodegenerative diseases, e.g. Alzheimer's Disease, Parkinson's disease, ALS; aging-associated disorders, e.g. rheumatoid arthritis; muscle atrophy associated with conditions such as, e.g., cancer, AIDS, congestive heart failure, COPD, and renal failure; bone marrow deficiency; diseases requiring the regeneration of pancreatic cells, e.g. β islet cells, e.g. diabetes; diseases requiring liver regeneration, e.g. cirrhosis; conditions requiring skin regeneration, e.g. severe burns; and the like.

For example, the medical condition may be a neurodevelopmental disorder, a brain injury, a neurodegenerative disease, or general aging. In such instances, the medical condition includes symptoms of reduced cognitive function. By "cognition" it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). Cognition is a faculty for the processing of information, applying knowledge, and changing preferences. By "cognitive plasticity" it is meant the ability to learn, e.g., the ability to learn complex tasks and concepts, analogous to the ability to learn of an organism that is undifferentiated such as a newborn or juvenile, e.g., a human from the time of birth to pre-pubertal age of about 10 years. By "cognitive decline", it is meant a progressive decrease in cognition, as evidenced by, for example, a decline in one or more of, e.g., attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "an impairment in cognitive ability", "reduced cognitive function", and "cognitive impairment", it is meant an impairment in cognition relative to a healthy individual, e.g. an age-matched healthy individual, or relative to the ability of the individual at an earlier point in time, e.g. 2 weeks, 1 month, 2 months, 3 months, 6 months, 1 year, 2 years, 5 years, or 10 years or more previously.

In some instances, treatment by the subject methods or using the subject compositions stabilizes the cognitive abilities of the individual having the subject condition. For example, the progression of cognitive decline in an individual suffering from the subject condition is halted following treatment by the disclosed methods. In other words, no (further) cognitive impairment is observed. In some instances, treatment by methods of the present disclosure reduces, or reverses, cognitive impairment, e.g. as observed by improving cognitive abilities in an individual suffering from cognitive decline associated with the subject condition. In other words, the cognitive abilities of the individual suffering from cognitive decline following treatment by the disclosed methods are better than prior to treatment by the disclosed methods, i.e. they improve upon treatment. In some instances, treatment by methods of the present disclosure abrogates cognitive impairment. In other words, the cognitive abilities of the individual suffering from cognitive decline associated with the subject condition are restored to the level experienced by the individual at an earlier age following treatment by the disclosed methods, e.g. as evidenced by improved cognitive abilities in an individual suffering from the cognitive decline associated with the subject condition.

In some embodiments, the method comprises identifying an individual that has reduced cognitive function or is experiencing cognitive decline. In some embodiments, the method further comprises measuring memory or cognition prior to administering the agent and after administering the agent, wherein memory or cognition after administering the agent is improved relative to memory or cognition prior to administering the agent. Any convenient method known in the art or described herein for measuring cognitive function may be used to identify an individual in need of treatment by the subject methods and/or to measure the cognitive stabilization or improvement in an individual during/after treatment with the subject methods. These include, for example, administering a standardized learning task or IQ test to the individual, and comparing the results of the task/test with a reference. In some instances, the reference may be the results of the task/test performed by one or more age-matched individuals that either experience reduced cognitive function (i.e. positive controls) or do not experience reduced cognitive function (i.e. negative controls). In some instances, the reference may be the results of the task/test performed by the same individual at an earlier age, e.g. 1 week earlier, 1 month earlier, 3 months earlier, 6 months earlier, 9 months earlier, and the like, for example to determine if the individual is suffering from cognitive decline.

Screens

In some aspects of the invention, methods are provided for screening a candidate agent for the ability to treat an individual having a condition associated with a reduced rate of stem cell self-renewal or that will be responsive to an increased rate of stem cell self-renewal, e.g., for use in the treatment methods described herein. To this end, it has been shown herein that USP16 deubiquitinase activity reduces stem cell proliferation and function. Accordingly, screening for candidate agents that reduce USP16 deubiquitinase activity should identify agents that will be useful in promoting stem cell proliferation, and more particularly, neural stem cell proliferation and neurogenesis, which will, in turn, treat the symptoms of conditions associated with a reduced rate of stem cell self-renewal or that will be responsive to an increased rate of stem cell self-renewal.

For example, in screening assays for biologically active agents, cells expressing USP16 are contacted with a candidate agent of interest and the effect of the candidate agent on the cell is assessed by monitoring one or more output parameters. Parameters are quantifiable components of cells, particularly components that can be accurately measured, desirably in a high throughput system. A parameter can be any cell component or cell product including cell surface determinant, receptor, protein or conformational or post-translational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. Thus, for example, one such method may comprise contacting a cell that expresses USP16 with a candidate agent; and comparing the parameter to the parameter in a cell that expresses USP16 but was not contacted with the candidate agent, wherein a difference in the parameter in the cell contacted with the candidate agent indicates that the candidate agent will treat the symptoms of with the condition associated with a reduced rate of stem cell self-renewal or that will be responsive to an increased rate of stem cell self-renewal.

One example of a parameter that may be quantified when screening candidate agents to identify those that may be used as therapeutics for the treatment of neurodevelopmental disorder or a neurodegenerative disease would be USP16 deubiquitinase activity. USP16 deubiquitinase activity may be measured by any convenient method, e.g. as described herein or as known in the art. For example, USP16 deubiquitinase activity may be measured by assessing H2A ubiquitination, wherein an increase in the amount of H2A ubiquitination as compared to the amount of H2A ubiquitination in a cell not contacted with candidate agent indicates that the candidate agent will treat an individual having a neurodevelopmental disorder or a neurodegenerative disease. As another example, USP16 deubiquitinase activity may be measured by measuring the amount of Ink4a/Arf RNA or protein in the cell, wherein a decrease in the amount of Ink4a/Arf RNA or protein in the cell as compared to the amount of Ink4a/Arf RNA or protein in a cell not contacted with candidate agent indicates that the candidate agent will treat an individual having a neurodevelopmental disorder or a neurodegenerative disease. In some instances, one parameter is measured. In some instances, multiple parameters are measured.

Cells useful for screening include any cell that expresses USP16. In some instances, the cell overexpresses USP16, e.g. the cell expresses more USP16 than would be observed in wild type cell. For example, the cell may be trisomic for USP16, e.g. the cell may be acutely cultured from a subject having a trisomy at chromosome 21 or a USP16-comprising fragment thereof, i.e. a trisomy 21 primary cell. The cell may be a cell line derived from a trisomy 21 primary cell. The cell may be engineered to overexpress USP16, e.g. by transformation or infection with a vector comprising a nucleic acid that encodes the USP16 protein, by the introduction of USP16 polypeptide directly into the cell, etc. In some instances, the USP16 is expressed extrachromosomally (e.g. from a minicircle, a cosmid, etc.). In other instances, the USP16 is expressed from the genome of the cell. For example, the cell may be, e.g., a neural stem cell, a hematopoietic stem cell, a mammary stem cell, a mesenchymal stem cell, a fibroblast, etc., that either ectopically expresses additional copies of USP16 or that is from an individual (e.g. mouse, rat, human, etc.) having Down's syndrome.

Candidate agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like. Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992).

Candidate agents of interest for screening also include nucleic acids, for example, nucleic acids that encode siRNA, shRNA, antisense molecules, CRISPRi, or miRNA, or nucleic acids that encode polypeptides. Many vectors useful for transferring nucleic acids into target cells are available. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc. Vectors may be provided directly to the subject cells. In other words, the cells are contacted with vectors comprising the nucleic acid of interest such that the vectors are taken up by the cells.

Methods for contacting cells with nucleic acid vectors, such as electroporation, calcium chloride transfection, and lipofection, are well known in the art. Alternatively, the nucleic acid of interest may be provided to the subject cells via a virus. In other words, the cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the nucleic acids comprising the nucleic acid are packaged into viral capsids by a packaging cell line. Different packaging cell lines provide a different envelope protein to be incorporated into the capsid, this envelope protein determining the specificity of the viral particle for the cells. Methods of introducing viral vectors comprising the nucleic acid of interest into packaging cell lines, of collecting the viral particles that are generated by the packaging lines, and of infecting cells using the packaged viral particles are well known in the art.

Vectors used for providing nucleic acid of interest to the subject cells will typically comprise suitable promoters for driving the expression, that is, transcriptional activation, of the nucleic acid of interest. This may include ubiquitously acting promoters, for example, the CMV-b-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing reprogramming factors to the subject cells may include genes that must later be removed, e.g. using a recombinase system such as Cre/Lox, or the cells that express them destroyed, e.g. by including genes that allow selective toxicity such as herpesvirus TK, bcl-xs, etc Candidate agents of interest for screening also include polypeptides. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like.

The polypeptide may comprise the polypeptide sequences of interest fused to a polypeptide permeant domain to promote entry into the cell. A number of permeant domains are known in the art and may be used in the non-integrating polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

The candidate polypeptide agent may be produced from eukaryotic produced by prokaryotic cells, it may be further processed by unfolding, e.g. heat denaturation, DTT reduction, etc. and may be further refolded, using methods known in the art. Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine. The polypeptides may have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

Alternatively, the candidate polypeptide agent may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. Alternatively, the candidate polypeptide agent may be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In some cases, the candidate polypeptide agents to be screened are antibodies. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be either polyclonal antibodies or monoclonal antibodies. Antibodies are typically provided in the media in which the cells are cultured.

Candidate agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by adding the agent to at least one and usually a plurality of cell samples, usually in conjunction with cells not contacted with the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype. In some instances, a positive control may be employed, e.g. a USP16-specific shRNA, a USP16-specific siRNA, and the like.

Various methods can be utilized for quantifying the selected parameters. For example, H2A ubiquitination may be measured by, e.g, chromatin immunoprecipitation (ChIP) of the Ink4a/Arf locus. Ink4a/Arf expression, i.e. RNA or protein levels, may be detected by qRT-PCR, western blots, protein arrays, and the like. Cell proliferation rates and senescence may be measured by flow cytometry, BrdU incorporation, quit fractions, etc. Such methods will be well known to one of ordinary skill in the art.

The following examples are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Example 1

Materials and Methods

Mice. Ts65Dn, Ts1Cje and euploid littermates mice were purchased from Jackson Laboratories and maintained in the mixed background B6EiC3SnF1/J. Mice were genotyped by real-time or by PCR as previously published (Reinholdt, L. G. et al. Molecular characterization of the translocation breakpoints in the Down's syndrome mouse model Ts65Dn. *Mamm. Genome* 22, 685-691 (2011) and Jackson website). Control littermates were used as wild-type mice. These mice are heterozygous for B6 and C3H alleles at all loci in their genome. Usp16$^{het}$ mice (FVB/N-Usp16Tg(Tyr)2414FOve/Mmjax) were acquired from MMRRC. Weaning age NOD/SCID female mice were purchased by Jackson Laboratories. Mice were housed in Stanford University, in SCORE facility or in SIM1 animal facility, in accordance with the guidelines of Institutional Animal Care Use Committee.

Bone marrow and peripheral blood analyses. Isolation and analyses of bone marrow cells were performed as previously described (Akala, O. O. et al. Long-term haematopoietic reconstitution by Trp53−/−p16Ink4a−/−p19Arf−/− multipotent progenitors. *Nature* 453, 228-232 (2008)). In brief, bone marrow cells were isolated by crushing long bones and hips with mortal and pestle in Calcium and Magnesium free HBSS with 2% heat-inactivated bovine serum. The cells were drawn by passing through a 25G needle several times, treated with ACK for 1 minute and filtered with a 40 mm nylon mesh. Before sorting, progenitor cells were enriched through magnetic isolation with Lineage cell depletion kit (Miltenyi Biotec) using an autoMACS pro Separator. Antibodies used for analyses and sort of bone marrow cells were lineage markers (CD3, CD5, CD8, Gr-1, B220 and Ter119), Sca-1, c-kit, CD150, CD48, CD135 (Flt3) and CD34.

For peripheral blood analysis, red blood cells were lysed with hypotonic buffer, and nucleated cells were stained with antibodies against CD45.1, CD45.2, Ter119, Gr-1, Mac-1, CD3 and B220.

All antibodies were directly conjugated or biotinylated and purchased from e-Bioscience, BD Biosciences, or Biolegend. Cells were gated based upon forward and side-scatter profiles, and live/dead discrimination was obtained with 7-Amino-Actinomycin D (7-AAD) or DAPI. Analyses and sorting was performed using a FACS Aria II (BD Biosciences).

Bone marrow transplants. Recipient C57BI CD45.1 mice (8 to 12 weeks old) were lethally irradiated (1,140 rad), with two doses of radiations delivered 3 hours apart. Bone marrow single cell suspensions were obtained from long bones and hips of Ts65Dn, Ts1 Cje and wild type mice (8 to 12 weeks old) and treated for 1 minute with ACK for red cells lysis. Only donor animals with a matching haplotype for the major histocompatibility antigens were used (H2K b/b). Recipient mice were competitively reconstituted by retro-orbital venous sinus injection of three different doses ($5 \times 10^5$ cells, $1.5 \times 10^5$ cells, $0.5 \times 10^5$ cells) of whole bone marrow cells from donor mice mixed with a radioprotective dose of $\sim 3 \times 10^5$ bone marrow cells from non irradiated C57BI/Ka-CD45.1 mice. Five mice were used for each group. Mice were analyzed monthly for reconstitution of peripheral blood.

For secondary transplants, $5 \times 10^6$ bone marrow cells were collected at least four months after primary transplants from engrafted recipients, and injected in lethally irradiated C57BI CD45.1 mice. Reconstitution was measured in peripheral blood at the indicated time points.

For transplantation of lentivirus-infected Ts65Dn marrow cells, KLS cells were isolated and sorted from 8 to 12 weeks old Ts65Dn H2K b/b mice. Sorted KLS were incubated overnight with the indicated lentivirus (MOI=200). The morning after, KLS were washed, mixed with a radioprotective dose of $3 \times 10^5$ bone marrow cells from unirradiated C57BI/Ka-CD45.1 mice, and injected in lethally irradiated mice. In parallel, 48 hours after infection we verified by FACS the level of GFP expression in infected cells, to make sure that the level of lentiviral integration would be similar between multiple samples.

For all the transplantation experiments, mice that were consider as repopulated by donor cells were mice that had more than 1% donor-derived (CD45.2+) cells in both lymphoid (CD3+ and B220+) and myeloid (Gr-1+ and Mac-1+) subpopulations. Frequency of long-term reconstituting cells from limiting dilution experiments was calculated using ELDA software (Hu, Y. et al. ELDA: extreme limiting dilution analysis for comparing depleted and enriched populations in stem cell and other assays. *J. Immunol. Methods* 347, 70-78 (2009)).

In vitro colony formation of hematopoietic stem cells. For Methocult cultures, single wild-type HSCs were double-sorted into U-bottom 96-well plates containing 100 µl of Methocult GF M3434 media (StemCell Technologies) as previously described (Akala, O. O. et al. Long-term haematopoietic reconstitution by Trp53−/−p16Ink4a−/−p19Arf−/− multipotent progenitors. *Nature* 453, 228-232 (2008)). Positive colonies were scored on day 7 of culture.

Neurosphere assays. Wild type, Ts65Dn, Ts65Dn/USP16$^{het}$ and USP16$^{het}$ mice were euthanized by $CO_2$, decapitated and their brains were immediately removed. The subventricular zone was micro dissected and stored in ice-cold PBS for further processing. The tissue was digested using TryPLE express (Invitrogen) and DNase I (250 units/ml) at 37° C. for 10 minutes followed by trituration using a fire polished pipette. Digested tissue was washed in ice cold PBS without calcium magnesium, filtered through a 40 um filter and resuspended in neurospheres growth media, i.e Neurobasal-A (Invitrogen) and DMEM F/12 (1:1) supplemented with 2% B27-A (Invitrogen), 1% N2 (Invitrogen), mouse recombinant EGF (20 ng/ml) and bFGF (20 ng/ml) (Shenandoah Biotechnology) and 2 ug/ml heparin (Sigma).

Lineage cells were depleted using mouse CD45, CD31, CD34 and Ter119 microbeads (miltenyi) and the negative fraction collected. For FACS analysis the cells were stained with anti-CD15-FITC (MMA; BD), anti-Prominin1-APC (ebiosciences) and biotinylated EGF complexed with PE-Cy7-streptavidin (2 µg/mL; Invitrogen).

For limiting dilution analysis, cells were directly plated in 96 wells in limiting dilution Down's to one cell per well. Each plating dose was done in 24 wells and the number of wells with neurospheres was counted after 10 days. For serial passaging neurospheres from each passage were collected and replated either as 100 cells per well in a 48 well dish or in a similar limiting dilution fashion as described above.

Mouse breast analyses. Mammary glands were dissected from either wild type, Ts65Dn or Ts1 Cje mice and analyzed as previously described (Stingl, J. et al. Purification and unique properties of mammary epithelial stem cells. *Nature* 439, 993-997 (2006)). Briefly the glands were digested in Collagenase/Hyaluronidase followed by ACK lysis, trypsin and DNAase/Dispase. The cells were then stained with the following antibodies: CD45, CD31, Ter119, CD49f and CD24 (Biolegend).

For all experiments, antibodies were directly conjugated or biotinylated and purchased from e-Bioscience, BD Biosciences, or Biolegend. Cells were gated based upon forward and side-scatter profiles, and live/dead discrimination was obtained with 7-Amino-Actinomycin D (7-AAD) or DAPI. Analyses and sorting was performed using a FACS Aria II (BD Biosciences).

In vitro mammary colony forming assays. 96-well ultra-low attachment plates (BD) were prepared with a feeder layer of irradiated L-WNT3a mixed with 60 µl of growth factor reduced Matrigel (BD) per well. 1000 sorted MRUs from WT, Ts65Dn or Ts1 Cje mice were then plated into liquid media as previously described (Dalerba, P. et al. Single-cell dissection of transcriptional heterogeneity in human colon tumors. *Nat. Biotechnol.* 29, 1120-1127 (2011); Zeng, Y. A. et al. Wnt proteins are self-renewal factors for mammary stem cells and promote their long-term expansion in culture. *Cell Stem Cell* 6, 568-577 (2010)). 10% FBS and 2.5% growth factor reduced Matrigel were added as supplements.

Mammary transplants. Lineage⁻ (CD45$^+$CD31$^+$Ter119$^+$) cell populations were isolated from 12-week mice in staining media and resuspended in 10 µl of sterile PBS+30% matrigel per transplant before being injected into the cleared fat pads of 21-28 day old recipient NOD/SCID mice as previously described (Stingl, J. et al. Purification and unique properties of mammary epithelial stem cells. *Nature* 439, 993-997 (2006)). All transplants were allowed to grow for at least 6 weeks but not more than 10 weeks before analysis. For knockDown's of Usp16 Lineage– cells were infected with either control lentivirus or shRNA against Usp16 in DMEM/F12+10% FBS overnight. The cells were then washed and resuspended in sterile PBS+30% matrigel for transplant.

For mammary transplant outgrowth area calculation, NIH Image J software was used. Briefly, GFP positive mammary ducts were measured with the free-hand tool by drawing a shape around the duct. Measurements were performed in a 'blind' fashion and at the same magnification for all samples. Only positive outgrowths were used in the measurement.

Immunofluorescence of Mammary Tissue. 12 week old mice were euthanized and mammary glands were surgically removed. Glands were fixed in formalin overnight and then transferred to 70% ethanol. They were then embedded in paraffin and sectioned for histology. For staining the slides were deparafinised in xylene and alcohol grades. Antigen retrieval was carried out in Tris-EDTA buffer by heating in a microwave for 20 min. Primary antibodies CK14 (Covance) and CK8 were applied overnight. Secondary antibodies were anti-rat DyLight 488 and anti-rabbit DyLight 594 (both from Jackson Labs). Sections were then mounted using Prolong Anti-fade reagent (Invitrogen). Images were taken with a NIKON inverted microscope.

Western Blot and Chromatin Immunoprecipitation. For Western blot analyses, chromatin extracts were prepared with subcellular protein fractionation kit (Thermo Scientific). H2AK119 antibody (rabbit) was purchased from Cell Signaling; H2A antibody was purchased from Chromatin Immunoprecipitation was performed essentially as previously described (Negishi, M. et al. A novel zinc finger protein Zfp277 mediates transcriptional repression of the Ink4a/arf locus through polycomb repressive complex 1. *PLoS ONE* 5, e12373 (2010)) using the polyclonal antibody for H2AK119 (Cell Signaling).

Lentivirus preparation. The lentiviral vector that we used for downregulation was vector pSicoR-GFP (Ventura, A. et al. Cre-lox-regulated conditional RNA interference from transgenes. *Proc. Natl. Acad. Sci. U.S.A.* 101, 10380-10385 (2004)). We cloned the following hairpins: shC (TTCTC-CGAACGTGTCACGT) shUSP16 #1 (CGAGTGCTGTAT-TCCTTATAT), shUSP16 #2 (TTCTCTGGAAATACAC-CTATG), shp16 (CATCAAGACATCGTGCGATAT), shp19 (GCCATCTAAACGGTTCAGTTT), human shUSP16 ( ). A lentivirus construct expressing Cherry and Bmi1 (pEIZ-HIV-mCherry-Bmi1) was kindly by Dr. Y. Shimono (Shimono, Y. et al. Downregulation of miRNA-200c links breast cancer stem cells with normal stem cells. *Cell* 138, 592-603 (2009)). USP16 overexpression vector was obtained by subcloning USP16 clone (ATCC) in pCDH-MSCV-GFP vector (SBI).

Viruses were produced in 293T cells with a second-generation lentivirus system. Supernatants were collected at 48 hrs and 72 hrs, and concentrated through ultracentrifugation (Tiscornia, G. et al. Production and purification of lentiviral vectors. *Nat Protoc* 1, 241-245 (2006)). Viral titers were calculated by FACS analyses of 293T cells infected with serial dilution of concentrated virus.

Mouse Embryonic Fibroblasts (MEFs) and Terminal Tip-Tail Fibroblasts (TTFs). Mouse embryonic fibroblasts (MEFs) were generated from E14.5 embryos obtained from Ts65Dn mothers. Genotype was verified by real time PCR. Cells were passaged 1:4 when almost confluent. To culture mouse primary tip-tail fibroblasts (TTFs), the skin was peeled from tail tips of wild type (n=4), Ts65Dn (n=3), Ts65Dn/Usp16$^{het}$ (n=3) and Usp16$^{het}$ (n=1) 8-weeks old mice, finely minced with a blade and shortly digested in trypsin. Resulting pieces were incubated in DMEM containing 20% FBS for three weeks. Derived fibroblasts were then passaged to new plates and considered P2. Human fibroblasts (WT: CRL-2088, CRL-2076; DS: CCL-54, CRL-7090, CRL-7031) were purchased by ATCC.

Fibroblasts proliferation, SA-βGal and p16 staining. 5×10$^3$ fibroblasts were seeded in a 24-well plate and viable cells were counted by trypan blue exclusion at the indicated time points.

For SA-βGal staining of senescent cells, the Senescence Detection Kit (Abcam, ab65351) was used according to manifacturer's protocol.

For p16 staining, fibroblasts were permeabilized with 0.2% Triton-PBS, blocked in 3% BSA-PBS and stained with a mouse anti-human p16 (JC8, Santa Cruz Biotechnology, CA) or rabbit anti-mouse p16. Specific secondary antibodies (Alexa Fluor 488 anti-mouse and Alexa Fluor 647 anti-rabbit) were used 1:1000.

SA-βGal and p16 staining were detected by microscope at 10× and the positive cells were evaluated in three different fields per well. Three technical replicates were performed.

In experiments with infected cells, cells were sorted based on GFP or Cherry expression and expression of the construct was verified by real-time PCR.

RNA expression analyses. For real-time analyses, cells were collected in trizol (Invitrogen), and RNA was extracted following the manufacturer's protocol. cDNA was obtained using Superscript III First Strand Synthesis (Invitrogen).

Real time reactions were assembled using Taqman probes (Applied Biosystem) in accordance with the manufacturers' directions. Expression data were normalized by the expression of housekeeping genes ActB and GAPDH. Probes used in this study: USP16 (Mm_00470393, Mm_00470406), p16Ink (Mm_01257348, Mm_00494449), p19Arf (Mm_00486943), ActB (Mm_00607939), GAPDH (Mm_99999915), Hoxa1 (Mm00439359_m1), Hoxa3 (Mm01326402_m1), Hoxa5 (Mm01326402_m1).

Immunofluorescence of histones in MEFs and HSCs. Cells were cultured for 48 hours (for MEFs) or directly cytospinned on glass slides after purification (for HSC). Cells were fixed in PFA 2% for 10 minutes and washed in PBS triton 0.1%. Cells were blocked in PBS with Donkey serum 10% for 1 hour at room temperature prior to incubation with primary antibody at 4 C overnight. Incubation with secondary antibody and DAPI was set for 45 minutes at RT. Alternatively antibody staining was performed with Zenon Kit (Invitrogen) following manufacturer's directions. Samples were then mounted and imaged.

Imaging was performed using a Zeiss Observer Z1 fluorescent microscope (Zeiss) equipped with a Hamamatsu Orca-ER camera or a Zeiss confocal system LSM710 (Zeiss). Data acquisition and foci measurements were performed using Improvision Volocity software (Perkin Elmer).

The primary antibody used in this study was anti Ubiquityl-histone H2A D27C4 (Cell Signaling). Secondary antibodies were Alexa 488 and 594.

Results

Ts65Dn, but not Ts1Cje, mice have defective hematopoietic stem cells. Previous reports show that Ts65Dn, Ts1 Cje and Tc1 mice (that contain an almost complete, freely segregating copy of Hsa21) present macrocytic anemia and, with the exception of Ts1cje mice, show an increase number of megakaryocytes and extramedullary hematopoiesis in old age (Kirsammer, G. et al. Highly penetrant myeloproliferative disease in the Ts65Dn mouse model of Down's syndrome. *Blood* 111, 767-775 (2008); Carmichael, C. L. et al. Hematopoietic defects in the Ts1 Cje mouse model of Down's syndrome. *Blood* 113, 1929-1937 (2009); Alford, K. A. et al. Perturbed hematopoiesis in the Tc1 mouse model of Down's syndrome. *Blood* 115, 2928-2937 (2010)). However, hematopoietic stem cells (HSCs) were not fully characterized in adult Ts65Dn or Ts1 Cje mice.

Figure 7:
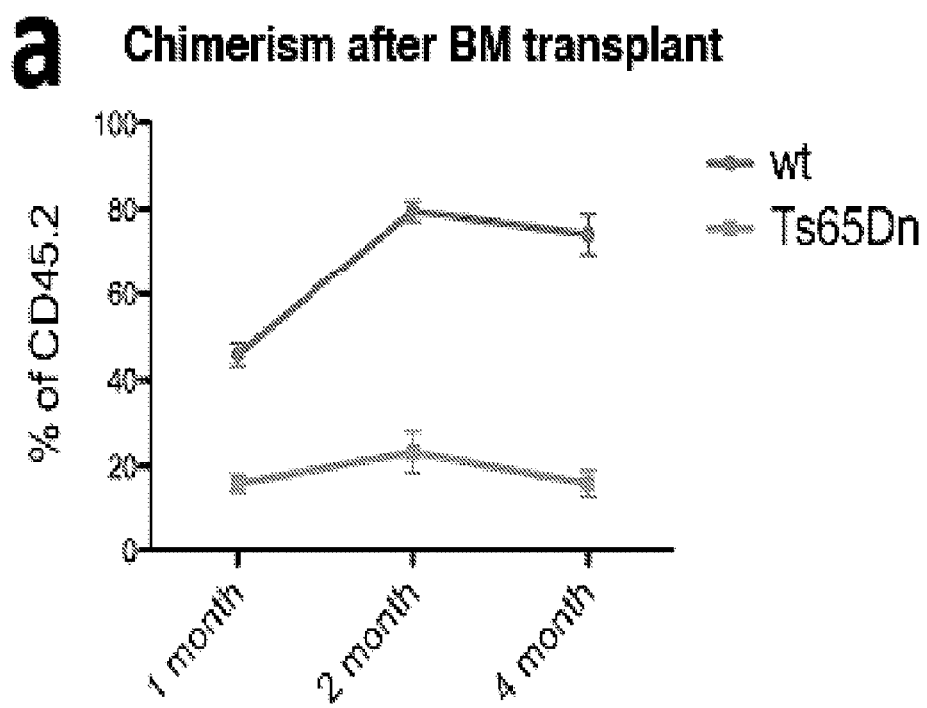
FIG. 7. DS mice model bone marrow engraftment. a) Lethally irradiated C57Bl6 mice (CD45.1) were transplanted with 5×105 CD45.2 bone marrow cells from wild type or Ts65Dn mice (matched for H2K alleles) together with 3×105 CD45.1 cells (5 mice per genotype). Percentage of chimerism was evaluated at the indicated time point. b. Peripheral blood analyses four months after bone marrow transplant revealed multineage engraftment in Ts65Dn mice only with 500,000 donor cells. b) Lower dose of Ts65Dn donor bone marrow failed to reconstitute hematopoietic lineages. Representative FACS plots are shown. Mice were considered positive for engraftment when at least 1% of peripheral blood cells were derived from the donor for each hematopoietic cell lineage: B cells (B220+), T cells (CD3+) and myeloid cells (Gr1+Mac1+).
Figure 7:
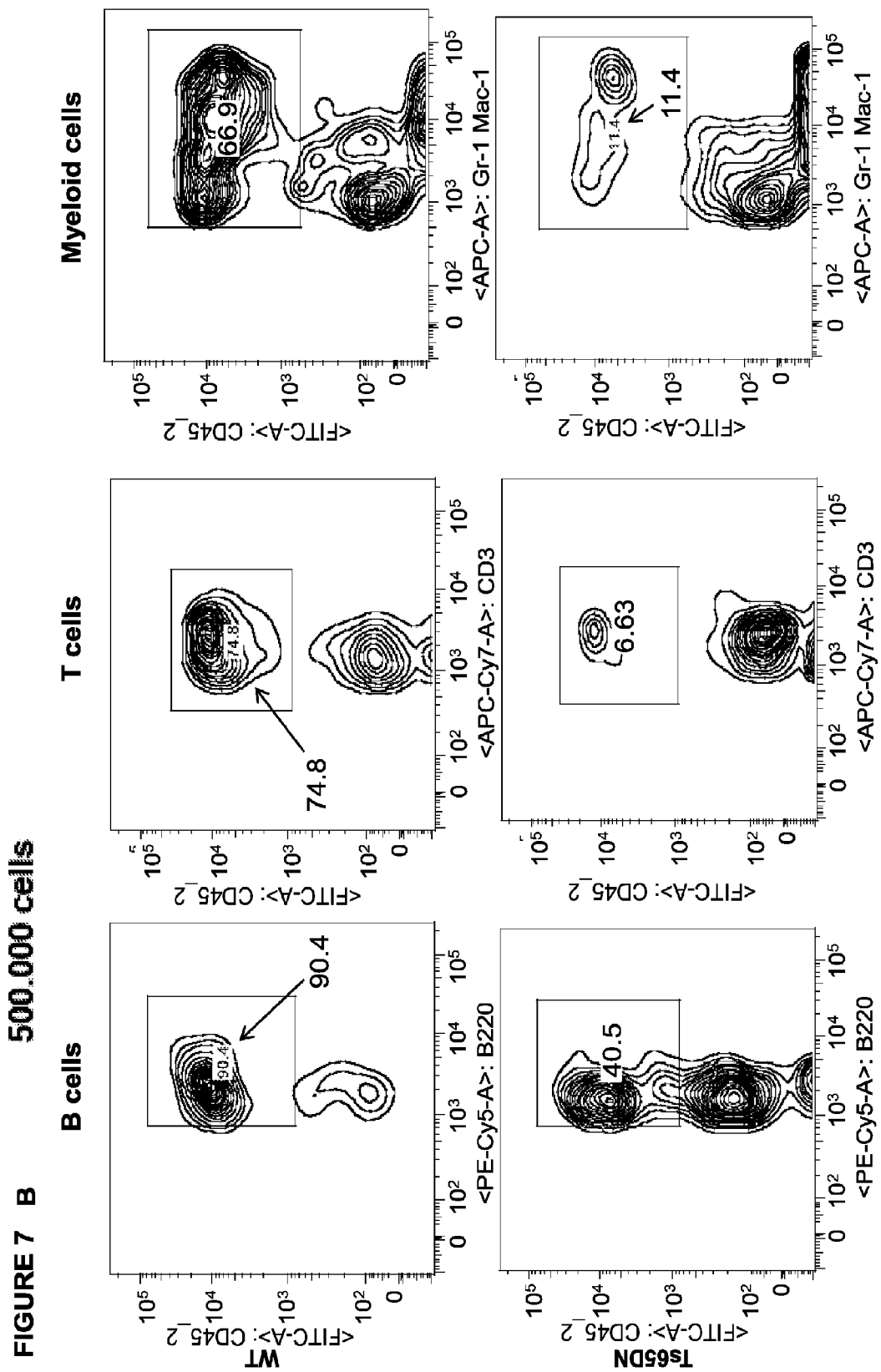
Figure 7:
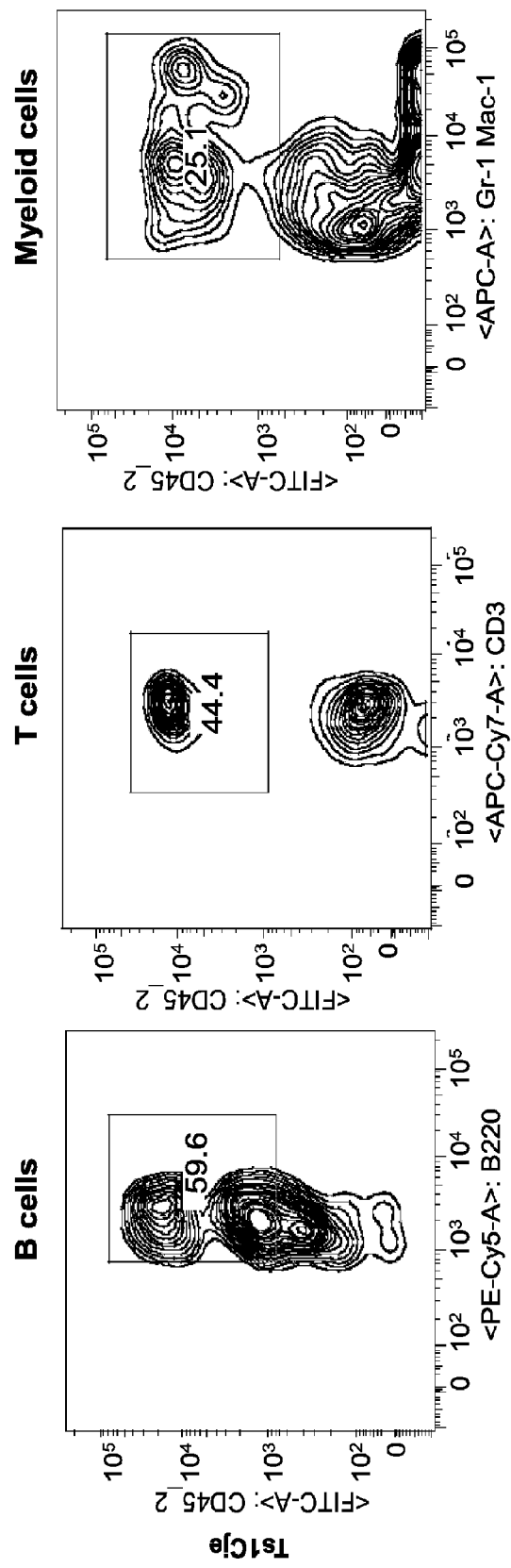

To evaluate the presence of hematopoietic defects in the Ts65Dn mouse model, we performed transplantation with Ts65Dn bone marrow mononuclear cells. Consistent with previous observations (Lorenzo, L. P. E. et al. Defective hematopoietic stem cell and lymphoid progenitor development in the Ts65Dn mouse model of Down's syndrome: potential role of oxidative stress. *Antioxid. Redox Signal.* 15, 2083-2094 (2011)), we found that transplantation of $5\times10^5$ CD45.2+ Ts65Dn cells resulted in lower hematopoietic chimerism in recipient mice compared to transplantation of wild type bone marrow cells (FIG. 7a).

To elucidate the trisomic gene(s) responsible for the impaired engraftment potential of the Ts65Dn bone marrow cells, the composition of wild type, Ts65Dn and Ts1 Cje bone marrow immunophenotypes was profiled. The fraction of CD150$^+$CD48$^-$ KLS cells, which enriches for HSCs in normal mice (Kiel, M. J., et al. SLAM family receptors distinguish hematopoietic stem and progenitor cells and reveal endothelial niches for stem cells. *Cell* 121, 1109-1121 (2005)), was reduced by more than three-fold in Ts65Dn mice. By contrast, the frequency of CD150$^+$ CD48$^-$ KLS cells was normal in Ts1Cje mice (FIG. 1b). This suggested a reduction of the hematopoietic stem cell self-renewal ability specifically in the Ts65Dn mice. Further analyses using different surface markers to isolate a stem cell-enriched population (CD34 and Flt3) (Chao, M. P. et al. Establishment of a normal hematopoietic and leukemia stem cell hierarchy. *Cold Spring Harb. Symp. Quant. Biol.* 73, 439-449 (2008)) also suggested an HSC deficit in the Ts65Dn bone marrow but not in Ts1Cje mice (FIG. 1b). Notably, the CD34$^-$ CD150$^+$ CD48$^-$ KLS fraction is known to be enriched for quiescent stem cells (Wilson, A. et al. Dormant and self-renewing hematopoietic stem cells and their niches. *Ann. N. Y. Acad. Sci.* 1106, 64-75 (2007); Wilson, A. et al. Hematopoietic stem cells reversibly switch from dormancy to self-renewal during homeostasis and repair. *Cell* 135, 1118-1129 (2008)), and it is significantly reduced in Ts65Dn mice (FIG. 1c).

To evaluate the colony formation capacity of Ts65Dn and Ts1 Cje HSC cells in vitro, we plated single CD34$^-$ CD150$^+$ CD48$^-$ KLS cells in Methocult using conditions that robustly support expansion of single HSCs (Park, I.-K. et al. Bmi-1 is required for maintenance of adult self-renewing haematopoietic stem cells. *Nature* 423, 302-305 (2003); Morrison, S. J., et al. The long-term repopulating subset of hematopoietic stem cells is deterministic and isolatable by phenotype. *Immunity* 1, 661-673 (1994); Akala, O. O. et al. Long-term haematopoietic reconstitution by Trp53–/– p16Ink4a–/–p19Arf–/– multipotent progenitors. *Nature* 453, 228-232 (2008)). The ability to generate colonies one week after plating was significantly reduced in HSCs from Ts65Dn, but not from Ts1Cje mice (FIG. 1d).

Figure 8:
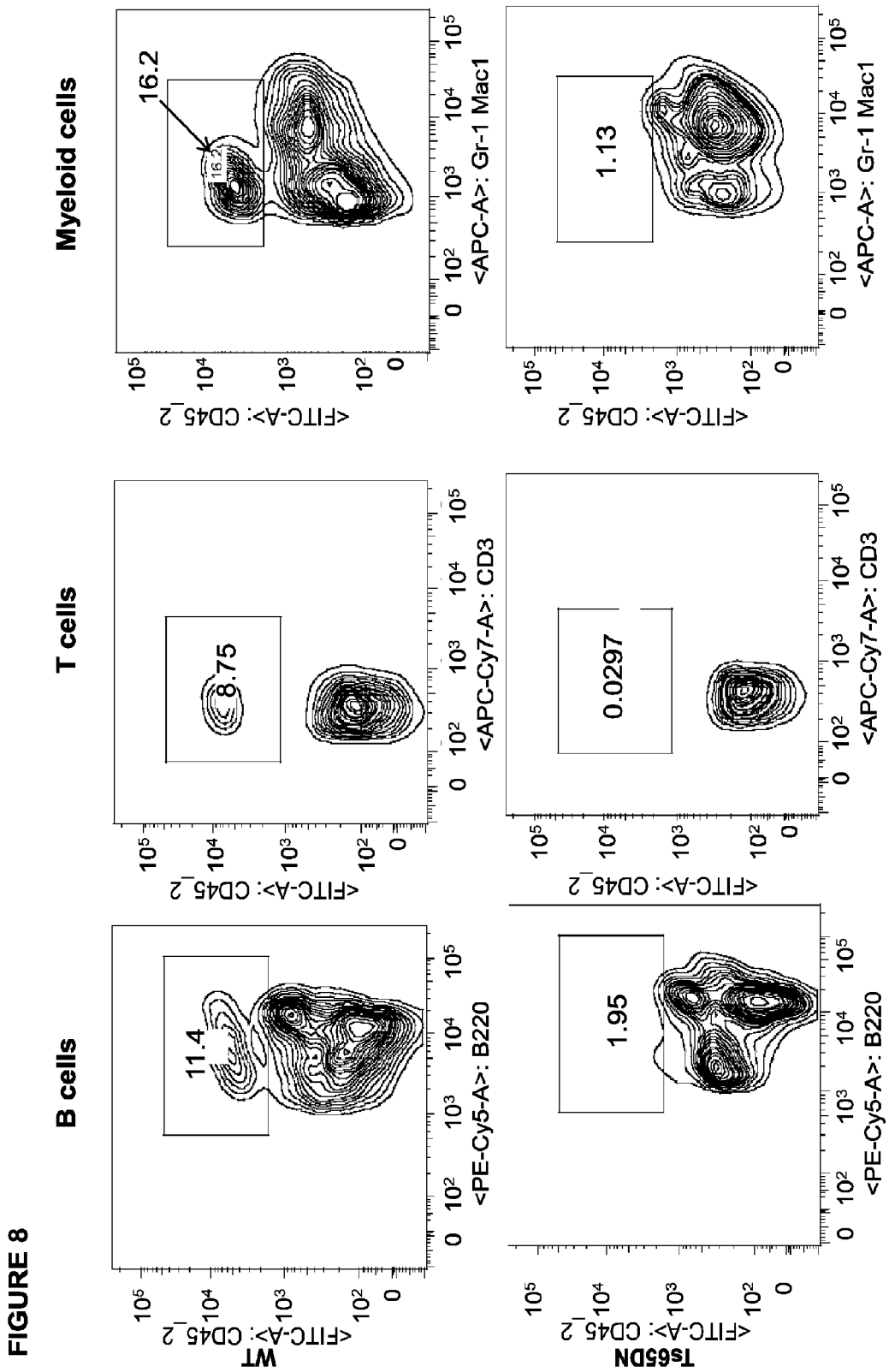
FIG. 8. Ts65Dn bone marrow cells failed are unable to reconstitute secondary recipients. Multilineage analyses of peripheral blood three months after transplantation of bone marrow from engrafted primary recipients in lethally irradiated C57Bl6 mice. Ts65Dn cells are not able to expand in secondary recipients. Representative FACS plots are shown.

To definitively assess the properties of HSCs in DS, we performed serial dilution bone marrow transplantations with wild type, Ts65Dn and Ts1 Cje cells. Wild type and Ts1 Cje bone marrow cells reconstituted the bone marrow of lethally irradiated recipient mice with a similar HSC calculated frequency (1/80,338 and 1/103,553 respectively, p=0.668). Conversely, there was a three-fold reduction in the frequency of Ts65Dn stem cells (1/307,431; p=0.0294) (FIG. 1e and FIG. 7b). Furthermore, multi-lineage engraftment of Ts65Dn bone marrow cells was not observed in secondary transplants after three months (Figure if and FIG. 8), further confirming a severe impairment in the self-renewal ability of Ts65Dn hematopoietic cells. Thus Ts65Dn, but not Ts1 Cje mice have defects in HSC self-renewal, reconstitution ability and in vitro colony formation.

Downregulation of Usp16 ameliorates the self-renewal defects of HSCs in Ts65Dn mice. Usp16, a previously described de-ubiquitinating enzyme, is one of the genes known in the art to be uniquely triplicated in Ts65Dn mice but not in Ts1 Cje mice. This gene has been shown to be involved in chromatin remodeling, including erasing ubiquitin modifications by Polycomb complex PRC1 on histone H2A (Joo, H.-Y. et al. Regulation of cell cycle progression and gene expression by H2A deubiquitination. *Nature* 449, 1068-1072 (2007)). Since PRC1, which includes Bmi1, has shown to be essential for the self-renewal of stem cells in multiple tissues (Molofsky, A. V. et al. Bmi-1 dependence distinguishes neural stem cell self-renewal from progenitor proliferation. *Nature* 425, 962-967 (2003); (Park, I.-K. et al. Bmi-1 is required for maintenance of adult self-renewing haematopoietic stem cells. *Nature* 423, 302-305 (2003); Liu, S. et al. Hedgehog signaling and Bmi-1 regulate self-renewal of normal and malignant human mammary stem cells. *Cancer Res.* 66, 6063-6071 (2006); Pietersen, A. M. et al. Bmi1 regulates stem cells and proliferation and differentiation of committed cells in mammary epithelium. *Curr. Biol.* 18, 1094-1099 (2008); van der Lugt, N. M. et al. Posterior transformation, neurological abnormalities, and severe hematopoietic defects in mice with a targeted deletion of the bmi-1 proto-oncogene. *Genes Dev.* 8, 757-769 (1994)), we wondered if an extra copy of Usp16, a known modifier of PRC1 mediated H2A ubiquitination, impairs the self-renewal ability of stem cells in Ts65Dn mice.

To understand the function of Usp16 in the hematopoietic system of Ts65Dn mice, we first confirmed that Usp16 mRNA was expressed 1.5 fold higher in Ts65Dn HSCs compared to wild type HSCs (FIG. 2a). Next, the levels of H2AK119 ubiquitination were measured. Immunofluorescence studies showed a two-fold reduction in the number of ubiquitinated chromatin foci in Ts65Dn CD34$^-$CD150$^+$CD48$^-$KLS cells (FIG. 2b). Both immunofluorescence and Western blot analyses demonstrated a reduction in the level of H2AK119 ubiquitin in MEF cells (FIG. 9).

To determine whether elevated levels of Usp16 contributes to abnormalities of Ts65Dn HSCs, we generated two lentiviral constructs encoding GFP and an shRNAs directed against USP16 (shUSP16 #1 and shUSP16 #2) or a scrambled shRNA (shC). These Usp16 hairpins do not completely ablate Usp16 expression, reducing it to 40-50% (FIG. 2c) and leading to a final expression level of USP16 similar to the one observed in wild type mice. Around 40% of single CD34$^-$CD150$^+$CD48$^-$ KLS Ts65Dn bone marrow cells infected with the shUSP16 lentivirus were able to grow in vitro in Methocult, while only 20% of the shC-infected cells formed colonies (FIG. 2d) (p-value<0.04).

To assess in vivo the effect of Usp16, Ts65Dn KLS cells were infected with shUSP16 or shC lentivirus vectors and then injected into recipient lethally irradiated C57B16 mice. shUsp16 infected cells, but not shC cells, significantly engrafted in the recipient mice (FIG. 2e and FIG. 10a). Unlike Ts65Dn bone marrow cells treated with a control lentivirus, the cells transduced with the shUsp16 lentivirus could also give rise to multipotent differentiation upon serial transplantation (FIG. 2f and FIG. 10b). These results demonstrate that the self-renewal defect of Ts65Dn HSCs can be substantially rescued by downregulation of Usp16 alone.

USP16 plays a role in the expansion defect of Ts65Dn neural progenitors. Since Usp16 might affect polycomb activity by removal of the H2AK119 ubiquitin mark, we hypothesized that an extra copy of Usp16 in Ts65Dn mice could have a role not only in the hematopoietic system but also in other tissues, including the brain. Indeed PRC1 is known to be particularly critical for maintenance of neural progenitor cells (Molofsky, A. V. et al. Bmi-1 dependence distinguishes neural stem cell self-renewal from progenitor proliferation. *Nature* 425, 962-967 (2003); Molofsky, A. V. et al. Bmi-1 dependence distinguishes neural stem cell self-renewal from progenitor proliferation. *Nature* 425, 962-967 (2003); Cao, G. et al. Bmi-1 absence causes premature brain degeneration. *PLoS ONE* 7, e32015 (2012)).

Figure 3:
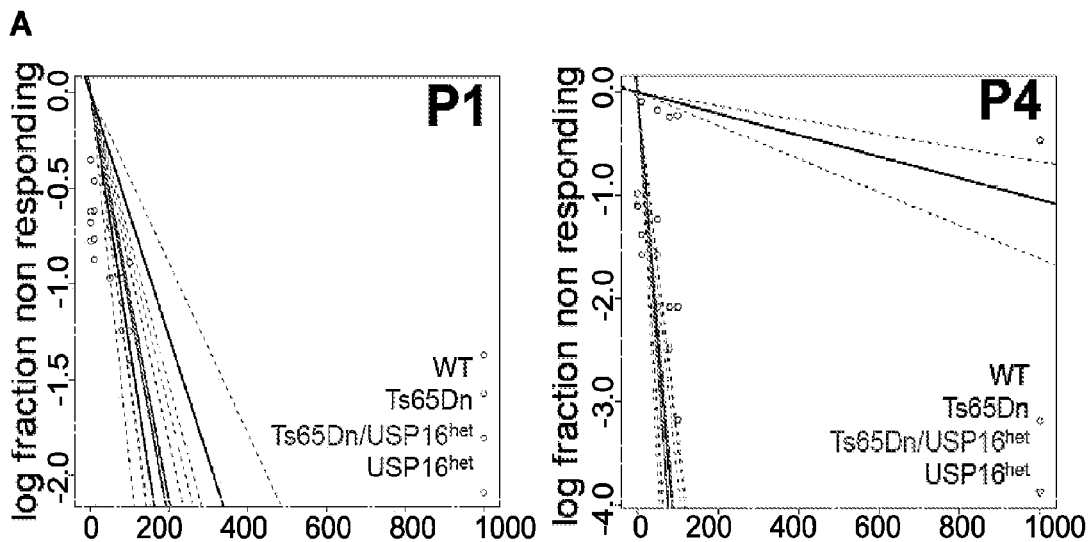
FIG. 3. Ts65Dn mice, but not Ts65Dn/Usp16$^{het}$ mice, show defective neural progenitor cells. A) Serial dilution analysis of Lin⁻ cells derived from the SVZ. ELDA analyses are shown for Passage 1 (P1) in the left panel and for passage 4 (P4) in the right panel. The table shows the estimated Nsp-IC frequency in the indicated conditions: it is significantly decreased in Ts65Dn mice, but not in Ts65Dn/USP16$^{het}$ mice. B) Changes in Nsp-IC frequency after serial passaging. Ts65Dn derived neurospheres show a significant decrease in the frequency after 4 passages compared to Ts65Dn/Usp16$^{het}$ neurospheres (p=0.0294). C) A decrease of Sox2 mRNA levels is observed by qPCR analysis of Ts65Dn neurospheres harvested at P1 and P4 and is rescued in Ts65Dn/USP16$^{het}$ cells. D) Limiting dilution analysis of Lin⁻ cells isolated from SVZ and sorted for CD133⁺EGFR⁺ (left) or CD15⁺EGFR⁺ (right). The table shows the estimated frequencies for the indicated sorted populations. Ts65Dn mice have decreased frequency of Nsp-ICs. E) The neurosphere-forming potential was assayed by secondary sphere formation. The Ts65Dn mice had significantly lower potential to sustain neurospheres passaging compared to wild type or Ts65Dn/USP16$^{het}$ mice (*** p<0.001). Each experiment was carried out in a minimum of three mice per genotype.
Figure 3:
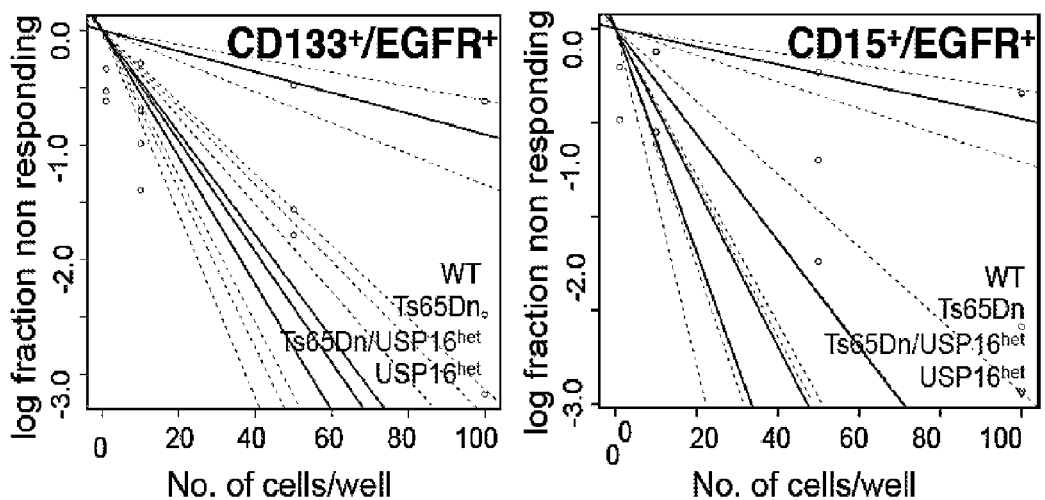
Figure 3:
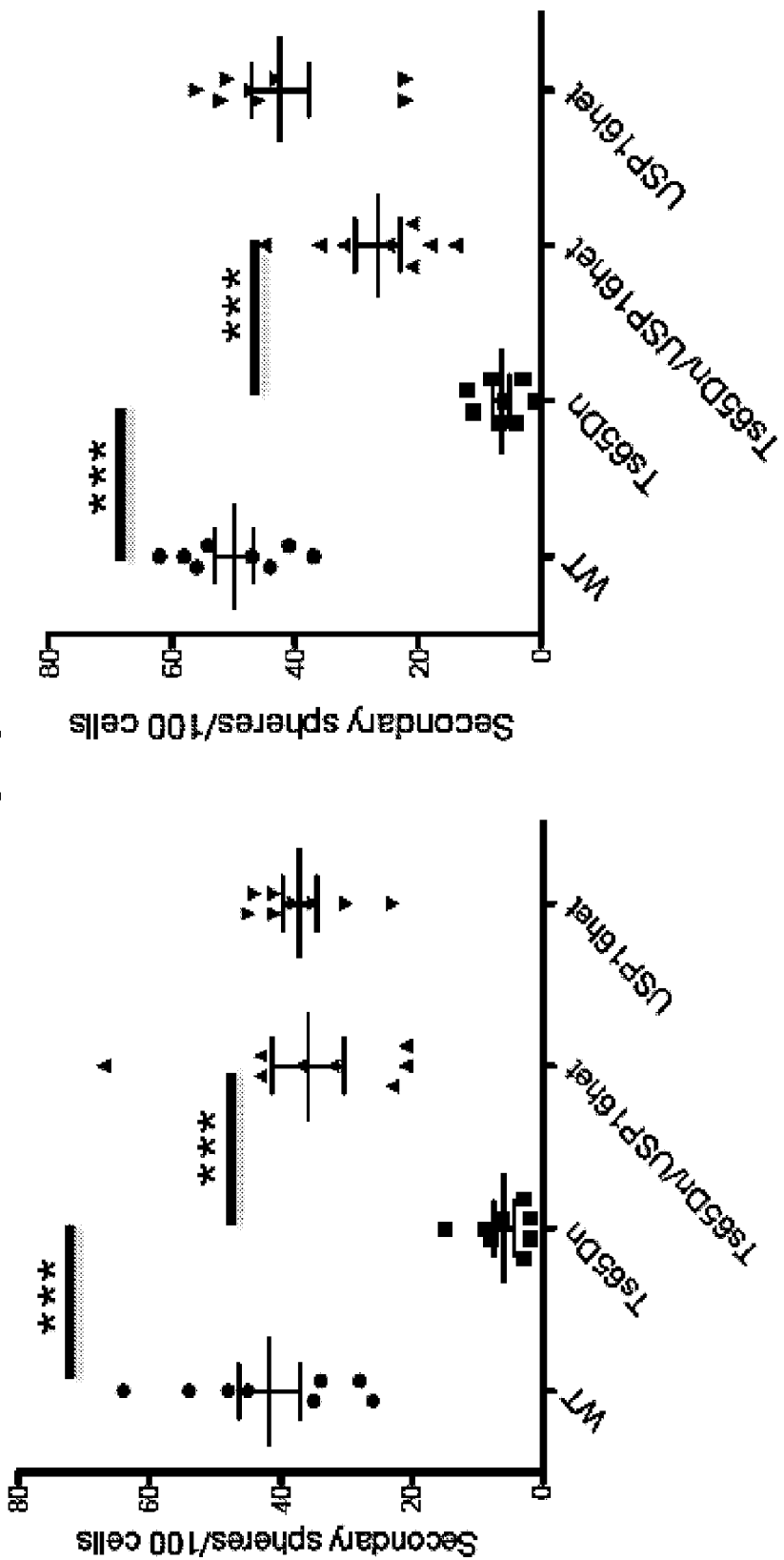

To understand whether Usp16 trisomy plays a role also in neural progenitor cells of Ts65Dn mice, the in vitro expansion of wild type and Ts65Dn mouse neural progenitor cells derived from the sub-ventricular zone (SVZ), one of the major sites of adult neurogenesis, was tested. The SVZ was micro dissected from 8 week old mice brains and CD24$^-$CD31$^-$CD45$^-$CD119$^-$(Lin$^-$) cells were enriched by flow cytometry. These cells were tested for their ability to form neurospheres and to serially passage in vitro. In agreement with other reports suggesting that there is a defect in neural progenitors of Ts65Dn mice (Moldrich, R. X. et al. Down's syndrome gene dosage imbalance on cerebellum development. *Prog. Neurobiol.* 82, 87-94 (2007); Lorenzi, H. A. et al. Hippocampal hypocellularity in the Ts65Dn mouse originates early in development. *Brain Res.* 1104, 153-159 (2006)), the frequency of clonogenic neurosphere initiating cells (Nsp-Ic) formed by Ts65Dn cells was halved compared to wild type cells (FIG. 3a). This frequency increased two- to four-fold by the fourth passage in wild type cells, while Ts65Dn Lin$^-$ cells completely lost their ability to form neurospheres by this time (FIG. 3a-b). To define the role of an extra copy of USP16 in neural progenitor expansion, Ts65Dn mice were bred with mice in which one of the normal Usp16 alleles was mutated (Usp16$^{het}$). The offspring have a normal diploid dosage of Usp16, but retain three copies of the other genes present in the Ts65Dn parental strain (Ts65Dn/Usp16$^{het}$ mice). The loss of an extra allele of Usp16 in Ts65Dn/Usp16$^{het}$ neural progenitor cells restored the ability of Lin$^-$ cells to form neurospheres and to be passaged (FIG. 3a-b). The expression of Sox2 (a known neural progenitor cell marker) (Ellis, P. et al. SOX2, a persistent marker for multipotential neural stem cells derived from embryonic stem cells, the embryo or the adult. *Dev. Neurosci.* 26, 148-165 (2004)) was also tested, and it increased by two-fold after four serial passages of wild type Lin− neural cells (FIG. 3e and FIG. 10c). By contrast, at passage 4 there is no detectable expression of Sox2 by Lin$^-$ Ts65Dn neural cells. Ts65Dn/Usp16$^{het}$ cells express comparable levels of Sox2 in passage 4 as wild type cells (FIG. 3c).

Figure 11:
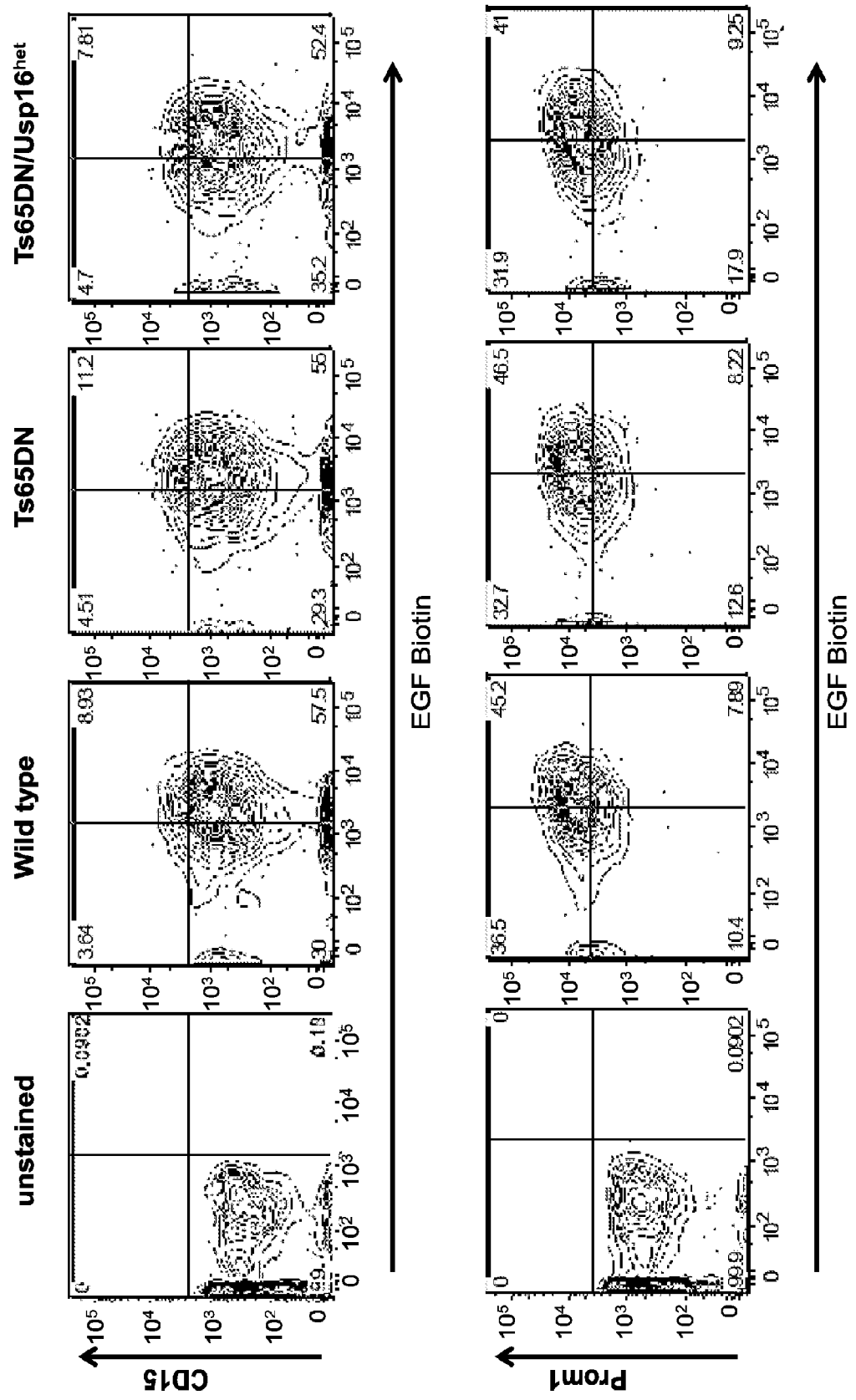
FIG. 11. Sorting scheme of SVZ single cell suspension. Representative FACS plots are shown for viable Lin⁻ cells derived from SVZ preparations. The upper row shows the expression in different Lin⁻ cells of CD15 and EGFR. The lower row shows the expression of CD133 (Prom1) and EGFR. Double positive cells were sorted and used for testing neurosphere-formation potential.

To further investigate the expansion properties of neural progenitor cells, CD133$^+$EGFR$^+$ Lin$^-$ (Fischer, J. et al. Prospective isolation of adult neural stem cells from the mouse subependymal zone. *Nat Protoc* 6, 1981-1989 (2011); Pastrana, E. et al. Simultaneous prospective purification of adult subventricular zone neural stem cells and their progeny. *Proc. Natl. Acad. Sci. U.S.A.* 106, 6387-6392 (2009)) and CD15$^+$ EGFR$^+$ Lin$^-$ (Capela, A. et al. LeX/ssea-1 is expressed by adult mouse CNS stem cells, identifying them as nonependymal. *Neuron* 35, 865-875 (2002)) cells were analyzed and isolated from SVZs (FIG. 11). Sphere limiting dilution analyses of either CD133$^+$EGFR$^+$ Lin$^-$ cells or CD15$^+$EGFR$^+$Lin$^-$ cells revealed a significant decrease in the frequency of Nsp-Ic in the Ts65Dn mice as compared to wild type or to Ts65Dn/Usp16$^{het}$ mice (FIG. 3d). Moreover, secondary sphere formation assays showed a significant decrease in the potential of Ts65Dn, but not Ts65Dn/Usp16$^{het}$, neural progenitor cells to form spheres (FIG. 3e). Taken together, these data show that Ts65Dn mice have a defect in the expansion of neural progenitors that can be at least partially rescued by simply eliminating an extra allele of Usp16.

Figure 4:
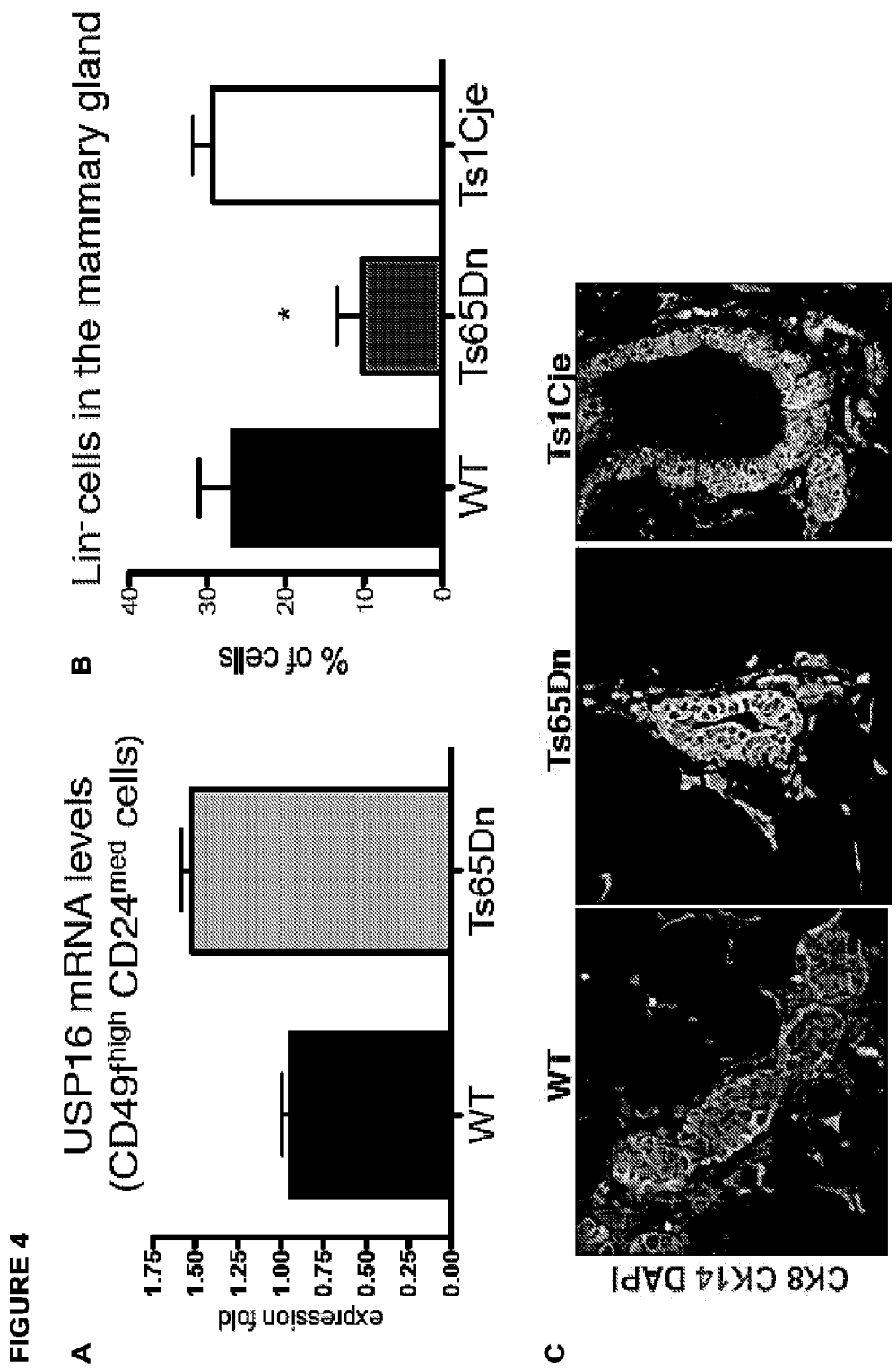
FIG. 4. Mammary glands changes in Ts65Dn mice depend on the levels of Usp16. A) Quantitative real-time PCR was used to measure expression of Usp16 mRNA levels in wildtype (black) and Ts65Dn (grey) in CD49$^{high}$CD24$^{med}$ cells. B) Ts65 Dn, but not Ts1 Cje mice, have a marked reduction in the number of mammary Lin⁻ cells. The analysis includes at least five animals for each group (p=0.0118). C) Immunofluorescence staining for cytokeratins. Wild type, Ts65Dn and Ts1 Cje mammary glands were stained with antibodies against the basal cell cytokeratin CK14 (red) and the luminal cell cytokeratin CK8 (green). D) In vitro proliferation of 1000 MRU cells isolated from wild type, Ts65Dn and Ts1 Cje mice. Notice that Ts65Dn cells, but not Ts1 Cje cells form significantly fewer colonies compared to their wild type counterparts (p-value for wt/Ts65Dn=0.0001). The results were replicated more than four times with similar results. E) Frequency of mammary repopulating cells. Limiting dilution transplantation experiments were done to determine the frequency of wild type, Ts65Dn and Ts65Dn/Usp16$^{het}$ mammary epithelial cells able to generate mammary ducts in vivo. Note that there is a marked decrease of repopulating cells only in Ts65Dn mice. Frequency was determined using the L-calc program, Stem Cell Technology (* p<0.001;  p<0.01). Three independent experiments were performed, two for Ts65Dn/Usp16$^{het}$. F) Downregulation of USP16 by shRNA lentiviral infection partially rescues the in vivo defects shown by Ts65Dn mammary cells (p=0.03). Limiting dilution transplantation experiments were done to determine the ability of shC and shUSP16 infected Ts65Dn mammary epithelial cells to generate mammary ducts in vivo. Three independent experiments were performed. On the right, area quantification for mammary outgrowths formed by Ts65Dn mammary epithelial cells transduced with a GFP-shC or GFP-shUSP16 lentivirus is shown (p=0.007).
Figure 4:
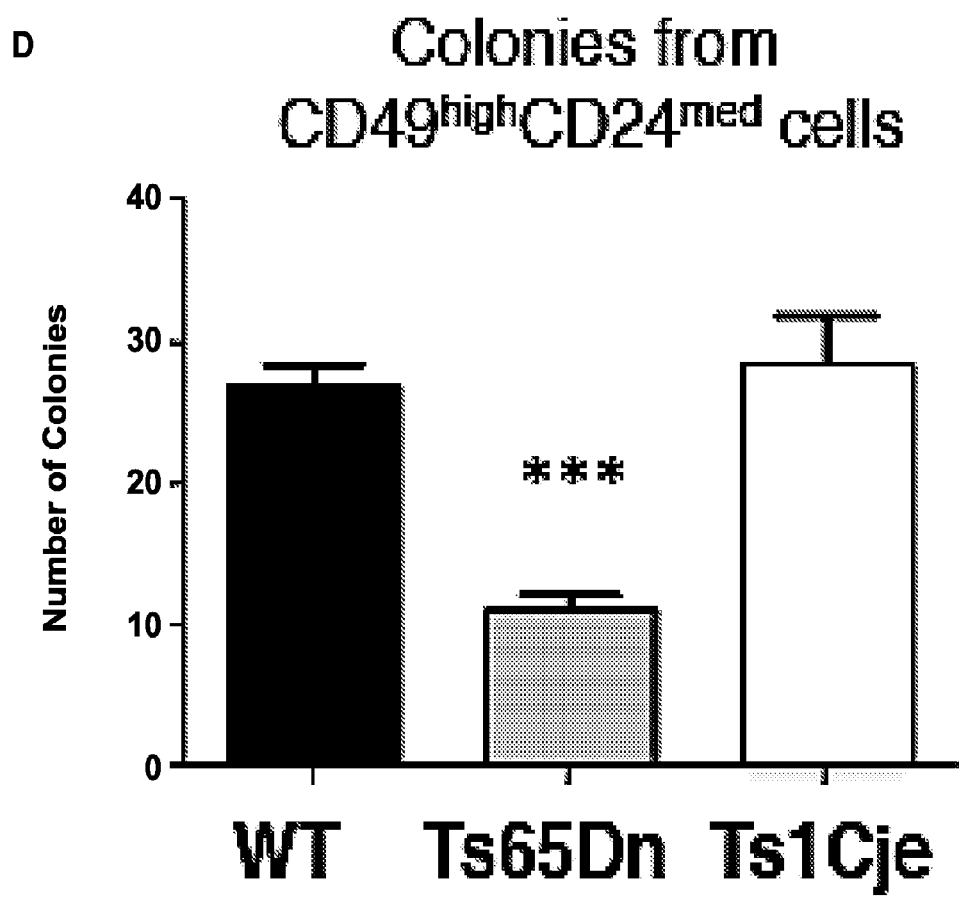
Figure 4:
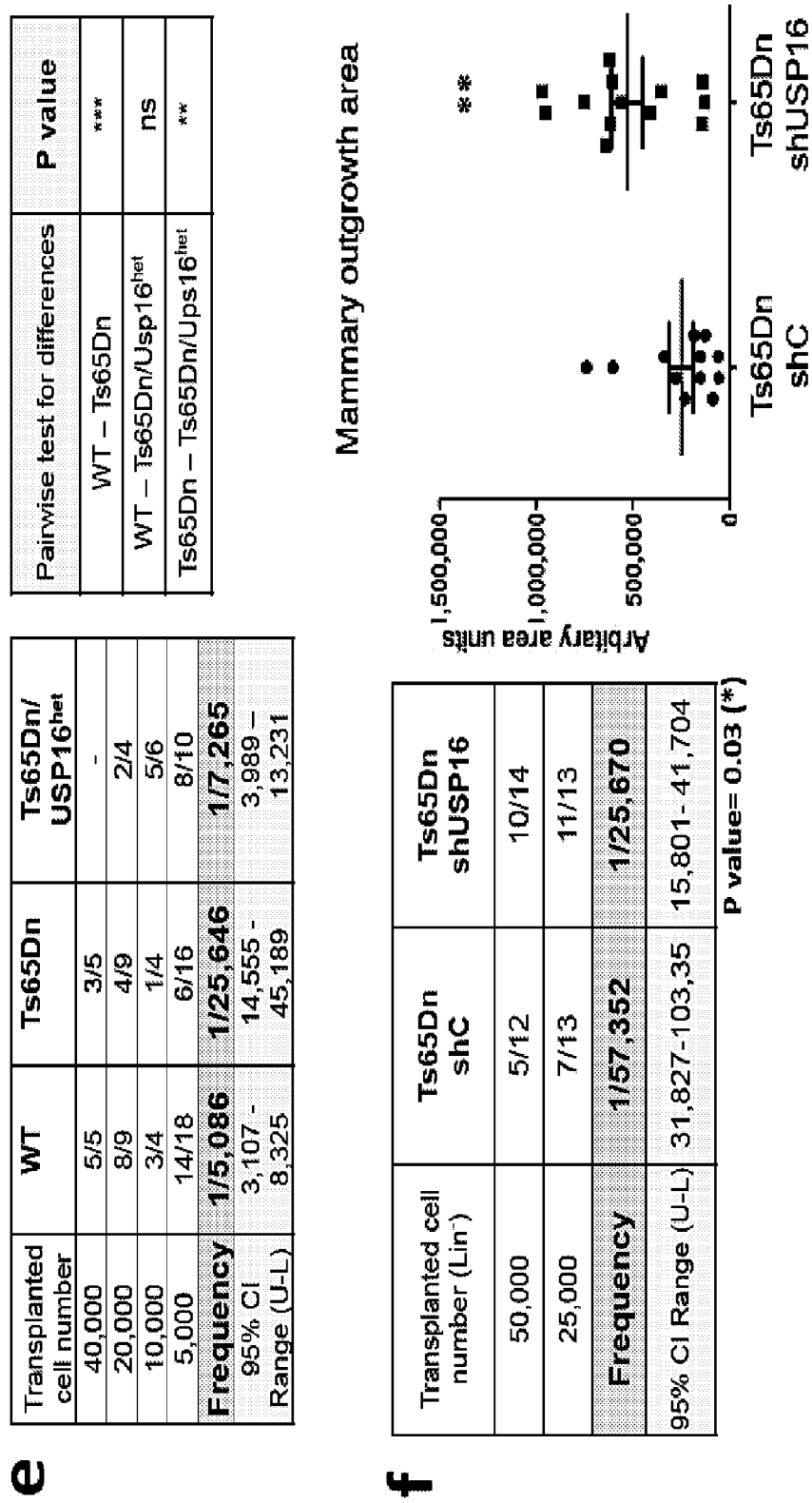
Figure 12:
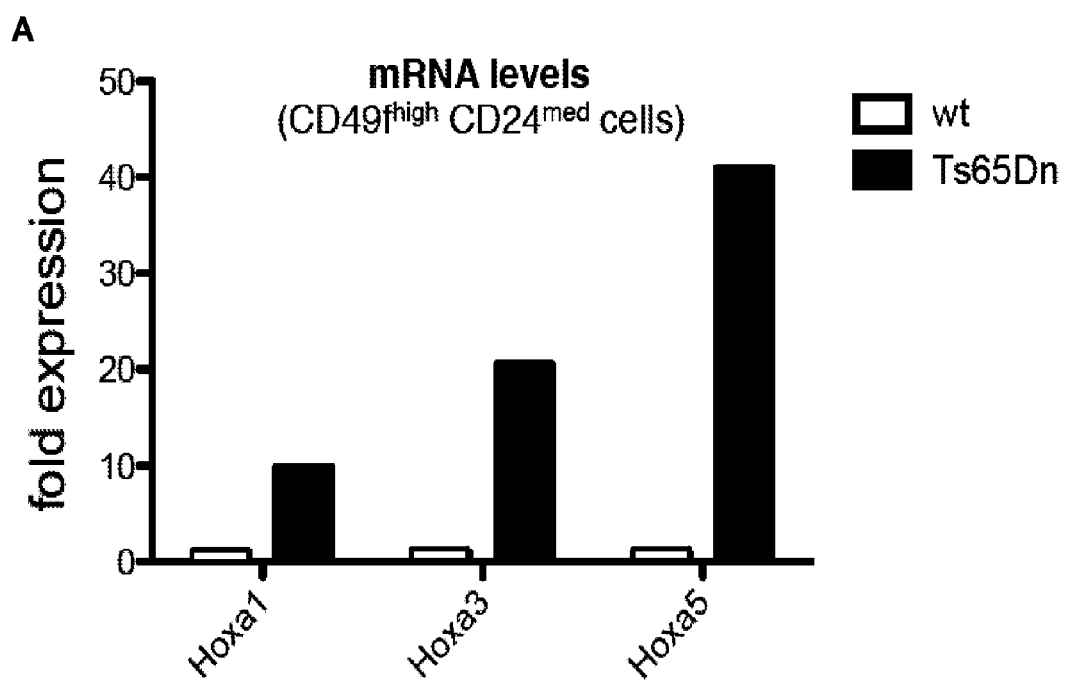
FIG. 12. Defects in mammary glands in DS mice models. A) Quantitative real-time PCR was used to measure expression of different Hox mRNA levels in wildtype (white) and Ts65Dn (black) in CD49highCD24med cells. Hox1, Hox3 and Hox5 are expressed at higher levels in Ts65Dn cells. B) Single cell suspension of mammary cells were analyzed by FACS and gated on live Lineage– cells (Ter119–, CD45–, CD31–) (first row). The second row shows Lin– cells stained for CD49f and CD24. We observed a perturbation in overall FACS profile with reduction of basal and luminal cells (indicated gates) in Ts65Dn mice but not in Ts1Cje mice. These experiments were repeated at least 5 times for each group. C) Mammary glands were stained with antibodies against the basal cytokeratin CK14 (red) and the luminal cytokeratin CK8 (green). Note that there is a marked increase in cells that co-stain for both cytokeratins in mammary epithelium of the Ts65Dn mouse. D) Pearson's correlation analyses (Lumosity software) quantifying the enrichment for co-staining of luminal and basal markers in Ts65Dn mammary glands.
Figure 12:
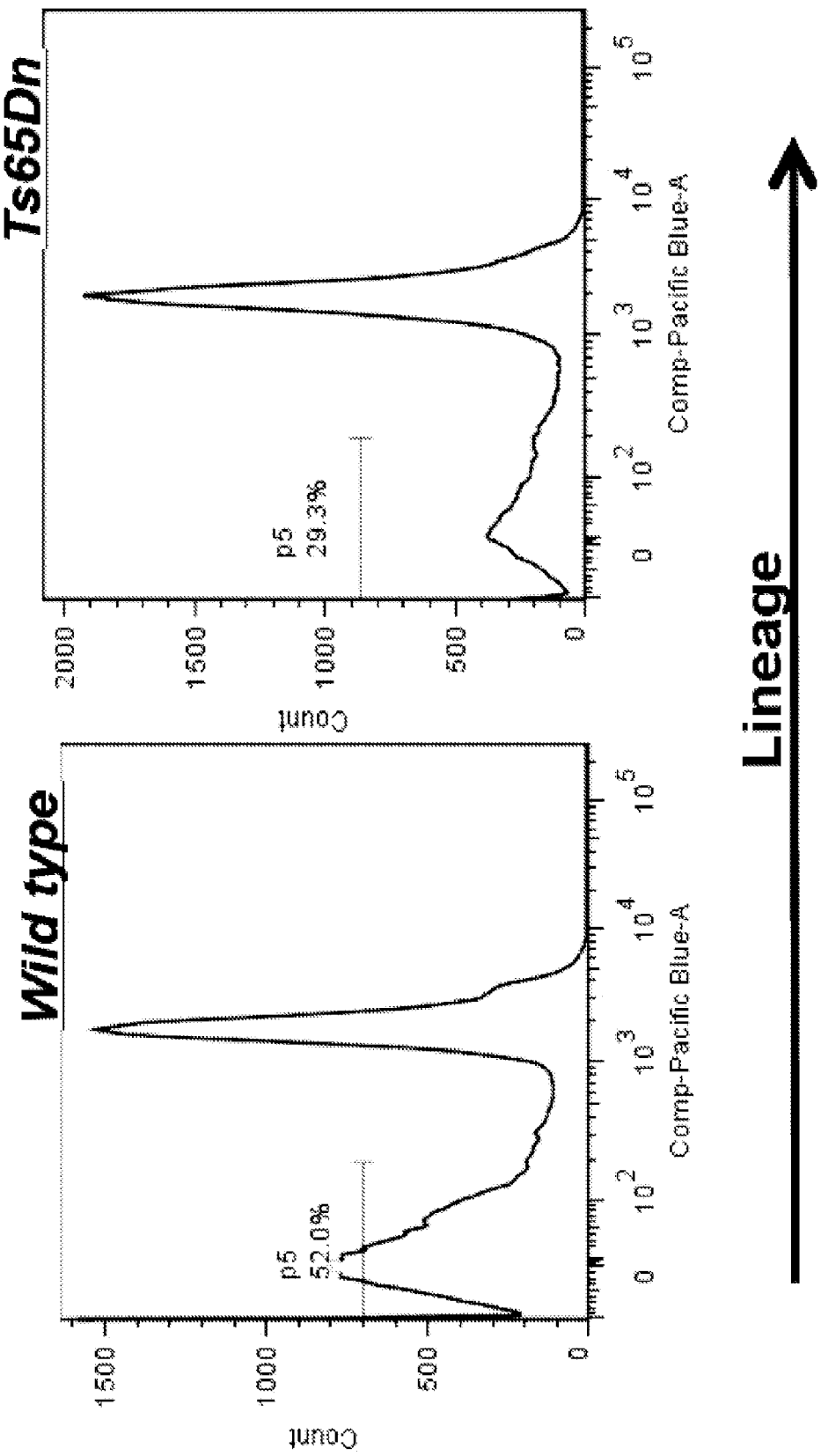
Figure 12:
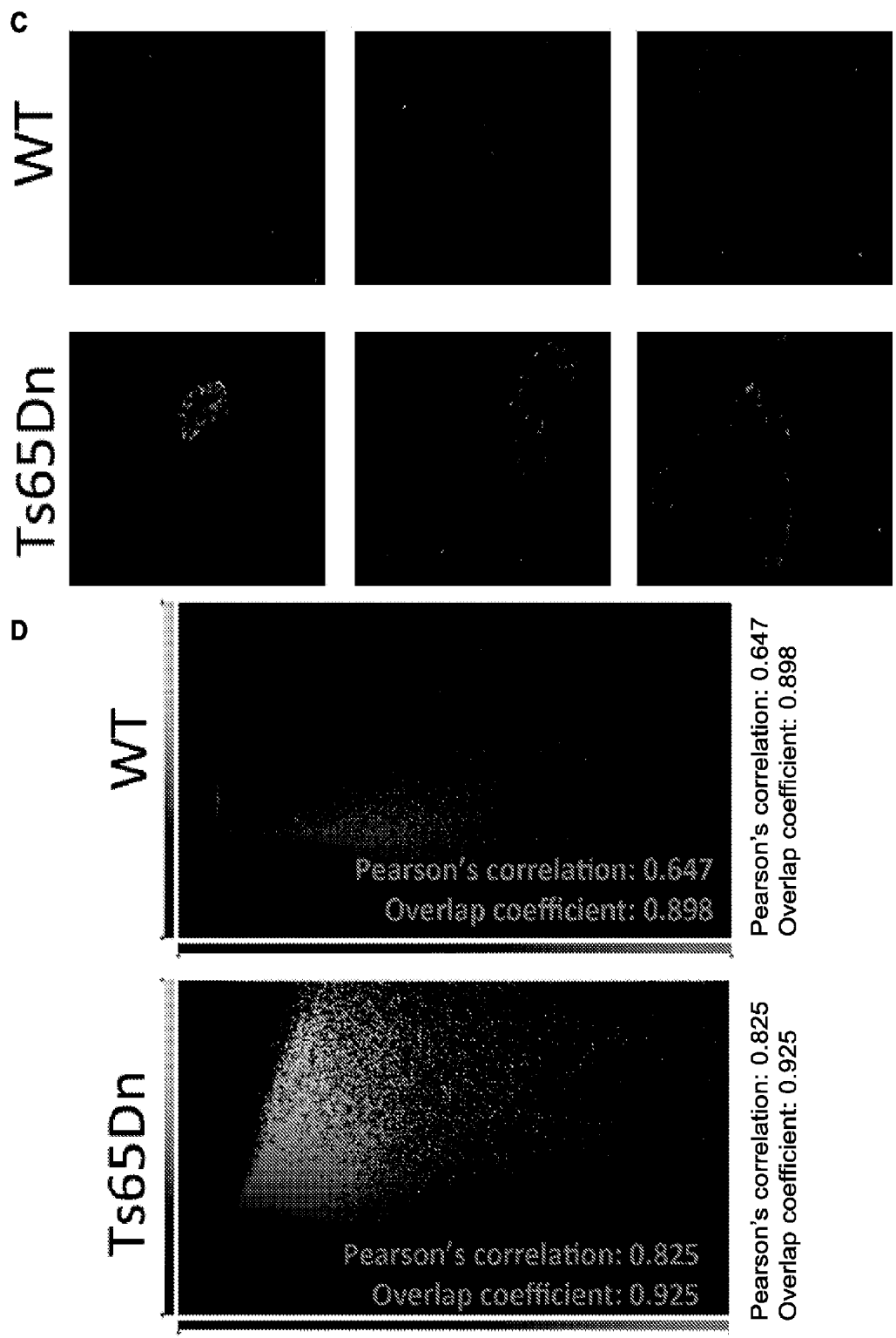

USP16 plays a role in the control of epithelial cell proliferation in the mammary glands of Ts65Dn mice. PRC1 plays an important role in the mammary gland, and loss of Bmi1 results in severe mammary epithelium growth defects (Pietersen, A. M. et al. Bmi1 regulates stem cells and proliferation and differentiation of committed cells in mammary epithelium. *Curr. Biol.* 18, 1094-1099 (2008)). We therefore asked whether the extra copy of Usp16 in Ts65Dn mice might affect the expansion of mammary epithelial cells. As expected, Usp16 mRNA expression was increased approximately 1.5 fold in Ts65Dn CD49f⁺CD24$^{med}$Lin⁻ cells (which are enriched for Mammary Repopulating Units or MRUs (Stingl, J. et al. Purification and unique properties of mammary epithelial stem cells. *Nature* 439, 993-997 (2006); Shackleton, M. et al. Generation of a functional mammary gland from a single stem cell. *Nature* 439, 84-88 (2006)) compared to wild type (FIG. 4a). Moreover, several Hox genes, usually repressed by the polycomb complex PRC1, were highly expressed in Ts65Dn cells (FIG. 12a). Immuno-phenotypical analysis of the breast tissue showed an alteration in the mammary duct organization of Ts65Dn, but not in Ts1 Cje mice (FIG. 12b). In particular, there was a significant reduction of the overall number of CD31⁻CD45⁻TER119⁻ (Lin⁻) cells (FIG. 4b). Moreover, cytokeratin staining in Ts65Dn mice showed that compared to wild type, Ts65Dn mice, but not Ts1cje mice, have an increased number of cells that co-express the luminal cell cytokeratin CK8 and the basal cell cytokeratin CK14 (FIG. 4c and FIG. 12c-d).

Next, CD49f⁺CD24$^{med}$Lin⁻ cells, a population enriched with transplantation abilities (Stingl, J. et al. Purification and unique properties of mammary epithelial stem cells. *Nature* 439, 993-997 (2006); Shackleton, M. et al. Generation of a functional mammary gland from a single stem cell. *Nature* 439, 84-88 (2006)), were tested for their capacity to expand in vitro in 3D culture conditions. Ts65Dn, but not Ts1 Cje, cultures showed a reduced number of colonies (FIG. 4d). To further assess the properties of Ts65Dn breast epithelial cells, mammary transplantation assays with Lin⁻ cells were performed. There was a significant decrease in the frequency of Ts65Dn Lin⁻ cells able to form mammary outgrowths (FIG. 4e). Notably, the ability to form glands of Lin⁻ Ts65Dn/Usp16$^{het}$ cells, which express only two copies of Usp16, was comparable to wild type cells.

To further assess the role of an extra copy of Usp16 in the Ts65Dn mammary epithelium, lentiviral downregulation of Usp16 in Ts65Dn Lin⁻ cells was performed (FIG. 4f). There was a two-fold increase in the calculated frequency of MRUs in shUSP16 infected Lin− Ts65Dn cells, and the derived outgrowths were larger compared to cells infected with control shRNA (FIG. 4f). However, we were unable to generate mammary glands in secondary transplants of the Ts65Dn/Usp16$^{het}$ mammary epithelial cells, suggesting that there might be other genes affecting the proliferation of these cells in Ts65Dn mice.

Figure 5:
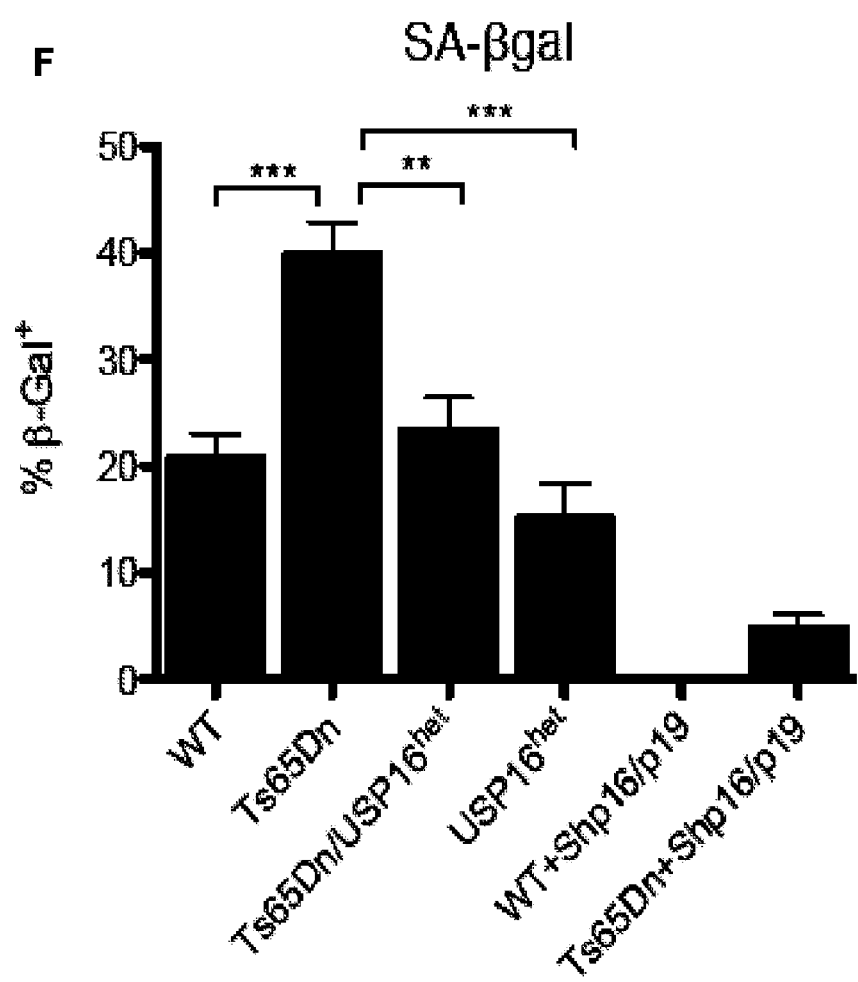
FIG. 5. Proliferation and senescence are controlled by USP16 in Ts65Dn fibroblasts. A) Expression of p16$^{Ink4a}$ and p19$^{Arf}$ mRNA in MEFs during passaging. Changes in expression levels are shown until P7. B) SA-βgalactosidase staining in wild type and Ts65Dn MEFs at P4. Representative pictures are shown. The percentages of positive cells are shown on the right. Experiments were replicated with three different MEF lines per genotype (p=0.001). C) ChIP analyses on six Ink4 locus upon precipitation with H2AUb antibody of MEF chromatin samples. Analyses have been performed at least twice with two different MEF cultures per genotype. Values are normalized for the amount of input chromatin. As a control, ActinB levels were also studied. D) Downregulation of Usp16 normalizes expression of Ink4a/Arf by Ts65Dn cells. The expression levels of p16$^{Ink4a}$ and p19$^{Arf}$ by passage 6 in infected MEFs are shown. Levels of Usp16 upon lentiviral downregulation are also shown. E) Proliferation of TTFs derived from wildtype, Ts65Dn, Ts65Dn/USP16$^{het}$, and USP16$^{het}$ mice. Cells were seeded at passage 2 and counted every two days by trypan blue exclusion. Ts65Dn TTFs are not able to proliferate in vitro, while Ts65Dn/USP16$^{het}$ TTFs do. At least three different lines were used for each condition. F) SA-βgalactosidase positive cells in TTF cultures derived from wildtype, Ts65Dn, Ts65Dn/USP16$^{het}$, and USP16$^{het}$ mice or in wild-type and Ts65Dn TTFs infected with a hairpin targeting p16/p19. Cells were analyzed at P3. Note that there is an increase of positive cells in Ts65Dn TTFs compared to wildtype, while the phenotype is reverted in Ts65/USP16$^{het}$ TTFs (* p<0.001;  p<0.01). G) p16 expression is shown as the percentage of cells tested positive by immunofluorescence. Wild type and Ts65Dn TTFs co-transduced with sort hairpins for p16 and p19 are negative as expected (*** p<0.01; * p<0.05). H) Proliferation of Ts65Dn TTFs infected with a hairpin targeting p16/p19 increases. Also wild type TTFs proliferate more upon downregulation of p16/p19. This experiment was repeated three times with similar results.

Modulation of Ink4a/Arf by Usp16 in Ts65Dn cells. One of the best-characterized PRC1 target loci playing a role in HSCs, neural progenitor cells, mammary epithelial cells and fibroblasts is CDKN2a, which encodes two separate tumor suppressors, p16$^{Ink4a}$ and p19$^{Arf}$. Expression of p16$^{Ink4a}$ and p19$^{Arf}$ normally increases with age in both rodent and human tissues (Liu, Y. et al. Expression of p16(INK4a) in peripheral blood T-cells is a biomarker of human aging. *Aging Cell* 8, 439-448 (2009); Krishnamurthy, J. et al. Ink4a/Arf expression is a biomarker of aging. *J. Clin. Invest.* 114, 1299-1307 (2004); Janzen, V. et al. Stem-cell ageing modified by the cyclin-dependent kinase inhibitor p16INK4a. *Nature* 443, 421-426 (2006)). In MEFs derived from Ts65Dn mice, we observed during serial passaging (from passage 4 to passage 7) a faster increase in the RNA expression levels of both genes compared to wild type MEFs (FIG. 5a). There was also a clear enrichment for SA-βGal positive cells in Ts65Dn MEFs compared to their wild type counterparts, suggesting a process of accelerated senescence (FIG. 5b). Consistent with the reduced levels of H2AK119 ubiquitination observed in Ts65Dn MEFs (FIG. 8c), chromatin immunoprecipitation (ChIP) analyses demonstrated a decrease in H2AK119 ubiquitin of the Ink4a/Arf locus in Ts65Dn MEFs (Negishi, M. et al. A novel zinc finger protein Zfp277 mediates transcriptional repression of the Ink4a/arf locus through polycomb repressive complex 1. *PLoS ONE* 5, e12373 (2010)) (FIG. 5c). Finally, lentiviral downregulation of Usp16 with two different hairpins in Ts65Dn MEF cultures restored lower levels of p16$^{Ink4a}$ and p19$^{Arf}$, suggesting that Usp16 is contributing to the senescence process (FIG. 5d).

Figure 13:
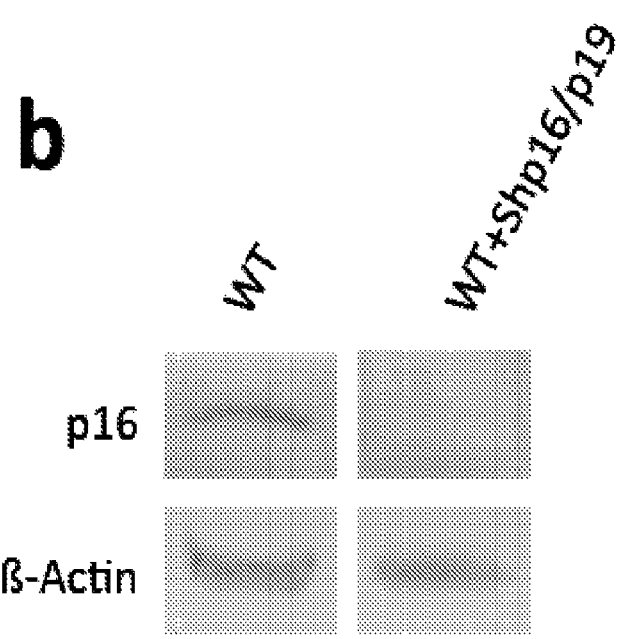
FIG. 13. SA-βgal and p16 expression in Ts65Dn fibroblasts are affected by levels of USP16 and CDKN2a. A) Representative pictures of SA-βgal staining in TTFs. On the right, the graph shows the percentage of SA-βgal+ cells in different conditions. Each dot represents a TTF culture derived from a different mouse. The last two columns refers to WT and Ts65Dn fibroblasts infected with hairpins against p16/p19. B) Western blot analyses verifies knockDown's of p16. βactin works as a loading control. C) Representative pictures of p16 immunostaining (left) and quantification of the percentage of positive cells (right panel). Each dot represents a TTF culture derived from a different mouse. The hairpin effectively ablates p16 expression.

Next, adult terminal tail fibroblasts (TTFs) from wild type, Ts65Dn, and Ts65Dn/Usp16$^{het}$ mice cells were also examined. Ts65Dn fibroblasts showed a marked proliferation deficit (FIG. 5e) and high levels of senescence, as shown by SA-βGal staining and by p16 expression (FIG. 5f-g and FIG. 13). However, loss of a single normal allele of Usp16 significantly rescued the proliferation defect and premature senescence of these cells (FIG. 5e-g). Bmi1 depletion results in a proliferation defect strongly resembling that seen in Ts65Dn fibroblasts. In Bmi1⁻/⁻ MEFs, this is in part due to loss of PRC1-mediated repression of Cdkn2a (Jacobs, J. J. et al. The oncogene and Polycomb-group gene bmi-1 regulates cell proliferation and senescence through the ink4a locus. *Nature* 397, 164-168 (1999)). Similar to Bmi1 mutation, the senescence and proliferation defect of Ts65Dn fibroblasts was rescued by an shRNA targeting Cdkn2a (FIG. 5f-h and FIG. 13b-c).

Figure 6:
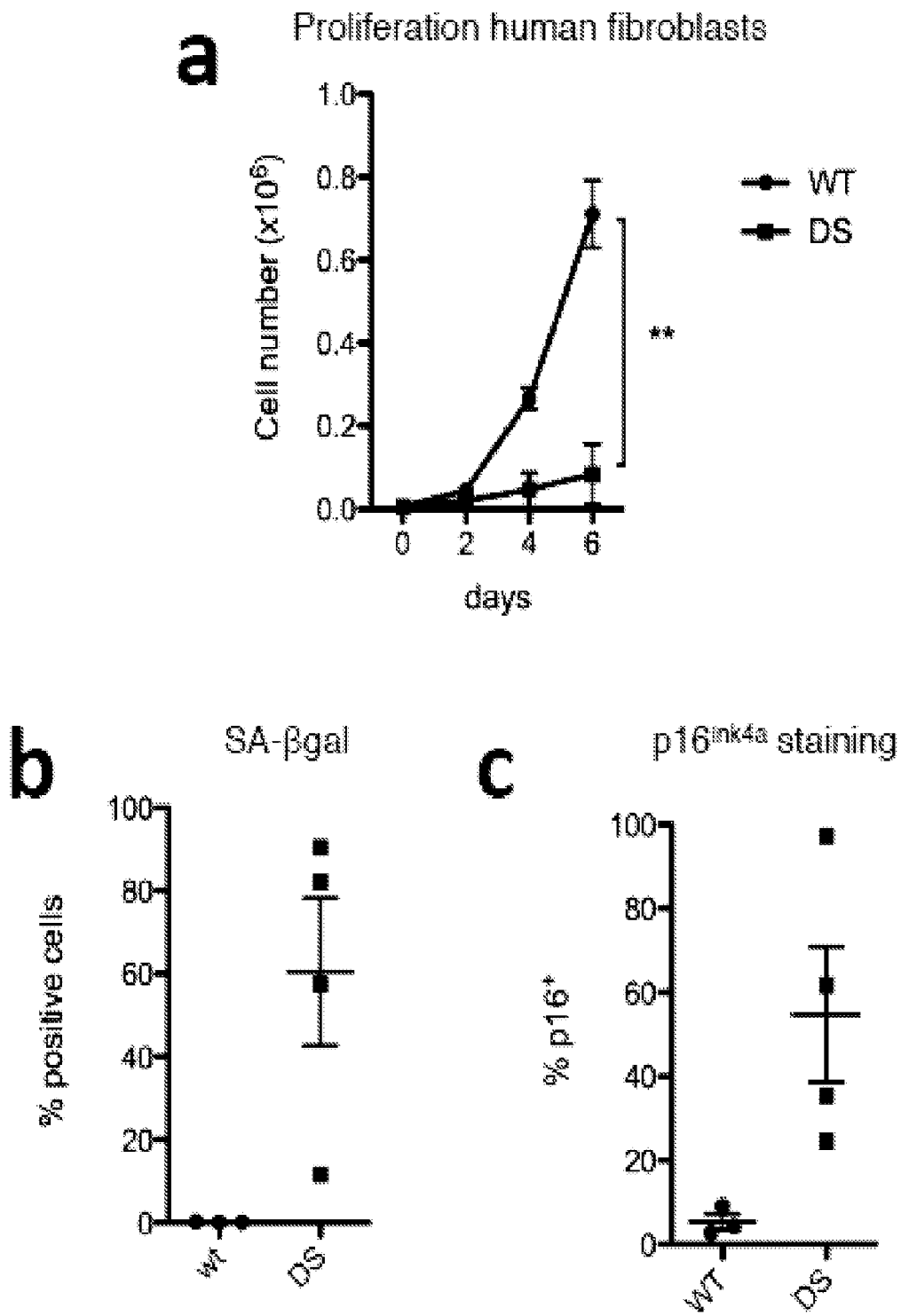
FIG. 6. Human DS fibroblasts show a proliferation defect that depends on USP16 levels. A). Proliferation analysis of three wild type and four DS human fibroblasts (less than 10 passages in culture) shows a drastic inability of DS cell to expand in vitro (*** p<0.01). B-C) SA-βgalactosidase and p16 expression is shown as the percentage of stained cells. Every dot represents fibroblasts isolated from different individuals. DS cells exhibit a higher expression of the senescence markers SA-βgalactosidase and of p16. D) Overepxression of USP16 by lentivirus infection affects the proliferation of two different wild type fibroblast lines (three replicates per time point, experiments were repeated twice). E) Downregulation of USP16 in DS fibroblasts promotes proliferation (three replicates per time point, repeated twice). F) Overexpression of USP16 reduces the formation of neurospheres derived from human adult SVZ cells. The right panel quantifies the number of spheres in the first and second passages. P,0.0001. All the experiments were replicated at least twice. Luc, luciferase.
Figure 6:
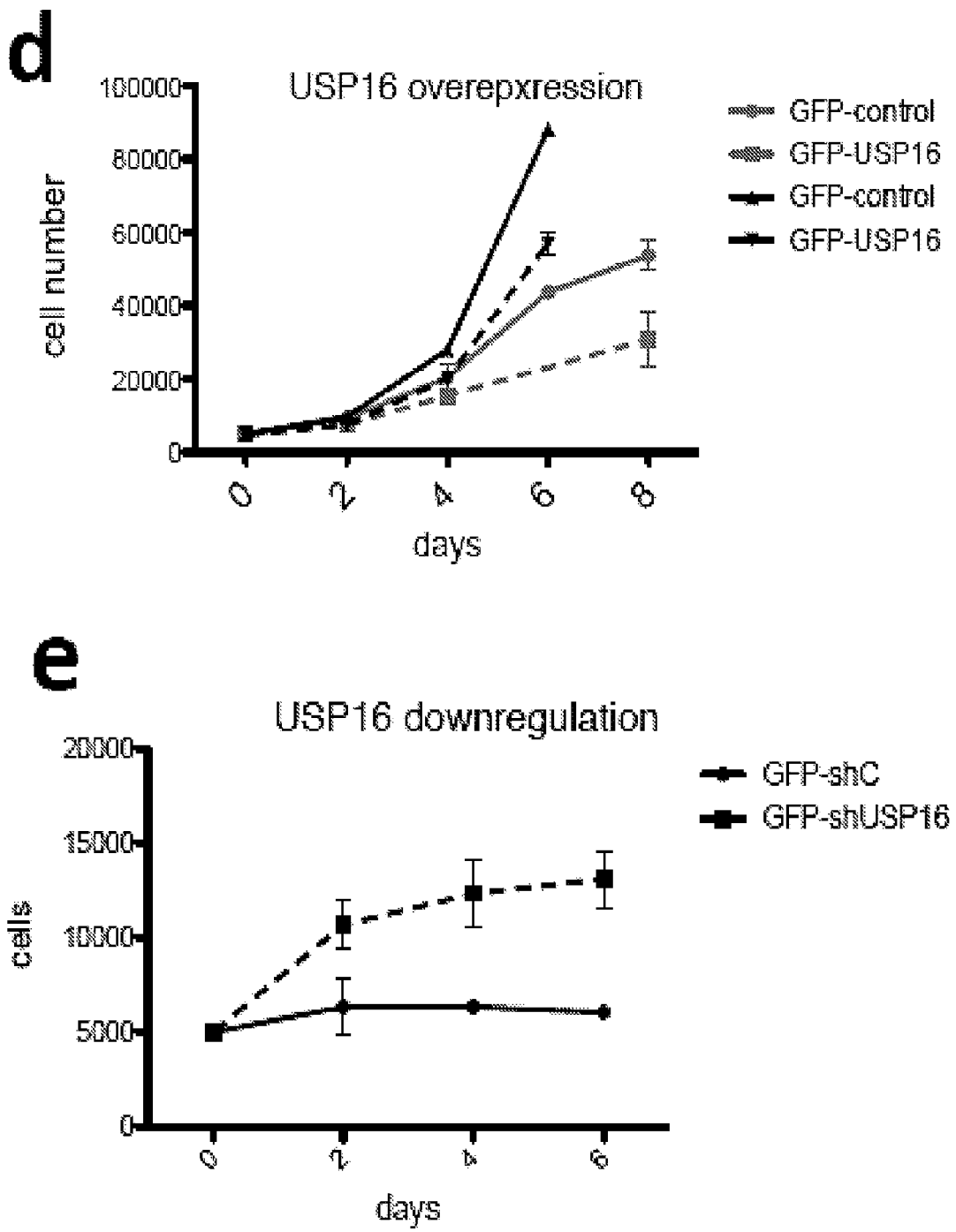
Figure 6:
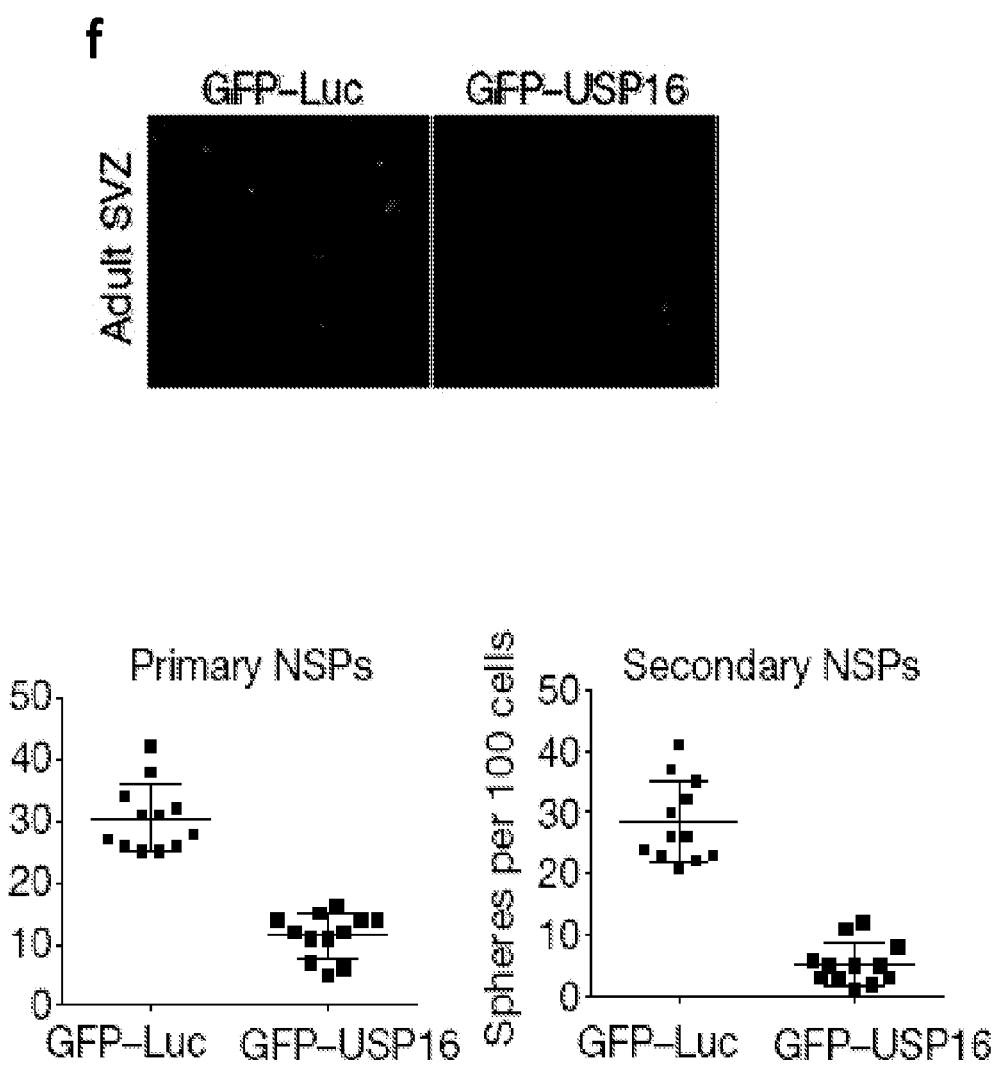
Figure 14:
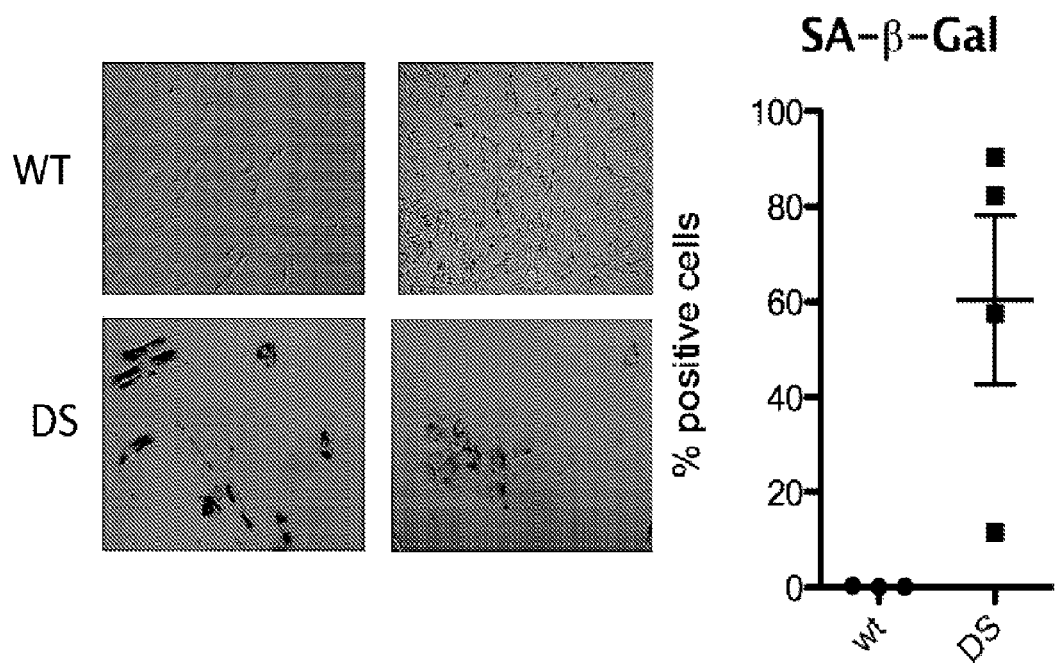
FIG. 14. Human fibroblasts cultures. A) Representative pictures of SA-βgal staining in human fibroblasts. On the right, the graph shows the percentage of SA-βgal+ cells in different conditions. Each dot represents a culture derived from a different individual. B) Quantitative real-time PCR was used to measure the expression of USP16 mRNA after lentiviral infection with constructs overexpressing Bmi1 (left) or expressing a hairpin targeting human Usp16. C) Bmi1 ovrepxression significantly increases the proliferation of fibroblasts derived from a DS carrier. The effect on wild type fibroblast is not significant. On the right, the levels of expression of Bmi1 mRNA were quantified by quantitative real-time PCR. Experiment was repeated twice with similar results.
Figure 14:
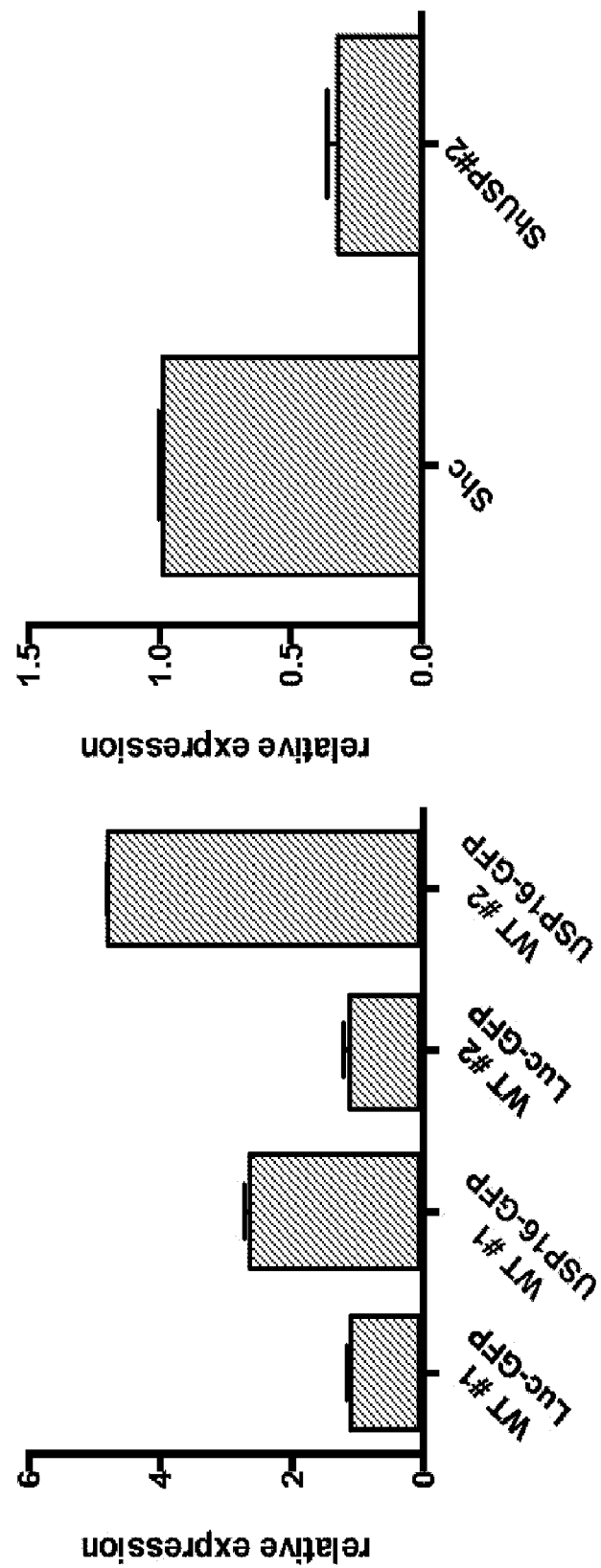

Potential Role for USP16 in Human Down's Syndrome. Fibroblasts isolated from four human Down's syndrome patients were tested to see if USP16 might limit their proliferation. Consistent with previous reports (Carmeliet, G. et al. Cellular ageing of Alzheimer's disease and Down's syndrome cells in culture. *Mutat. Res.* 256, 221-231 (1991); Contestabile, A. et al. Widespread impairment of cell proliferation in the neonate Ts65Dn mouse, a model for Down's syndrome. *Cell Prolif.* 42, 171-181 (2009); Kimura, M. et al. Proliferation dynamics in cultured skin fibroblasts from Down's syndrome subjects. *Free Radic. Biol. Med.* 39, 374-380 (2005)), DS fibroblasts proliferation was impaired compared to wild type controls (FIG. 6a). This was associated with increased senescence as measured by expression of SA-βGal and p16$^{Ink4a}$ (FIG. 6b-c and FIG. 14). To determine whether USP16 overexpression might contribute to the proliferation defect, we did gain of function experiments in normal fibroblasts and loss of function experiments in Down's syndrome fibroblasts. Transduction of normal foreskin fibroblasts with USP16 slowed the proliferation of normal wild type fibroblasts (FIG. 6d and FIG. 14b). Conversely, shRNA mediated downregulation of USP16 or overexpression of BMI1 resulted in increased proliferation capacity of DS fibroblasts (FIG. 14b-c). Interestingly, overexpression of USP16 in two different cultures of human neural progenitor cells (from one paediatric and one adult patient) reduced their in vitro expansion potential and the formation of neurospheres (FIG. 6f). These experiments suggest that a third copy of USP16 might have a role in the pathology associated in patients with Down's syndrome.

Discussion

Our data indicate that some of the pathology associated with the Ts65Dn mouse model of Down's syndrome is secondary to a broad defect in tissue homeostasis and a self-renewal defect in somatic stem and progenitor cells. The comparison of the HSC compartments between two different mouse models for DS (Ts65Dn and Ts1Cje) shows that a limited number of genes may play a crucial role in this defect. The change in self-renewal of HSCs and neural progenitors, as well as proliferation defects of mammary epithelial cells and fibroblasts in Ts65Dn mice is linked in part to the trisomy of Usp16, a negative modifier of the Polycomb Repressive Complex 1 (PRC1) activity (Joo, H.-Y. et al. Regulation of cell cycle progression and gene expression by H2A deubiquitination. *Nature* 449, 1068-1072 (2007)). PRC1 is known to regulate senescence and self-renewal of multiple somatic stem cells. Supporting this notion, Usp16 down regulation in Ts65Dn mice to paraphysiological levels restores proliferative capacities of HSCs, neural progenitors, mammary epithelial cells and fibroblasts.

Clearly, other genes also play a role in the multitude of traits, such as craniofacial abnormalities and congenital heart defects, seen in Down's syndrome (Arron, J. R. et al. NFAT dysregulation by increased dosage of DSCR1 and DYRK1A on chromosome 21. *Nature* 441, 595-600 (2006)). Moreover, we have not been able to document that loss of Usp16 rescues in the ability of mammary MRUs to be serially transplanted, which suggests that other gene(s) could also contribute to the self-renewal defect of Ts65Dn stem cell compartments. Nonetheless, the rescue of HSCs and neural progenitors is significant, showing that Usp16 trisomy plays an important role in the somatic cells of these mice. Finally, the observation that inhibition of USP16 in human Down's syndrome fibroblasts increases proliferation indicates that this gene also plays a role in tissue homeostasis defects in patients with Down's syndrome.

Down's syndrome is associated with increased rates of childhood leukemia and decreased rates of adult solid tumors (Yang, Q. et al. Mortality associated with Down's syndrome in the USA from 1983 to 1997: a population-based study. *Lancet* 359, 1019-1025 (2002); Satgé, D. et al. A tumor profile in Down's syndrome. *Am. J. Med. Genet.* 78, 207-216 (1998)). Other syndromes causing bone marrow failure, such as Fanconi's anemia, predispose to leukemia. Lymphoid leukemias in Down's syndrome patients frequently involve mutation of CDKN2a (Novara, F. et al. Different molecular mechanisms causing 9p21 deletions in acute lymphoblastic leukemia of childhood. *Hum. Genet.* 126, 511-520 (2009)). Because Cdkn2a appears to play a role in the proliferation defects caused by trisomy of Usp16, mutations of CDKN2A could give DS HSCs a strong selection advantage.

PRC1 regulation of stem cells is effected in part through inhibition of the Cdkn2a locus via ubiquination of H2A (Molofsky, A. V. et al. Bmi-1 dependence distinguishes neural stem cell self-renewal from progenitor proliferation. *Nature* 425, 962-967 (2003); Jacobs, J. J. et al. The oncogene and Polycomb-group gene bmi-1 regulates cell proliferation and senescence through the ink4a locus. *Nature* 397, 164-168 (1999); Bruggeman, S. W. M. et al. Ink4a and Arf differentially affect cell proliferation and neural stem cell self-renewal in Bmi1-deficient mice. *Genes Dev.* 19, 1438-1443 (2005)). We find that trisomy of Usp16 results in a reduction of histone H2A ubiquitination and elevated levels of p16$^{Ink4a}$ and p19$^{Arf}$. Therefore, Usp16 has the opposite biochemical and functional effects as PRC1. In fact, the developmental defects of Ts65Dn mice resemble a hypomorph of mice mutant for the PRC1 component Bmi1. This includes defects in HSCs, breast development, neural progenitors and early senescence of fibroblasts (Park, I.-K. et al. Bmi-1 is required for maintenance of adult self-renewing haematopoietic stem cells. *Nature* 423, 302-305 (2003); Pietersen, A. M. et al. Bmi1 regulates stem cells and proliferation and differentiation of committed cells in mammary epithelium. *Curr. Biol.* 18, 1094-1099 (2008); Molofsky, A. V., et al. Bmi-1 promotes neural stem cell self-renewal and neural development but not mouse growth and survival by repressing the p16Ink4a and p19Arf senescence pathways. *Genes Dev.* 19, 1432-1437 (2005)). Mutation of Cdkn2a partially, but not completely, corrects the somatic stem cell defects seen in Bmi1 mutant mice (Jacobs, J. J. et al. The oncogene and Polycomb-group gene bmi-1 regulates cell proliferation and senescence through the ink4a locus. *Nature* 397, 164-168 (1999); Bruggeman, S. W. M. et al. Ink4a and Arf differentially affect cell proliferation and neural stem cell self-renewal in Bmi1-deficient mice. *Genes Dev.* 19, 1438-1443 (2005); Jacobs, J. J. et al. The oncogene and Polycomb-group gene bmi-1 regulates cell proliferation and senescence through the ink4a locus. *Nature* 397, 164-168 (1999); Bruggeman, S. W. M. et al. Ink4a and Arf differentially affect cell proliferation and neural stem cell self-renewal in Bmi1-deficient mice. *Genes Dev.* 19, 1438-1443 (2005)). Similarly, down-regulation of p16$^{Inkk4a}$, or overexpression of BMI1, partially rescues the proliferation defects in murine and human fibroblasts trisomic for USP16. These results indicates that trisomy of Usp16 contributes to the cellular defects seen in Ts65Dn mice due to increased removal of H2A ubiquitin.

Our data demonstrate a new axis of regulation of self-renewal in multiple tissues. We have shown that normal expression of Usp16 is critical for normal tissue homeostasis, and perturbation of this balance contributes to abnormal tissue homeostasis. We believe that our study has broad implications for understanding one of the most common genetic abnormalities in humans, Down's syndrome. Future studies on the role of Usp16 and its mechanism of action could potentially lead to the development of therapeutic tools that ameliorate the stem cell pathologies associated with this syndrome.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of treating a medical condition associated with a reduced rate of stem cell self-renewal or that will be responsive to an increased rate of stem cell self-renewal, the method comprising:
administering an effective amount of an antagonist of H2A deubiquitinating enzyme USP16 to the individual, wherein the antagonist reduces the amount of USP16 in a cell or binds directly to USP16.

2. The method according to claim 1, wherein the antagonist is a nucleic acid.

3. The method according to claim 1, wherein the antagonist binds directly to USP16.

4. The method according to claim 3, wherein the antagonist reduces the amount of USP16 protein in the cell.

5. The method according to claim 4, wherein the antagonist is a USP16-specific nucleic acid inhibitor.

6. The method according to claim 1, further comprising administering an antioxidant.

7. The method according to claim 1, wherein the condition is a neurodevelopmental disorder; traumatic brain injury; neurodegenerative diseases; aging-associated disorder; condition associated with muscle atrophy; disease requiring the regeneration of pancreatic cells; disease requiring liver regeneration; or a condition requiring skin regeneration.

8. The method according to claim 7, wherein the condition is a neurodevelopmental disorder, traumatic brain injury, or neurodegenerative disease, and the treatment comprises an improvement in cognitive function.

9. The method according to claim 8, wherein the improvement in cognitive function comprises an improvement in memory.

10. The method according to claim 9, further comprising measuring memory before administering the agent and after administering the agent, wherein memory after administering the agent is improved relative to memory before administering the agent.

11. The method according to claim 7, wherein the neurodevelopmental disorder is Down's Syndrome, fragile-X syndrome, or autism.

12. The method according to claim 7, wherein the neurodegenerative disease is Alzheimer's Disease, Parkinson's disease, or ALS.

13. The method according to claim 12, wherein the Alzheimer's Disease is associated with Down's Syndrome.

14. The method according to claim 12 wherein the Alzheimer's Disease is associated with traumatic brain injury.

* * * * *

SEQUENCE LISTING

<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: Hairpin

<400> SEQUENCE: 1
ttctccgaac gtgtcacgt                                            19

<210> SEQ ID NO 2
<211> LENGTH: 21
<212> TYPE: DNA
<213> ORGANISM: Artificial Sequence
<220> FEATURE:
<223> OTHER INFORMATION: Hairpin

<400> SEQUENCE: 2
cgagtgctgt attccttata t                                         21

<210> SEQ ID NO 3
<211> LENGTH: 21
<212> TYPE: DNA
<213> ORGANISM: Artificial Sequence
<220> FEATURE:
<223> OTHER INFORMATION: Hairpin

<400> SEQUENCE: 3
ttctctggaa atacacctat g                                         21

<210> SEQ ID NO 4
<211> LENGTH: 21
<212> TYPE: DNA
<213> ORGANISM: Artificial Sequence
<220> FEATURE:
<223> OTHER INFORMATION: Hairpin

<400> SEQUENCE: 4
catcaagaca tcgtgcgata t                                         21

<210> SEQ ID NO 5
<211> LENGTH: 21
<212> TYPE: DNA
<213> ORGANISM: Artificial Sequence
<220> FEATURE:
<223> OTHER INFORMATION: Hairpin

<400> SEQUENCE: 5
gccatctaaa cggttcagtt t                                         21